(12) United States Patent
Lovell et al.

(10) Patent No.: US 9,757,334 B2
(45) Date of Patent: Sep. 12, 2017

(54) SURFACTANT-STRIPPED MICELLE COMPOSITIONS WITH HIGH CARGO TO SURFACTANT RATIO

(71) Applicant: The Research Foundation for The State University of New York, Amherst, NY (US)

(72) Inventors: Jonathan Lovell, Niagara Falls (CA); Yumiao Zhang, Buffalo, NY (US); Wentao Song, Brooklyn, NY (US); Jumin Geng, Buffalo, NY (US); Chulhong Kim, Ponhang-si (KR); Mansik Jeon, Pohang-si (KR)

(73) Assignee: The Research Foundation for The State University of New York, Buffalo, NY (US)

( * ) Notice: Subject to any disclaimer, the term of this patent is extended or adjusted under 35 U.S.C. 154(b) by 0 days.

(21) Appl. No.: 15/322,593

(22) PCT Filed: Jul. 2, 2015

(86) PCT No.: PCT/US2015/039082
§ 371 (c)(1),
(2) Date: Dec. 28, 2016

(87) PCT Pub. No.: WO2016/004369
PCT Pub. Date: Jan. 7, 2016

(65) Prior Publication Data
US 2017/0135955 A1    May 18, 2017

Related U.S. Application Data

(60) Provisional application No. 62/020,233, filed on Jul. 2, 2014, provisional application No. 62/020,249, filed on Jul. 2, 2014.

(51) Int. Cl.
| | | |
|---|---|---|
| A61K 9/107 | (2006.01) |
| A61K 47/34 | (2017.01) |
| A61K 31/122 | (2006.01) |
| A61K 49/00 | (2006.01) |
| A61K 38/13 | (2006.01) |
| A61K 31/343 | (2006.01) |
| A61K 31/7048 | (2006.01) |
| A61K 31/568 | (2006.01) |
| A61K 31/593 | (2006.01) |
| A61K 31/23 | (2006.01) |
| A61K 31/436 | (2006.01) |
| A61K 31/567 | (2006.01) |
| A61K 31/337 | (2006.01) |
| A61K 31/355 | (2006.01) |
| A61K 31/592 | (2006.01) |
| A61K 31/01 | (2006.01) |

(52) U.S. Cl.
CPC ............ *A61K 9/1075* (2013.01); *A61K 31/01* (2013.01); *A61K 31/122* (2013.01); *A61K 31/23* (2013.01); *A61K 31/337* (2013.01); *A61K 31/343* (2013.01); *A61K 31/355* (2013.01); *A61K 31/436* (2013.01); *A61K 31/567* (2013.01); *A61K 31/568* (2013.01); *A61K 31/592* (2013.01); *A61K 31/593* (2013.01); *A61K 31/7048* (2013.01); *A61K 38/13* (2013.01); *A61K 47/34* (2013.01); *A61K 49/0021* (2013.01); *A61K 49/0032* (2013.01); *A61K 49/0041* (2013.01)

(58) Field of Classification Search
CPC .... A61K 9/1075; A61K 31/01; A61K 31/122; A61K 31/23; A61K 31/337; A61K 31/343; A61K 31/355; A61K 31/436; A61K 31/567; A61K 31/568; A61K 31/592; A61K 31/593; A61K 31/7048; A61K 38/13; A61K 47/34; A61K 49/0021; A61K 49/0032; A61K 49/0041
See application file for complete search history.

(56) References Cited

U.S. PATENT DOCUMENTS

| | | |
|---|---|---|
| 5,281,420 A | 1/1994 | Kelm et al. |
| 6,649,702 B1 | 11/2003 | Rapoport et al. |
| 7,744,919 B2 | 6/2010 | Cho et al. |
| 7,923,026 B2 | 4/2011 | Moschwitzer |
| 8,173,167 B2 | 5/2012 | Kwon et al. |
| 8,519,051 B2 | 8/2013 | Bobe et al. |
| 8,551,526 B2 | 10/2013 | Johnston et al. |
| 8,586,681 B2 | 11/2013 | Zhao |
| 8,858,965 B2 | 10/2014 | Kwon et al. |
| 8,945,627 B2 | 2/2015 | Kwon et al. |

(Continued)

FOREIGN PATENT DOCUMENTS

| | | |
|---|---|---|
| CN | 102335119 | 2/2012 |
| CN | 102626518 A | 8/2012 |

(Continued)

OTHER PUBLICATIONS

Zhang et al., Non-invasive multimodal functional imaging of the intestine with frozen micellar naphthalocyanines, Nature Nanotechnology, Jul. 6, 2014, pp. 631-638.

*Primary Examiner* — Robert Cabral
(74) *Attorney, Agent, or Firm* — Hodgson Russ LLP

(57) ABSTRACT

Provided are compositions and methods relating to hydrophobic agent loaded-micelle. The micelles comprise surfactant (such as poloxamer) and have hydrophobic agents incorporated therein. The compositions substantially lack surfactant that is not associated with the micelles. The compositions are able to achieve high hydrophobic agent: surfactant molar ratio. The compositions can be used for drug delivery and imaging applications.

17 Claims, 44 Drawing Sheets

(56) References Cited

U.S. PATENT DOCUMENTS

| | | |
|---|---|---|
| 2003/0138489 A1 | 7/2003 | Meadows et al. |
| 2004/0258718 A1 | 12/2004 | Meadows et al. |
| 2006/0073199 A1 | 4/2006 | Chaubal et al. |
| 2007/0148232 A1 | 6/2007 | Crew et al. |
| 2008/0038353 A1 | 2/2008 | Lavasanifar et al. |
| 2010/0270695 A1 | 10/2010 | Radosz et al. |
| 2011/0223206 A1 | 9/2011 | Lebouille et al. |
| 2012/0321715 A1 | 12/2012 | Kwon et al. |
| 2013/0150311 A1 | 6/2013 | Pietrzynski et al. |
| 2013/0345297 A1 | 12/2013 | Lee et al. |
| 2014/0023590 A1 | 1/2014 | Gao et al. |

FOREIGN PATENT DOCUMENTS

| | | |
|---|---|---|
| CN | 103446040 | 12/2013 |
| CN | 104546708 | 4/2015 |
| WO | 2013190167 | 12/2013 |

Figure 22

Figure 23
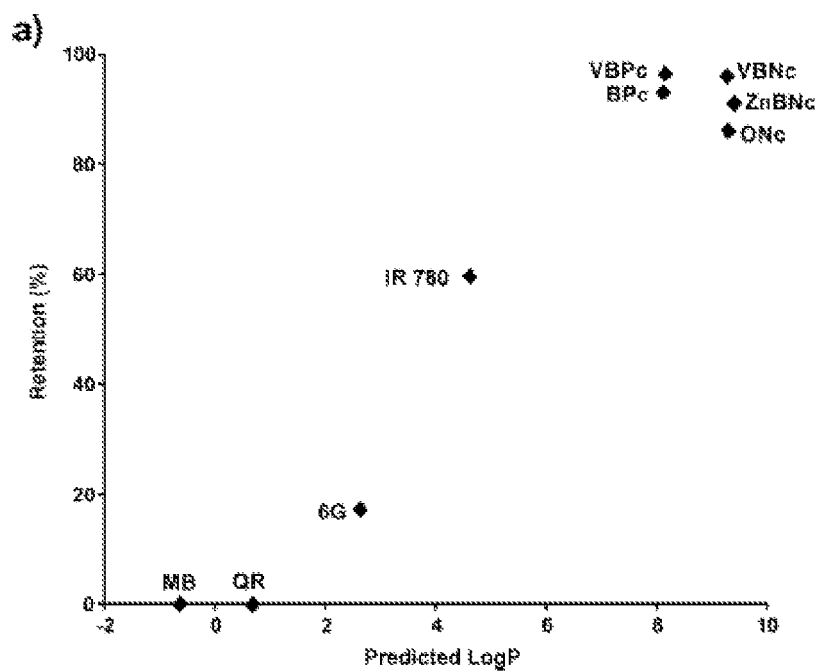
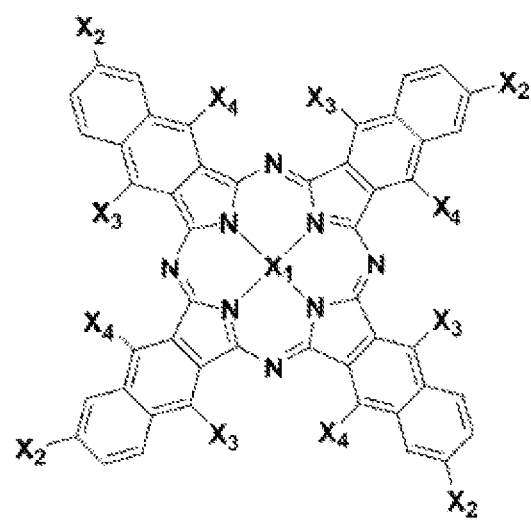

| | (Agent:surfactant) Molar ratio of final formulation | Typical agent concentration of final formulation (mg/ml) | Size (nm) | PDI | Log P | NaCl concentration (M) |
|---|---|---|---|---|---|---|
| 2,3,16,23-Tetra-tert-butyl-29H,31H-phthalocyanine | 5.4:1 | 19.2 | 18 | 0.15 | 8.15 | 0 |
| Zinc 2,11,20,29-tetra-tert-butyl-2,3-naphthalocyanine | 3.9:1 | 30 | 20 | 0.16 | 9.40 | 0 |
| 5,9,14,18,23,27,32,36-octabutoxy-2,3-naphthalocyanine | 3.2:1 | 13 | 20 | 0.16 | 9.29 | 0 |
| Ivermectin | 45.1:1 | 79.5 | 39 | 0.03 | 5.83 | 0 |
| Vitamin K1 | 39.5:1 | 150.0 | 74 | 0.25 | 8.48 | 0 |
| Retinal palmitate | 54.1:1 | 38.4 | 114 | 0.25 | 10.12 | 2 |
| Alpha-Tocopherol | 20.9:1 | 58.0 | 86 | 0.26 | 8.84 | 2 |
| Cholecalciferol | 9.2:1 | 75.7 | 45 | 0.16 | 7.98 | 2 |
| Ergocalciferol | 8.8:1 | 63.9 | 112 | 0.31 | 7.56 | 2 |
| Squalene | 43.9:1 | 80.2 | 81 | 0.28 | 8.64 | 3 |
| Cyclosporin A | 15.0:1 | 7.0 | 165 | 0.34 | 4.12 | 3 |
| Cabazitaxel | 7.8:1 | 41.0 | 62 | 0.10 | 3.69 | 3.5 |
| Testosterone Undecanoate | 9.3:1 | 16.0 | 112 | 0.19 | 8.73 | 4 |
| Coenzyme Q10 | 30:1 | 42.7 | 115 | 0.28 | 9.94 | 4 |

Figure 42

| | Pc nanonaps | ZnBNc nanonaps | BNc nanonaps | ONc nanonaps |
|---|---|---|---|---|
| Peak absorption in dichloromethane | 695 nm | 760 nm | 769 nm | 863 nm |
| Extinction coefficient of dye in dichloromethane | 193 ml·mg$^{-1}$·cm$^{-1}$ <br> 1.5×10$^5$ M$^{-1}$·cm$^{-1}$ | 100 ml·mg$^{-1}$·cm$^{-1}$ <br> 1.0×10$^5$ M$^{-1}$·cm$^{-1}$ | 138 ml·mg$^{-1}$·cm$^{-1}$ <br> 1.3×10$^5$ M$^{-1}$·cm$^{-1}$ | 172 ml·mg$^{-1}$·cm$^{-1}$ <br> 2.2×10$^5$ M$^{-1}$·cm$^{-1}$ |
| Peak absorption in aqueous nanonap form | 600 nm | 707 nm | 793 nm | 860 nm |
| Extinction coefficient of dye within aqueous nanonaps | 52 ml·mg$^{-1}$·cm$^{-1}$ <br> 3.8×10$^4$ M$^{-1}$·cm$^{-1}$ | 33 ml·mg$^{-1}$·cm$^{-1}$ <br> 3.3×10$^4$ M$^{-1}$·cm$^{-1}$ | 59 ml·mg$^{-1}$·cm$^{-1}$ <br> 5.5×10$^4$ M$^{-1}$·cm$^{-1}$ | 118 ml·mg$^{-1}$·cm$^{-1}$ <br> 1.5×10$^5$ M$^{-1}$·cm$^{-1}$ |
| Molar ratio of dye to F127 in nanonap | 5.4 | 3.9 | 0.2 | 3.2 |
| Molecular weight of nanonaps | 1.6×10$^8$ g·mol$^{-1}$ | 2.6×10$^8$ g·mol$^{-1}$ | 5.7×10$^8$ g·mol$^{-1}$ | 2.6×10$^8$ g·mol$^{-1}$ |
| Number of ONcs per nanonap | 526 | 621 | 106 | 501 |
| Number of F127 per nanonap | 98 | 158 | 488 | 155 |
| Nanonap extinction coefficient | 12.5 ml·mg$^{-1}$·cm$^{-1}$ <br> 2.0×10$^7$ M$^{-1}$·cm$^{-1}$ | 7.6 ml·mg$^{-1}$·cm$^{-1}$ <br> 2.0×10$^7$ M$^{-1}$·cm$^{-1}$ | 1.0 ml·mg$^{-1}$·cm$^{-1}$ <br> 5.8×10$^{10}$ M$^{-1}$·cm$^{-1}$ | 29.2 ml·mg$^{-1}$·cm$^{-1}$ <br> 7.6×10$^7$ M$^{-1}$·cm$^{-1}$ |
| Nanonap optical absorption cross section | 7.7×10$^{-16}$ m$^2$ | 7.6×10$^{-18}$ m$^2$ | 2.2×10$^{-18}$ m$^2$ | 2.9×10$^{-17}$ m$^2$ |

| | |
|---|---|
| 0.25 µg/mCi | 41.1 +/- 3.8% |
| 1 µg/mCi | 65.1 +/- 2.6% |
| 5 µg/mCi | 74.9 +/- 1.1 % |
| 25 µg/mCi | 73.0% +/- 1.9% |
| 100 µg/mCi | 80.5% |

SURFACTANT-STRIPPED MICELLE COMPOSITIONS WITH HIGH CARGO TO SURFACTANT RATIO

CROSS REFERENCE TO RELATED APPLICATIONS

This application claims priority to U.S. provisional patent application No. 62/020,249 filed on Jul. 2, 2014, and U.S. provisional application No. 62/020,233, filed on Jul. 2, 2014, the disclosures of which are incorporated herein by reference.

STATEMENT REGARDING FEDERALLY SPONSORED RESEARCH

This invention was made with government support under grant no. OD017898 awarded by the National Institutes of Health. The government has certain rights in the invention.

BACKGROUND OF THE DISCLOSURE

Encapsulation or sequestration of hydrophobic molecules for transport within biological systems has been a topic of wide interest and research. Hydrophobic drugs comprise a substantial proportion of all pharmaceutical compounds in use today. These drugs have limited solubility in water. For applications where precise dosing is required, oral delivery can lead to variable bioavailability. In some cases, parenteral administration is the preferred route. In some cases, hydrophobic drugs may be coaxed into aqueous solutions by changing the solution pH or by adding appropriate salts. In other cases, small amounts of solubilizing excipients such as dextrins or lipids are sufficient. However, for many compounds that are yet more difficult to dissolve, other excipient strategies are required. These frequently involve formulations formed from surfactants and non-aqueous solvents. Non-ionic surfactants such as Cremophor EL and Polysorbate-80 are commonly used for parental formulations, but can induce negative side-effects including anaphylactic hypersensitivity and neurotoxicity. Non-aqueous solvents have potential to cause hemolysis and in the case of oils, pulmonary microembolisms. For injectable formulations, neutral pH, isotonic solutions in water are preferred. New drug delivery systems that bypass these problems promise to give rise to next generation formulations and indeed have been gradually making their ways to the clinic. However, many drug delivery systems described to date are themselves formed with excipients in relatively large quantities that themselves may carry side effects as well as unknown long-term safety profiles. Thus, the mass or molar drug-to-excipient ratios of current nanoparticulate delivery systems may not be significantly better compared to surfactant solutions and typically are close to 1:10 mass ratio (drug:excipient). Clinical adoption of alternative drug delivery systems has been limited due to both formulation complexities and low drug-loading capacities.

Hydrophobic molecules are also often used as imaging agents. Imaging of the gastrointestinal tract is used in diagnostics. However, modalities based on X-ray radiation, magnetic resonance, and ultrasound suffer from limitations with respect to safety, accessibility or lack of adequate contrast. For example, functional intestinal imaging of dynamic gut processes has not been practical using existing approaches.

SUMMARY OF THE DISCLOSURE

The present disclosure is based on our observations that hydrophobic agents when contacted with surfactant such as a block-copolymer (e.g., poloxamer, such as those available under the trade name Pluronic®) self-assemble into micelles and that low-temperature processing enables removal of most or all of the poloxamer resulting in a composition where all or essentially all the remaining poloxamer molecules are present in surfactant-stripped hydrophobic agent-loaded micelles. This allows for micelle compositions with high hydrophobic agent concentrations and high hydrophobic agent-to-surfactant molar ratios.

Based on our studies, the present disclosure provides compositions and methods relating to micelle preparations that have been stripped of surfactant that is not part of the hydrophobic agent-loaded micelles. Hydrophobic agent is also referred to herein as hydrophobic cargo. In the compositions, substantially all of the surfactant (such as poloxamer) is present in the micelles and there is little or no free surfactant present. The disclosure also provides methods of preparing the compositions and methods of using the compositions.

The hydrophobic agent may be any hydrophobic molecule that is desired to be transported in a biological system. For example, the hydrophobic agent may be delivered to a desired site (for release at a site) or may be transported through a site without release (such as when used for imaging purposes). In one embodiment, the hydrophobic agent is a drug. In one embodiment, the hydrophobic agent is an optical imaging contrast agent. In various embodiments, the compositions comprise, consist essentially of, or consist of hydrophobic drug-loaded micelles and/or hydrophobic optical contrast dye-loaded micelles.

Low-temperature processing results in removal of substantially all of the unassociated poloxamer (poloxamer that is not associated with hydrophobic agent-loaded micelles when temperature is depressed). For example, 85% or more, 90% or more, 99% or more or 99.9% or more of the starting surfactant is removed. The remaining poloxamer is present in the micelles.

These compositions exhibit high stability and high loading. The hydrophobic agent:poloxamer molar ratio of the final composition is 3:1 or more. For example, where the hydrophobic agent is a drug, we observed hydrophobic agent:poloxamer molar ratios as high as 55:1, orders of magnitude greater than existing clinical formulations that use other solubilizing excipients, which are typically in the range of 1:10. In one example, where the hydrophobic agent is a drug, we observed a drug:poloxamer molar ratio of 7:1. In one embodiment, the present compositions have hydrophobic agent:poloxamer ratio of 60:1.

Surfactants suitable for making the present micelle compositions include block-copolymers (such as a poloxamer). In one embodiment, the micelles are formed by poloxamers as the only surfactant molecules and the micelles contain hydrophobic agents. In one embodiment, the surfactant is a block copolymer, the block co-polymer comprising at least a hydrophilic block and a hydrophobic block. In one embodiment, the block co-polymer is a tri block co-polymer such as a poloxamer. The compositions are substantially free of unassociated surfactant molecules. The term "unassociated surfactant molecules" or a corresponding term reciting a particular surfactant (such as "unassociated poloxamer molecules" or "unassociated poloxamer 127 molecules") is meant to indicate surfactant molecules that are not part of micelles once the temperature is depressed (such as below room temperature, for example. to 10° C. to −20° C.). Unassociated surfactant molecules may be surfactant molecules in unimeric form, loosely associated with each other (collectively "free" surfactant), or form empty micelles— i.e., micelles which have no hydrophobic agent molecules incorporated therein. Unassociated surfactant can be detected by separating the micelles from the much smaller unimeric surfactant by processes such as membrane filtration or dialysis and detecting the unassociated surfactant via standard analytical methods known in the art such as the colorimetric cobalt thiocyanate method for poloxamer detection.

These micelles can be prepared in solution for parental administration without other excipients. Alternatively, these micelles can be presented in a solution containing a pH buffer such as citrate or phosphate and ingredients to control tonicity such as saline or sucrose. The micelles can be stored in water or in a hypertonic saline solution containing up to 4 M NaCl. The hypertonic saline can be diluted prior to administration. The micelle compositions may be formulated with additional pharmaceutically acceptable carriers including sugars, starches, cetyl alcohol, cellulose, powdered tragacanth, malt, gelatin, talc, oils, glycols, glycerol monooleate, polyols, polyethylene glycol, ethyl alcohol, additional emulsifiers and the like.

The present disclosure also provides methods of making the unassociated-surfactant-stripped compositions. The method comprises contacting hydrophobic agent molecules dissolved in an organic solvent such as chloroform or methylene chloride or other organic solvents including, for example, ethanol, methanol, tetrahydrofuran and the like with surfactant molecules (such as poloxamer molecules) to form micelles, at least some of which have hydrophobic agent molecules incorporated therein. This is followed by evaporation or partial evaporation (active or passive) of the organic solvent and subsequent removal of surfactant molecules that are not involved in hydrophobic agent-loaded micelles. In one embodiment, the unassociated surfactant molecules are removed by lowering the temperature such that all or essentially all of the unassociated surfactant molecules become unimeric, followed by removal of the unimeric surfactant molecules (e.g., by a filtration process such as membrane filtration process). The low temperature processing can be repeated or continued as desired until all the detectable unassociated surfactant is removed. Because no more surfactant can be removed from the micelles, the micelles substantially lack unassociated surfactant molecules. The resulting composition comprises micelles that are referred to herein as surfactant-stripped induced "frozen" micelles ("ss-infroms"). The compositions may be used as such or may be concentrated. For example, the hydrophobic agent-loaded micelles can be concentrated to up to 150 mg/mL of agent.

In some cases, hydrophobic agent-loaded micelles may be formed using hypertonic salt solutions, vitamin E or Coenzyme Q10 co-loading, or using fatty esterification of the drug of interest to render it sufficiently hydrophobic. Vitamin E or Coenzyme Q10 co-loading involves incorporating those agents into the micelles in order to improve the stability or another loaded hydrophobic agent. The role of hypertonic saline is to make the solution outside the micelle more ionic, which has the effect of driving the hydrophobic molecules into the micelles.

The terms surfactant-stripped induced frozen micelles "ss-infroms", nanoparticles or micelles can be used interchangeably. In an embodiment, where the micelles are loaded with hydrophobic optical contrast agent dye, the ss-infroms are also referred to as nanonaps.

In one embodiment, the compositions of the present disclosure comprise a plurality of micelles with a size (referring to the diameter of the micelles) of 15 to 250 nm (and all integer nanometer values therebetween). In one embodiment, the size is 20-120 nm. In one embodiment, at least 80-90% (and all integer percentage values therebetween) of the micelles are within a range of 20-100 nm or 20-120 nm (and all integer nanometer values therebetween).

Depending on the hydrophobic cargo selection, these compositions are useful for various applications including, for example, drug delivery and imaging. Upon administration to mice, the micelle compositions of the present disclosure exhibited safety and efficacy in vivo.

In one embodiment, the present disclosure provides an aqueous composition comprising micelles, said micelles comprising poloxamer and incorporating therein a hydrophobic agent thereby forming hydrophobic agent loaded poloxamer micelles, wherein the hydrophobic agent:poloxamer molar ratio in the composition is at least 2:1 or 3:1 and wherein at least 90 or 95% of the poloxamer in the composition forms hydrophobic agent loaded micelles. In one embodiment, the only surfactant making up the micelles is one or more types of poloxamers (such as 407, 338, or 188; also known as Pluronic F127, F108 or F68 respectively and referred to herein as F127, F108 or F68 respectively) and the micelles have incorporated therein hydrophobic agents as cargo. The poloxamer may be a single type of poloxamer or may be more than one type of poloxamer. In one embodiment, at least 96, 97, 98 or 99% of the poloxamer molecules in the formulation are present as micelles which have incorporated therein hydrophobic agent as cargo. Poloxamer incorporation in the micelles may be quantified by lowering the temperature to −20 to 10 C, which causes unassociated poloxamer to become unimeric, separating the hydrophobic agent-loaded micelles via membrane separation techniques and quantifying the amount of unassociated poloxamer. When the hydrophobic agent is a drug, such as a therapeutic drug, the drug:poloxamer molar ratio may be from 7:1 to 55:1 or 7:1 to 60:1. When the hydrophobic agent cargo is an imaging contrast dye, the dye:poloxamer molar ratio may be from 3:1 to 10:1. In one embodiment, the hydrophobic agent is characterized as having octanol-water partition coefficient (Log P value) of at least 3, or from 3 to 11.

The present disclosure provides a method of making the present compositions comprising: contacting hydrophobic agent (such as x moles) dissolved in organic solvent with an aqueous solution of poloxamer (such as y moles) thereby forming hydrophobic agent loaded poloxamer micelles; causing poloxamer molecules which are not forming hydrophobic agent loaded micelles to become unitary poloxamer units. X and y may be selected as desired. In one embodiment, the ratio of x:y is 0.1:1 to 2:1. Formation of unitary poloxamer molecules may be induced by subjecting the composition to a temperature at or below the CMT of the poloxamer. In various embodiments, the depressed temperature is from 0° C. to 25° C.; 0° C. to 20° C.; 0° C. to 15° C., 0° C. to 10° C., or for hypertonic saline solutions −20° C. to 0° C. and removing the unitary poloxamer units to result in poloxamer stripped hydrophobic agent-loaded micelle compositions, where at least 85% of the starting amount of poloxamer molecules are removed, the hydrophobic agent: poloxamer molar ratio is from 3:1 to 55:1, and 90% or more (such as 95, 86, 97, 98 or 99% or 99.5, 99.9 or 100%) poloxamer in the composition is present in hydrophobic agent-loaded micelles. The compositions may be used fresh or stored for later use. The compositions may be stored as powdered or freeze-dried form and may later be reconstituted with aqueous medium.

The present disclosure also provides a method of drug delivery comprising: preparing a hydrophobic drug loaded micelle composition as described herein which is substantially free of unassociated poloxamer (i.e., at least 90% of the poloxamer is present as hydrophobic cargo loaded micelles) and administering the composition to an individual such that it is transported to the desired location. In one embodiment, the present disclosure provides a method of imaging (such as the gastrointestinal tract) comprising: preparing a hydrophobic contrast dye-loaded micelle composition as described herein which is substantially free of un-associated poloxamer (i.e., at least 90% of the poloxamer is present as hydrophobic dye-loaded micelles), administering the composition to an individual such that it is transported to and through the GI tract, and imaging the GI tract as the composition is being transported through the tract. Imaging may be performed immediately after administration and may continue over a desired period of time or it may be initiated after a certain time after administration. For drug delivery purposes, as an example, the composition may be administered by intravenous, intraperitoneal, intramuscular, topical, subcutaneous or mucosal delivery. For imaging purposes such as imaging of GI tract the compositions may be administered by oral route and for other imaging purposes the compositions may be administered by intravenous, intratumoral, intraperitoneal, subcutaneous, intradermal or intramuscular delivery.

BRIEF DESCRIPTION OF THE FIGURES

solution of F127. Following organic solvent evaporation, the solution was subjected to low-temperature centrifugal filtration washes and the amount of drug and F127 in the retentate was determined. b) Absorption spectrum of retinol ss-infroms

FIG. 22: a) Salt enhances the yield of cabazitaxel informs, b) Coenzyme Q10 improved the stability of CTX infroms upon dilution, c) CTX ss-infroms exhibited higher molar ratio compared to clinical formulations, d) CTX loaded surfactant stripped micelles effectively cured subcutaneous MIA Paca-2 tumors in nude mice with two intravenous injections of 30 mg/kg on day 0 and day 4 (marked by arrow).

FIG. 23: Formation of non-exchangeable F127-naphthalocyanine frozen micelles. a) Retention of dyes of varying hydrophobicity added to an aqueous solution of 10% (w/v) F127 and then dialyzed against 20 mM cholate for 24 hours. MB=Methylene blue, QR=Quinaldine Red, 6G=Rhodamine 6G, IR780=IR780 iodide. b) Chemical structure of napthalocyanines used. BNc: X1=2H; X2=t-Bu; X3, X4=H. VBNc: X1=V=O; X2=t-Bu; X3, X4=H. ZnBNc: X1=Zn; X2=t-Bu; X3, X4=H; ONc: X1=2H; X2=H; X3, X4=O—(CH2)3CH3. Phthalocyanines lack outer benzenes: BPc: X1=2H; X2=t-Bu; X3, X4=H. VBPc: X1=V=O; X2=t-Bu; X3=N(CH3)2, X4=H.

FIG. 42: Table representing properties of ss-infroms formed with exemplary hydrophobic agents. Log P refers to the properties of the hydrophobic of the agent predicted via the ALog Ps algorithm. Size and PDI (polydispersity index) of final formulation were assessed with dynamic light scattering.

FIG. 43: Table showing Nanonap optical parameters

FIG. 44: Table showing Labelling of nanonaps with $^{64}$Cu: Radiolabelling yield using different amount of nanonaps per mCi of $^{64}$Cu. Data represent mean±SD. for triplicate experiments except at the largest dose which was a single experiment.

DETAILED DESCRIPTION OF THE DISCLOSURE

Figure 1:
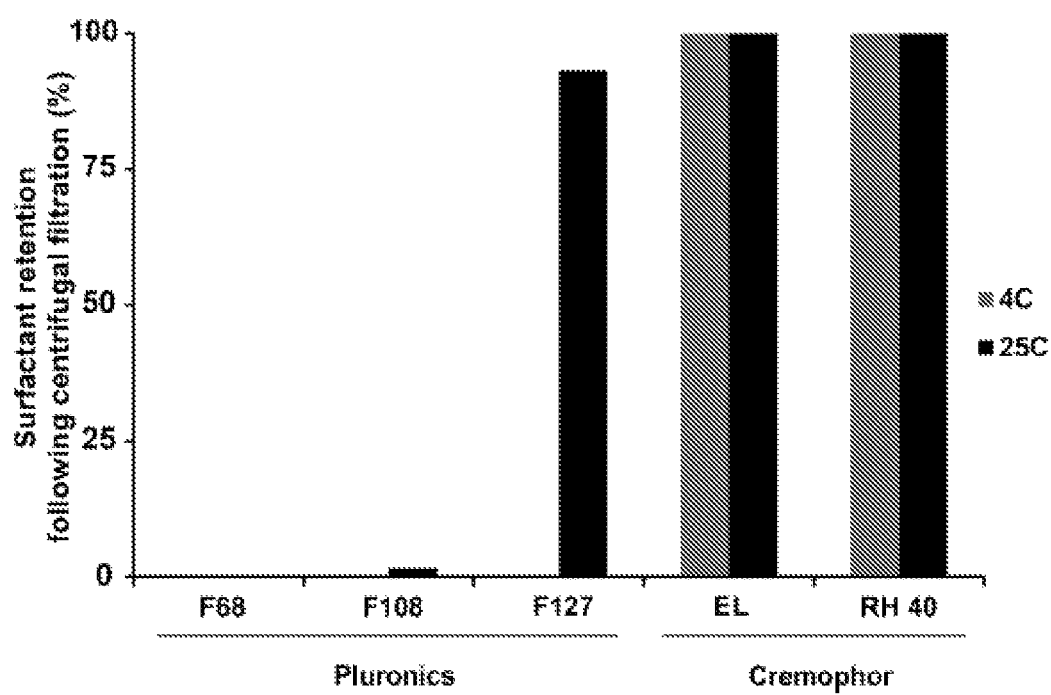
FIG. 1: Surfactant retention following washing with centrifugal filtration. 10% (w/v) solutions of surfactants were spun at the indicated temperature and surfactant in the retentate was assessed using the 1,6-Diphenyl-1,3,5-Hexatriene fluorescence method and a standard curve.

The present disclosure provides compositions and methods for transport of hydrophobic agent molecules in biological systems. The compositions comprise hydrophobic agent-loaded micelles (also referred to herein as nanoparticles). The nanoparticles are made up of surfactant molecules (such as a poloxamer) and have incorporated therein hydrophobic agents. The nanoparticles may be present in a carrier, such as an aqueous carrier. The term "incorporated" as used herein means that the hydrophobic agent resides in the hydrophobic domain of a micelle.

In one embodiment, the present disclosure provides compositions and methods for delivery of hydrophobic drugs. The term "drug" as used herein means any agent that is delivered for the purposes of therapeutics, diagnostics or monitoring of physiological functions. In one embodiment, the present disclosure provides compositions and methods for transport of hydrophobic contrast agents.

In one embodiment, the present disclosure provides compositions comprising a plurality of hydrophobic agent-loaded micelles in a powdered form. The micelles may be freeze-dried. The compositions are substantially or completely free of un-associated surfactant. For example, the compositions are substantially or completely free of un-associated poloxamer.

In one embodiment, 85% or more of the starting amount of surfactant making up the micelles (e.g., poloxamer) is removed from the compositions. The remaining poloxamer forms micelles, which are loaded with hydrophobic agents. In various embodiments, up to 90, 95, 99 or 99.9% of the starting amount of poloxamer is removed from the composition.

In one embodiment, the present disclosure provides micelles comprising one or more poloxamers and one or more types of hydrophobic agents (such as drug or contrast dye) molecules. The micelles may be in freeze-dried form. The freeze dried compositions are substantially free of any un-associated surfactant (i.e., surfactant that is unimeric or can be rendered unimeric upon low temperature treatment, e.g., empty micelles or any poloxamer in unimeric form or where the unimers are loosely associated with each other, but without having drug molecules being incorporated therein).

The micelles contain hydrophobic agents that may be densely packed, but are not crystallized. Due to the low surfactant content, the micelles can readily be further concentrated by, for example, filtration, such as membrane filtration. The remaining surfactant of hydrophobic agent-loaded micelle compositions is not a dispersant, but rather forms the micelles.

In one embodiment, the composition contains micelles in a suitable buffer such as a sugar solution or saline solution with or without a pH buffer such as citrate, phosphate, histidine or glutamate and is substantially free of unassociated poloxamer molecules.

The surfactant molecules of the present disclosure are able to solubilize the hydrophobic drugs and a drug-surfactant complex is able to form micelles. In one embodiment, the surfactant useful for the present disclosure is a block-copolymer comprising at least a hydrophobic and a hydrophilic block. In one embodiment, the surfactant is a tri-block copolymer such as a poloxamer. Poloxamers are polyethylene oxide (PEO)-polypropylene oxide (PPO)-polyethylene oxide tri-block co-polymers of different molecular weights. For example, poloxamers are composed of a middle hydrophobic chain of polypropylene (poly(propylene oxide)) flanked by two hydrophilic chains of polyoxyethylene (poly(ethylene oxide)). Poloxamers are commercially available—such as under the trade name Pluronic®. Many poloxamers are known in the art including poloxamers F87, F88, F98, F108, F127 and the like.

In one embodiment, the present composition comprises micelles comprising a surfactant selected from poloxamers F127, F68, F108 and combinations thereof, and one or more hydrophobic agents. In one embodiment, the only surfactant present in the micelles is a poloxamer. In one embodiment, the only surfactant in the micelles is F127, F68 and/or F108. In one embodiment, no other surfactant is present in the composition comprising micelles comprising, consisting essentially of, or consisting of, a poloxamer surfactant and having hydrophobic cargo molecules incorporated therein.

The drugs of the present disclosure may be any hydrophobic molecules that are desirable for administration to an individual for the purposes of diagnosing or monitoring of physiological functions or improving, treating, preventing, diagnosing or monitoring pathological conditions. Thus, both therapeutic and non-therapeutic hydrophobic agents may be delivered by this method.

The drugs or contrast dyes useful in the present disclosure are generally hydrophobic. In one embodiment, the octanol-water partition coefficient (such as Log P values, predicted with the ALOG PS algorithms) is at least 2. In one embodiment, the octanol-water partition coefficient is from 2 to 11. In one embodiment, the octanol-water partition coefficient is from 3 to 11. In various embodiments, it is 3, 4, 5, 6, 7, 8, 9, 10 and 11.

In certain embodiments the hydrophobic drug is Alpha-Tocopherol, Abafungin, Amiodarone, Azithromycin Dihydrate, Bepridil, Beta-carotene, Budesonide, Cabazitaxel, Carbamazepine, Calciferol, Carvedilol, Chloroquine, Chlorpromazine, Cholecalciferol, Clotrimazole, Coenzyme Q10, Cotinine, Cyclizine, Cyclosporine A, Diazepam, Docetaxel, Econazole, Ergocalciferol, Etoposide, Fentanyl, Fenofibrate, Finasteride, Fulvestrant, Haloperidol, Haloperidol decanoate, Itraconazole, Ivermectin, Labetalol, Latanoprost, Meloxicam, Miconazole, Mifepristone, Mycophenolate mofetil, Nimodipine, Phenytoin, Piroxicam, Pregnenolone, Pregnenolone Acetate, Progesterone, Propofol, Reserpine, Retinol, Retinol Palmitate, Sertaconazole, Sibutramine, Simvastin, Sirolimus, Squalene, Tacrolimus, Tamoxifen, Temsirolimus, Testosterone, Testosterone cypionate, Testosterone priopionate, Testosterone undecanoate, Tipranavir, Travoprost, Triamcinolone, Vitamin K1, Paclitaxel and combinations thereof.

In certain embodiments, the hydrophobic agent is a contrast dye, such as a chromophore. The chromophore useful for the present disclosure may be any hydrophobic contrast agents suitable for imaging. Examples of suitable chromophores include tetopyrroles and analogs and derivatives thereof, including porphyrins and derivatives thereof, chlorins and derivatives thereof (including chlorophyll A, pheophytin A and related compounds), phthalocyanines and derivatives thereof, naphthalocyanine and derivatives thereof, bacteriochlorins and derivatives thereof, bacteriochlorophylls and derivatives thereof. The characteristics of a suitable chromophore are: high optical absorption in an area of the spectrum suitable for biological in vivo imaging. This usually consist of near infrared absorption in the range of 600-1000 nm In one embodiment, the dyes are phthalocyanine or naphthalocyamine derivatives. Suitable dyes include, but are not limited to, 2,11,20,29-tetra-tert-butyl-2, 3-naphthalocyanine (BNc), Zinc-2,11,20,29-tetra-tert-butyl-2,3-naphthalocyanine (ZnBNc), 5,9,14,18,23,27,32,36-Octabutoxy-2,3-naphthalocyanine (ONc), Nickel-5,9,14,18,23, 27,32,36-Octabutoxy-2,3-naphthalocyanine (NiONc), Vanadyl 2,11,20,29-tetra-tert-butyl-2,3-naphthalocyanine (VBNc), 2,9,16,23-tetra-tert-butyl-29H,31H-phthalocyanine (BPc), Vanadyl 3,10,17,24-tetra-tert-butyl-1,8,15,22-tetrakis(dimethylamino)-29H,31H-phthalocyanine (VBPc). Derivatives and analogs of the dyes are also included which are characterized by tetraphyrrole structure and hydrophobicity such that the octanol-water partition coefficient (as determined by measurement or by prediction by the ALOG PS algorithm) is at least 2.

The starting molar ratio of the hydrophobic agent to the poloxamer can range from 0.02:1 to 3:1, and following the process of preparing the micelle compositions as described herein, the hydrophobic agent:poloxamer ratio can be as high as 55:1. In one embodiment, the hydrophobic agent is a drug and the starting drug:poloxamer molar ratio is 0.1:1 to 3:1 and the final molar ratio is 7:1 to 55:1. In one embodiment, the hydrophobic agent is an optical contrast dye and the starting dye:poloxamer molar ratio is 0.02:1 to 1:1, while the final molar ratio is 3:1 to 10:1.

In one embodiment, the composition comprises micelles comprising a drug and surfactant molecules and is substantially free of unassociated surfactant molecules. In one embodiment, all (or substantially all) the hydrophobic agent molecules are present as incorporated in poloxamer micelles and there are no (or less than 1%) hydrophobic agent molecules that are not incorporated in the micelles. In various embodiments, there is less than 0.5% or 0.1% (and all percentage values to the tenth decimal point therebetween) hydrophobic agent molecules that are not incorporated in the micelles. Thus, the composition has micelles which have hydrophobic agent molecules incorporated therein, but is substantially lacking micelles which are empty, i.e., do not have hydrophobic agent molecules incorporated therein or unimeric or loosely associated surfactant molecules. In one embodiment, the composition of the present disclosure comprises at least 90% of all surfactant molecules present in micelles having incorporated therein hydrophobic agent molecules. In various embodiments, the composition comprises at least 91, 92, 93, 94, 95, 96, 97, 98, 99% of the surfactant molecules in micelles having incorporated therein hydrophobic agent molecules. In one embodiment, the composition comprises 100% of the surfactant molecules in micelles having hydrophobic agent molecules incorporated therein so that no detectable unassociated surfactant molecules are present. Thus, the various embodiments provide a composition in which 10% or less of the total surfactant molecules present are not associated with hydrophobic agent-loaded micelles. In various embodiments, the composition has 9% or less, 8% or less, 7% or less, 6% or less, 5% or less, 4% or less, 3% or less, 2% or less, 1% or less, or less than 1% of the total surfactant molecules not associated with hydrophobic agent-loaded micelles.

The present compositions may also contain suitable amounts of other components such as salt (NaCl, KCl, or other salts), sugars, pH buffers and the like including any other components used in formulations for administration to individuals. For example, the salt concentration can be up to 4M.

The present micelle compositions are well dispersed and there is no appreciable aggregation of the micelles. In one embodiment, there is no detectable aggregation as detected by sub-micron filtration techniques and/or dynamic light scattering techniques and/or by visual inspection by eye (apparent as a cloudy appearance). In one embodiment, the composition comprises nanoparticles that are highly uniform and are monodisperse (dynamic light scattering polydispersity index of less than 0.5 based on dynamic light scattering). In one embodiment, the polydispersity index is from 0.05 to 0.5. In various embodiment, the nanoparticles have a polydispersity index of 0.4 or less, 0.35 or less, 0.3 or less, 0.2 or less, 0.1 or less or 0.05 or less. In various embodiment, the nanoparticles have a polydispersity index of 0.4 to 0.05, 0.35 to 0.05, 0.3 to 0.05, 0.2 to 0.05, or 0.1 to 0.05.

The compositions of the present disclosure have high hydrophobic agent:surfactant molar ratio. In one embodiment, the ratio is from 0.5:1 to 50:1 (and all ratios and ranges therebetween). In one embodiment, the ratio is from 1:1 to 55:1. For example, the ratio is 1:1, 10:1, 15:1, 20:1, 25:1, 30:1, 35:1, 40:1, 45:1, 50:1, or 55:1. In embodiments, the ratio is from 3:1 to 10:1, 10:1 to 50:1, 10:1 to 55:1, 10:1 to 60:1 (and all ratios therebetween). In one embodiment, the hydrophobic agent is a drug and the drug:poloxamer molar ratio in the composition is at least 10:1 and can be up to 50:1, up to 55:1, or up to 60:1 (and all ratios therebetween). For example, in embodiments, the drug:poloxamer ratio is 10:1, 15:1, 20:1, 25:1, 30:1, 35:1, 40:1, 45:1, 50:1, 55:1, or 60:1. In one embodiment, the hydrophobic agent is a contrast agent (dye) and the dye:poloxamer molar ratio in the composition is at least 3:1 and can be up to 10:1 (and all ratios therebetween). For example, the dye:poloxamer ratio is 3:1, 3.5:1, 4:1, 4.5:1, 5:1, 5.5:1, 6:1, 6.5:1, 7:1, 7.5:1, 8:1, 8.5:1, 9:1, 9.5:1 or 10:1.

The micelles have a size (diameter) between 10 to 250 nm. In one embodiment, the micelles have a size of 15 to 250 nm (and all integers nanometers therebetween). In one embodiment, at least 90% of the micelles are within a 15-250 or 15-100 nm range. In one embodiment, the average size is from 20-100 nm diameter. In one embodiment, the average size is 20-120 nm. In various embodiments, it is 20, 30, 40, and 50, 60, 70, 80, 90, 100, 110, or 120 nm. In one embodiment, at least 80-90% (and all integer percentage values therebetween) of the micelles are within a range of 20-100 nm (and all integer nanometers values therebetween). In one embodiment, at least 80-90% (and all integer percentage values therebetween) of the micelles are within a range of 20-120 nm (and all integer nanometer values therebetween). In an embodiment, more than 90% of the micelles are within a 20-100 nm range or in the range of 20-120 nm. In an embodiment, 91, 92, 93, 94, 95, 96, 97, 98, 99 or 100% of the micelles are within a 20-100 nm range or within a 20-120 nm range.

In one embodiment, the compositions of the present disclosure are used for imaging applications and comprise a plurality of frozen micelles with an average size of 15 to 40 nm (and all integers nanometers therebetween). In one embodiment, the average size is from 20-30 nm (diameter). In various embodiments, it is 20, 21, 22, 23, 24, 25, 26, 27, 28, 29, or 30 nm. In one embodiment, at least 80-90% (and all integer percentage values therebetween) of the micelles are within a range of 20-30 nm (and all integer nanometer values therebetween). In an embodiment, more than 90% of the micelles are within a 20-30 nm range. In an embodiment, 91, 92, 93, 94, 95, 96, 97, 98, 99 or 100% of the micelles are within a 20-30 nm range. In another embodiment, at least 90% of the micelles are within a 15-40 nm range.

The compositions may be prepared as follows. A hydrophobic agent is dissolved in an organic solvent, e.g., at agent concentrations from 10 mg/mL to 200 mg/L and added to an aqueous poloxamer solution e.g., 5, 10 or 15% w/v poloxamer, and the organic solvent is allowed to evaporate (active or passive means). Larger aggregates, if any, are removed by filtration or centrifugation. Unincorporated poloxamer (i.e., poloxamer that is not associated with the hydrophobic agent molecules) is removed. In one embodiment, the removal is facilitated by changing the conditions such that surfactant forming empty micelles or that is loosely or peripherally associated with the micelles changes to monomers (unimeric form). When this is done, the empty micelles or loosely associated surfactant becomes unimeric and then become easier to remove. In one embodiment, this is achieved via critical micelle concentration (CMC) switching—i.e., by lowering the temperature to or below the CMT so that the micelles change into unimeric form. In one embodiment, the temperature at which the unimeric forms are formed can be anywhere from 30° C. to 0° C. (and all temperature values therebetween to the tenth decimal place). In one embodiment, the depressed temperature is from room temperature (25° C.) to 0° C. In one embodiment, the depressed temperature is from 25° C. to 1 C or 22° C. to 1° C. In one embodiment, the depressed temperature is from 20° C. to 1° C. (and all temperature values therebetween to the tenth decimal place). In one embodiment, the depressed temperature is from 10° C. to −20° C. (and all temperature values therebetween to the tenth decimal place). In one embodiment, it is not be necessary to lower the temperature and the transformation from empty micelles to monomers may be achieved by other means by using other solvents or salt conditions.). In one embodiment, the depressed temperature is from 0° C. to −20° C. (and all temperature values there between to the tenth decimal place).

In one embodiment, for example, the clarified solution (obtained after the hydrophobic agent (in a solvent) had been added to the aqueous poloxamer, and the solvent allowed to evaporate) is cooled on ice and subjected to centrifugal filtration using speeds resulting in from 500 to 5000 g for times typically 10 to 100 minutes at 4° C. until a significant volume of solution (such as 100 to 1000 uL) is retained. The centrifugal force used for the filtrations may be 2,000 g or higher. For example the centrifugal force may be 2,000 g to 4,000 g. The centrifugation may be carried out at from 1° C. to room temperature, or from 1° C. to 10° C. or 4° C. to 10° C. In one embodiment, it is done at 1 to 10° C. at 3,500 g for 25 mins Water can be added back to the concentrate. The retentate is subjected to one or more washings and centrifugal filtration. Thus, washing and filtration can be repeated as desired. In one embodiment, washing and filtration procedure is repeated 2 to 8 times (and all integers therebetween). In one embodiment, it is repeated 3 times. In another embodiment, the washing is done in a continuous manner using diafiltration instead of discrete steps. In one embodiment, the washing and filtration procedure is such that at least 60% of the surfactant used initially to make the formulation is removed by washing. In various embodiments, at least 70%, at least 80%, at least 85%, at least 90%, at least 95%, at least 99%, and all of the unassociated surfactant is removed. Whether the desired amount of surfactant is removed or not can be checked by determining the surfactant coming out in the washings. In one embodiment, the composition is subjected to washes until no detectable surfactant is found in the washing (or filtrate). For example, we observed that generally after three or four washings there was no detectable surfactant in further washings. Surfactant can be detected with standard methods such as the colorimetric cobalt thiocyanate method.

The physical and optical properties of the compositions can be determined by standard techniques. Particle size measurements and uniformity may also be determined by standard techniques such as transmission electron microscopy, and the like. Stability can be assessed by dialysis against relevant fluids.

In one embodiment, one or more co-loading agents (e.g., a hydrophobic molecule, such as Vitamin E and/or Coenzyme Q) are used with the drug to prepare the micelles. It was observed that using Vitamin E to co-load the drug resulted in a synergistic increase in drug loading in the micelles. In one embodiment, Paclitaxel was used with Vitamin E or Coenzyme Q to form the micelles. In one embodiment, Docetaxel was used with Vitamin E to form the micelles. The molar ratio of co-loading agent relative to the drug of interest can range from 0.1:1 to 10:1.

The present compositions may be used fresh or may be stored as aqueous solution refrigerated or at room temperature or at any temperatures therebetween (such as from 25° C. to 0° C.). The compositions may also be freeze dried and stored dry. Thus the compositions may be stored and then reconstituted in more concentrated forms than available for previous compositions.

If a hydrophobic phthalocyanine or naphthalocyanine is used as a hydrophobic agent, the resulting solutions can be concentrated to have near infrared absorbances at least as high as 500 absorbance units. In one embodiment, the nanoparticles may be detectably labeled. For example, the nanoparticles are radiolabeled or magnetically labeled by forming metal complexes with the hydrophobic agents such as within the macrocycles of a dye. In one embodiment, the nanoparticles are labeled with $^{64}$Cu. They may be labeled with Mn for MRI detection.

For using the present compositions, administered can be carried out by any suitable route of administration. For example, the compositions may be administered orally, intravenous, intradermal, intramuscular, mucosal, intratumoral, topically, or any other way of administration.

The compositions can be used for imaging techniques such as optical imaging (including photoacoustic imaging and fluorescence imaging), as well as whole body techniques such as positron emission tomography (PET) imaging, magnetic resonance imaging (MRI) and the like. We observed that when dye loaded micelles were used for imaging, the micelles could withstand the harsh conditions of the stomach and intestinal milieu, avoid systemic absorption, and give rise to good optical contrast for photoacoustic imaging. The dye-loaded micelles for the imaging application are referred to herein as nanonaps.

In one embodiment, the micelles have tunable and large near-infrared absorption values (>1000). For example, the absorbance is 500 to 1000 times greater than what is seen with traditional liposomal formulations made with the same dye. In some embodiments, the nanoparticles have peak emission from about 650 to about 1000 nm.

Unlike conventional chromophores, nanonaps exhibited non-shifting spectra at ultrahigh optical densities and, following oral administration in mice, passed safely through the gastrointestinal tract. In one embodiment, non-invasive, non-ionizing photoacoustic techniques can be used to visualize nanonap intestinal distribution with low background and resolution with 0.5 cm depth. Deeper imaging may be carried out by improved PAT technology. This allows real-time intestinal functional imaging with ultrasound co-registration. In one embodiment, other imaging techniques, such as Positron emission tomography can be used. This disclosure provides data for PET using radiolabeled nanonaps allowing complementary whole body imaging.

For use in imaging, the present compositions are administered orally to an individual or otherwise delivered to the GI tract. The individual may be a human or a non-human animal. In preclinical studies, we have given doses of 100 ODs and this results in strong signal detection by photoacoustic imaging. High resolution scanning may be carried out as well as real time imaging. For example, the movement of nanonaps in the digestive system can be monitored after gavage of 100 ODs of the composition. The term OD stands for "optical density" and is a volume independent measure of absorbance ("ODs"—one OD is defined as the amount of nanoparticles required to produce absorbance of 1 in a 1 mL solution measured with a standard 1 cm path length). This allows evaluation of regions of interest and also analysis of peristalsis, intestinal obstruction, and the like. Additionally, imaging techniques, like PET scanning, may be carried out by using radiolabeled nanoparticles (such as nanoparticles labelled $^{64}Cu$). Image reconstruction can then be carried out.

Photoacoustic (PA) imaging is a non-ionizing modality with deeper penetration than other optical methods. Instrumentation costs are low and the systems are small and modular with potential to become widely accessible for routine clinical probing of chronic and acute GI conditions. PA imaging is a data-rich, inherently real-time modality suitable for imaging dynamic intestinal processes such as peristalsis and segmentation without spatial resolution sacrifice. Additionally, PA imaging is a safe, non-invasive and non-ionizing modality, which matches the preferred characteristics of GI imaging, especially in the case of pediatric patients. PA techniques are particularly useful for imaging exogenous near-infrared (NIR, 650-1000 nm) contrast agents. The present compositions are useful for this modality since they exhibit negligible systemic absorption into the body. This is important since the subsequent loss of contrast agent from the intestine would lead to signal reduction, interfere with quantitative measurements and introduce toxicity concerns. The nanoparticles of the present composition also do not degrade in the harsh chemical and digestive environments of the stomach and intestine.

The present composition may be administered by other routes including, intravenous, intramuscular, intradermal, or any other route to reach the area of interest. The present compositions may also be used for imaging of other organs and systems. For example, the compositions can be used for imaging lymphatic system, either in a localized area or more generally, and also for imaging blood vasculature following intravenous administration. For imaging the lymph nodes, it may be injected into the lymphatic system. Imaging of these systems can be done in an analogous manner to the description provided for imaging the GI tract.

The following examples are presented to illustrate the present invention. They are not intended to limiting in any manner.

EXAMPLE 1

This example describes the preparation of micelles and their characteristics. Materials were obtained from Sigma unless otherwise indicated.

Materials and Methods

Pluronic F127 (sigma, P2443), Pluronic F68 (sigma, 412325), Cremophor EL (sigma, C5135), Cremophor RH 40 (Sigma, 07076), methylene chloride (Fisher), phylloquinone (vitamin K1, VWR, AAAL10575-03), Cyclosporine a (VWR, 89156-334), 2,6-Diisopropylphenol (propofol, VWR, AAAL06841-14), Fulvestrant (Biorbyt, orb62178), Amiodarone Hydrochloride (VWR, AAJ60456-03), Ivermectin (VWR, AAJ62777-03), Testosterone Undecanote (Matrix, 099258), Cholecalciferol (VWR, TCC0314), Retinol Palmitate (VWR, IC15652125), Temsirolimus (LC labs, T-8040), Mifopristone (VWR, TCM1732), Retinol (Kracker, 45-T3634), Coenzyme Q10 (Kracker, 45-C9538), Docetaxel (LC labs, D-1000), Paclitaxel (LC labs, P-9600), Cabazitaxel (Proactive Molecular Research), squalene (Sigma) and 5,9,14,18,23,27,32,36-Octabutoxy-2,3-naphthalocyanine (ONc, from Sigma), 2,11,20,29-Tetra-tert-butyl-2,3-naphthalocyanine (BNc from Sigma); 2,9,16,23-Tetra-tert-butyl-29H,31H-phthalocyanine, Zinc 2,11,20,29-tetra-tert-butyl-2,3-naphthalocyanine (Zn-BNc from Sigma).

The surfactant retention experiment (FIG. 1) was carried out by spinning 4 ml 10% (w/v) pluronic or cremophor aqueous solution and then placing the solution in centrifugal filtration tubes (Fisher # UFC810024) and spinning at 4° C. or 25° C. at 3,500 g for 25 mins. After adding water back to retentate to 4 mL, the solutions were subjected to a second centrifugation at 3,500 g for 10 mins. Distilled water was added to the final retentates to 4 ml and pluronic and cremophor concentrations were determined by colorimetric and 1,6 Diphenyl-1,3,5-hexatriene (DPH) probe method, respectively. Specifically, pluronic concentration was determined by a cobalt thiocyanate reagent, which was prepared first by dissolving 0.3 g cobalt nitrate hexahydrate and 1.2 g ammonium thiocyanate in 3 mL water. Then 100 μL cobalt thiocyanate solution, 40 μL F127 solution in the concentration range of 0-7.5 wt % (more concentrated F127 solutions were diluted to fit the range), 200 μL ethyl acetate and 80 μL ethanol were combined. The mixture was vortexed gently and centrifuged at 14000×g for 1 min. The blue supernatant was removed and the blue pellet was washed using ethyl ether several (~5) times until the supernatant became colourless. The pellet was then dissolved in 1 mL acetone to measure the absorbance at 623 nm. As of DPH probe method, 50 μl of 0.4 mM DPH in methanol stock solution was added into 1 ml of cremophor solution with concentration of 0-1% (wt). After sitting in the dark to equilibrate for at least 3 h, UV-vis absorption intensity at 356 nm was recorded.

Drug absorbance retained experiment (FIG. 2) was started with ONc drug dissolved surfactant solution formation. In brief, 2 ml of ONc dissolved DCM solution (concentration: 0.4 mg ONc/ml DCM) was added drop wise into 6 ml of 10% pluronic or cremophor aqueous solutions. After stirring for at lease 4 h to allow DCM to evaporate, the obtained solutions were spun at 3,500 g for 10 mins and then 1 ml of the supernatants were subjected to low temperature centrifugation at 3,500 g for 15 mins, triplicate; before each centrifugation, distilled water was added to starting solution or concentrate, the volume being 4 ml. UV-vis Absorption was measured at ~863 nm.

Drug infroms formation started with the solubilization of hydrophobic drugs into F127 solutions. 100 ul of stock solution (50 mg drug/ml DCM) (for taxane drug co-loading experiments, the indicated amounts of vitamin E or Co Q10 were dissolved in stock solution along with taxane drug) was added drop wise into 1 ml of 10% (w/v) F127 solution (10% F127 solution with 0.5, 1, 2, 3 M NaCl or KCl for cyclosporine a, water or 10% F127 with 0.15, 0.5, 1M NaCl for propofol and amiodarone) with stirring for 3 hours. Then the resulting solutions were subjected to several low temperature centrifugation washes. For large-scale infroms formation, 30 mg drug was dissolved in 150 ml DCM and the resulting solution was added drop wise into 750 ml of 10% (w/v) F127/F68 solutions. Instead, the excess F127/F68 was removed by diafiltration method using single module Viva flow 200 (Sartorius). Absorbance was measured on Perkin Elmer XLS using Quatz cuvette with 1 cm path lengths. Size was measured on Nano Brook 90 Plus PALS machine. For the qualification of O.D. retained in co-loading experiments, vitamin E and Co Q10 alone (without drug) infroms control was made in parallel and the absorbance at characteristic peaks of drugs were subtracted. For the molar ratio determination, concentrated infroms were lyophilized. Then the mass of infroms powder was determined and the powder was dissolved in dichloromethane to the determine mass of drug. The mass of F127 or F68 was determined based on the difference in total lyophilized mass.

Figure 2:
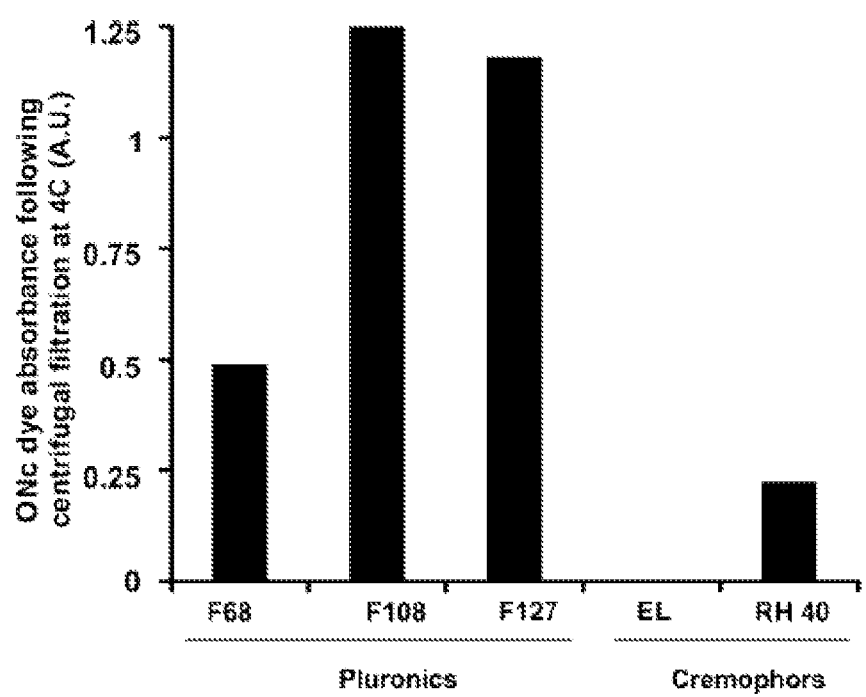
FIG. 2: Dye absorbance of retained and solubilized octabutoxy-naphthalocyanine following low-temperature centrifugal filtration. 10% (w/v) solutions of surfactants were used to dissolve the dye and then were subjected to 3 centrifugal filtration washes. Absorbance of the soluble retentate was measured at 860 nm.
Figure 17:
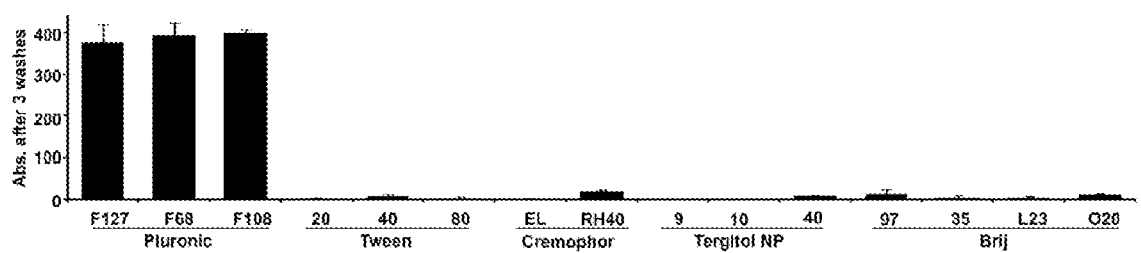
FIG. 17: Suitability of the Pluronic family of surfactants for low temperature (4 C) washing of the ONc hydrophobic dye resulting in surfactant-stripping to generate highly concentrated ONc ss-infroms.

First, we examined the retention of 10% (w/v) solutions of a few Pluronic surfactants as well as Cremophor EL and RH40 during centrifugal filtration at both 4° C. and 25° C. When in micelle form, the surfactant does not easily pass through the pores in the filtration membrane. As shown in FIG. 1, Pluronic F127 was retained at higher temperature but removed at low temperature (4 C) due to its temperature sensitive critical micelle concentration (CMC). However, F68 and F108, which both have a higher CMCs, could be removed using centrifugal filtration at both 25° C. and 4° C. The cremophors we examined could not be removed with centrifugal filtration. We next examined whether the surfactants could form frozen micelles with hydrophobic naphthalocyanines, which would be of larger size and therefore retained during the centrifugal filtration. The naphthalocyanine was added from a methylene chloride solution and was dropped into a stirring solution of surfactants. The organic solvent was allowed to evaporate and then the drugs were subjected to centrifugal filtration at 4° C. In conditions in which all the Pluronic is removed, a substantial amount of naphthalocyanine drug remained solubilized by frozen micelles. (FIG. 2). In another example, this washing procedure was repeated using an expanded set of surfactants at 10% w/w in water including Pluronic F127, Pluronic F108, Pluronic F68. Polysorbate 20, Polysorbate 40, Polysorbate 80. Cremophor EL, Cremophor RH40. Tergitol NP 9, Tergitol NP 10, Tergitol NP 40. Brij 97, Brij 35, Brij L23, Brij O20 and the 4° C. washing was repeated thrice. As shown in FIG. 17, only the Pluronics could generate a high absorbance in the washing process.

EXAMPLE 2

Figure 3:
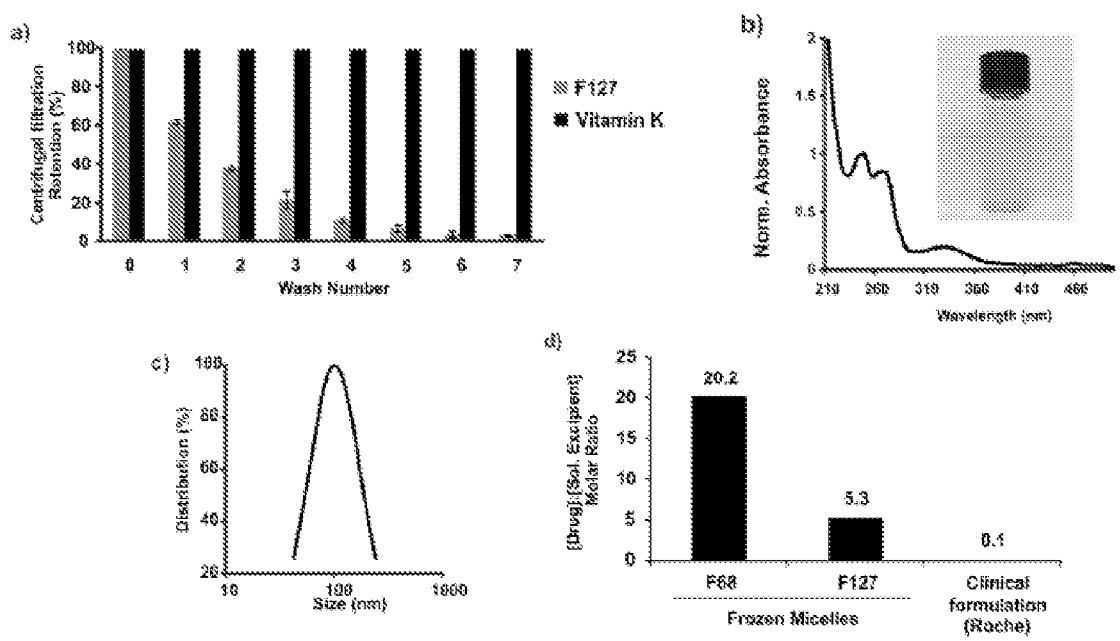
FIG. 3: Generation of Vitamin K ss-infroms. a) Vitamin K was dissolved in methylene chloride and added to a 10% (w/v) solution of F127. Following organic solvent evaporation, the solution was subjected to low-temperature centrifugal filtration washes and the amount of drug and Pluronic in the retentate was determined. b) Absorption spectrum of Vitamin K informs and photograph (inset). c) size distribution of Vitamin K informs. d) Comparison of molar ratios of purified Vitamin K informs formed with F68, F127 and also the mixed micelles clinical formulation on the market.

Vitamin K1 was assessed for suitability for forming induced frozen micelles. Vitamin K1 is a hydrophobic molecule involved in blood clotting that is sometimes given intravenously. As shown in FIG. 3a, following solubilization in Pluronic F127, vitamin K1 induced frozen micelles formed and centrifugal filtration could remove most the surfactant, leaving behind purified Vitamin K1 informs, which has a characteristic absorption spectrum (FIG. 3b). These ss-infroms had a size of 100 nm (FIG. 3c). Critically, were found to have a drug:surfactant as high as 20:1 when formed with F68, which is more than two orders of magnitude higher than the clinical formulation (FIG. 3d). Vitamin K1 was previously clinically formulated with Cremophor surfactant prior to being now exclusively available in a mixed micelle form that makes use of glycocholic acid surfactant. This additive may displace bilirubin and is not always advised for patients with advanced liver disease.

EXAMPLE 3

Figure 18:
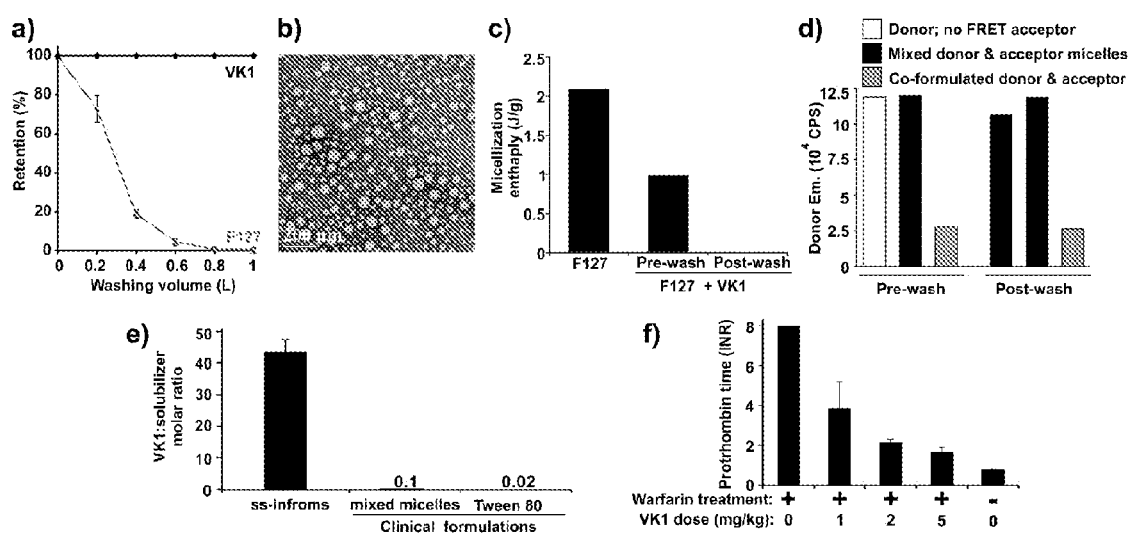
FIG. 18: a) During low temperature diafiltration, free F127 is stripped away whereas Vitamin K1 is fully retained. b) Transmission electron micrographs of Vitamin K1 ss-infroms. c) Differential scanning calorimetry measurement showing the surfactant stripping process removed all free F127 indicated by heat transferred during micellization. d) A Forster resonance energy transfer (FRET) assay, based on a small amount of hydrophobic fluorophores co-loaded with Vitamin K1 micelles, reveals that cargos are locked in kinetically frozen micelles without inter-micellar exchange pre- and post-surfactant stripping. e) Vitamin K1 ss-infroms exhibit a high drug-to-solubilizer molar ratio compared to clinical formulations. f) Vitamin K1 ss-infroms function effectively to combat the effects of orally administered warfarin in mice based on blood coagulation times.

In another example of Vitamin K1, a dialfiltration approach was used. 150 mg of Vitamin K1 was dissolved 1.5 mL methylene chloride (DCM) and added in 15 ml 10% (w/v) F127 and stirring until organic solvent evaporated. The solution was diluted by water to volume of 75 ml and subject to membrane filtration (Sartorius vivaflow, 1501008VS) at 4 C to remove unincorporated F127 and 5 fractions (200 ml each) of filtrate were collected. Retention of Vitamin K1 was quantified by absorbance measurement whereas F127 was quantified by the cobalt thiocyanate method. As shown in FIG. 18a, the Vitamin K1 was retained during the washing process, whereas the F127 was removed. As shown in FIG. 18b, this gave rise to nanoparticles less than 100 nm in size based on transmission electron micrographs. As shown in FIG. 42, the molar ratio of drug:F127 was 39.5:1; a typical concentrated solution could reach 150 mg/mL of Vitamin K1, the size was 74 nm and the polydispersity index was 0.25. When differential scanning calorimetry was used to probe the starting F127 solution, a micellization enthalpy of over 2 J/g was observed with the peak near 20 C (FIG. 18c). Following Vitamin K1 addition, the enthalpy peak became approximately 50% less, showing a large portion of the free F127 remained in solution. However, following the washing process, no detectable micellization enthalpy could be observed in the ss-infroms. As shown in FIG. 18d, Vitamin K1 infroms were doped with 1% 2, 9, 16, 23-tetra-tert-butyl-29H, 31H,phthalocyaine (BPc), a FRET donor for (Zinc, 2,22,20,20-tetra-tert-butyl-2,3-naphthalocyanine) ZnBPc. Donor DCM solution was made by dissolving 0.5 mg BPc, 49.5 mg Vitamin K1 in 500 μL methylene chloride. Acceptor methylene chloride solution was made by dissolving 5 mg ZnBNc and 45 mg Vitamin K1 in 500 μL methylene chloride. Pre mixed donor and acceptor methylene chloride solution was made by 0.5 mg BPc, 5 mg ZnBNc and 44.5 mg Vitamin K1 in 500 μL methylene chloride. The above three methylene chloride solution were added to 3 separate 5 ml 10% (w/v) F127 respectively, followed by stirring till the organic solvent evaporated. The post mixed donor and acceptor was made by combining donor solution and acceptor solution (1:1, v/v) after stirring. Then the fluorescence was measured on a fluorometer. When infroms were formed from the FRET donor and acceptor separately and then later combined, no appreciable energy transfer occurred, even following the washing process. When the FRET donor and acceptor were combined in organic solvent to make the infroms, a large amount of FRET was observed. These observations confirm the kinetically frozen nature of the ss-infroms. Using the diafiltration method, a high surfactant-to-drug molar ratio was observed for standard Vitamin K1 ss-infroms of over 40:1 based on NMR analysis, orders of magnitude greater than existing formulations (FIG. 18e). As shown in FIG. 18f, when administered intravenously to mice, Vitamin K1 ss-infroms could effectively counter the effects of warfarin administration. Six-week female ICR mice (Harlan) were feed with warfarin sodium solution for 24 hours prior to vitamin K1 informs intravenous injection. Mice (n=6) were injected intravenously with vitamin k ss-informs dose at 0, 1, 2.5 mg/kg. The remaining group used as control without feeding warfarin or any injections. 24 hours later, mouse blood was sampled and the INR values of the mice blood was determined by the Coagucheck XS system (Roche).

Figure 19:
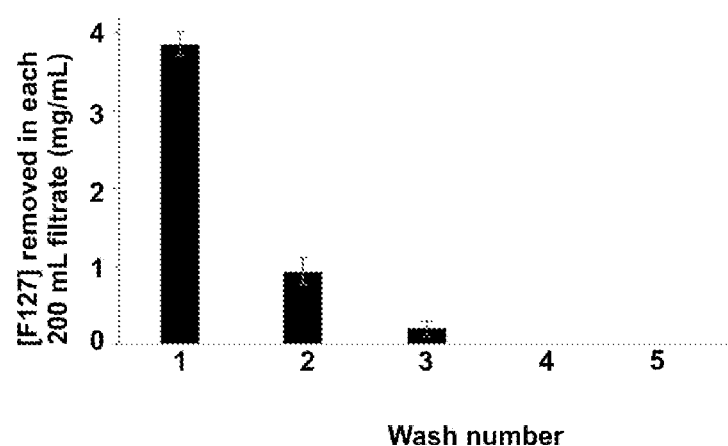
FIG. 19: During the Vitamin K1 washing process, all free F127 is removed from the retentate, based on the absence of any detectable surfactant coming out in the filtrate.

When the amount of unassociated and stripped F127 was measured in the washing filtrate for the Vitamin K1 infroms, after sufficient washing no further F127 could be detected (FIG. 19). This demonstrates that ss-infroms have been removed of unassociated Pluronic.

EXAMPLE 4

Figure 4:
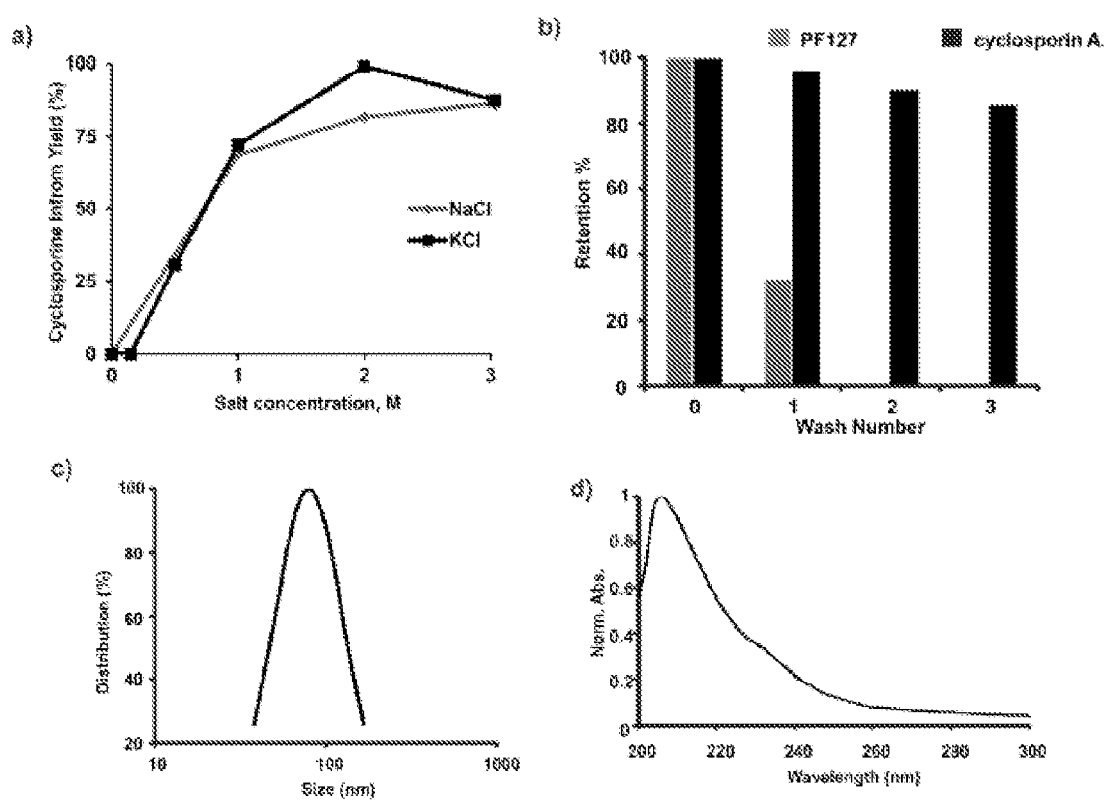
FIG. 4: Salt-assisted generation of Cyclosporine A ss-infroms. a) Cyclosporine A was dissolved in methylene chloride and added to a 10% (w/v) solutions of F127 containing the indicated amounts of salts. Following organic solvent evaporation, the solution was subjected to low-temperature centrifugal filtration washes and the amount of drug yield was determined. b) Retention of cyclosporine and Pluronic during wash steps (in 1 M NaCl). c) size distribution of cyclosporine informs. d) Absorption spectrum of cyclosporine informs.

Cyclosporine A was assessed for suitability for forming induced frozen micelles. Cyclosporine A is an immunosuppressive drug that is sometimes given intravenously, in Cremophor solution. Inform formation could be enhanced for cyclosporine by salt addition to the Pluronic solution (FIG. 4a). We hypothesize the reason is that the salt makes the solution more ionic and hydrophilic, resulting in more stable partitioning of the hydrophobic cargo into the frozen micelle core. The excess Pluronic could be washed away from the informs (FIG. 4b). The size was close to 100 nm and had the solution had a characteristic absorption peak (FIG. 4c,d).

EXAMPLE 5

Figure 20:
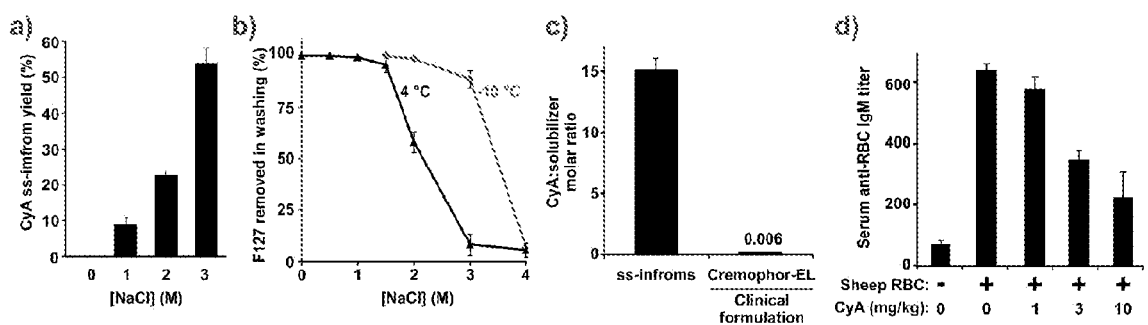
FIG. 20: a) Hypertonic saline enhances the yield of Cyclosporin a loaded micelles, b) F127 can be stripped effectively at lower temperatures, c) Surfactant stripped Cyclosporin a micelles exhibited a high molar ratio compared to clinical formulations, d) Cyclosporin a loaded surfactant stripped micelles effectively used as immunosuppressant.

In another example of Cyclosporine A, 10 mg Cyclosporine A was dissolved in 1 ml methylene chloride and added in 10 ml 10% (w/v) F127 solution with 0, 1, 2, 3 M NaCl. After stirring for 3 hours, the solution was subject to centrifugal filtration at 0° C. (for 0 M and 1 M) or −10° C. (for 2 M and 3 M) until ~200 µL of solution was retained or the volume of retentate keeps unchanged, corresponding salt solution was added back to concentrate and washing procedure was performed three times. The retentates were put through 0.45 µm filter and then High performance liquid chromatography (HPLC) was used to quantify the concentration of cyclosporine a. To quantify the Pluronic F127 removal percentage as a function of salt concentration at different temperatures, the filtrates were saved and Cobalt thiocyanate method was used. As shown in FIG. 42, the molar ratio of drug:F127 was 15:1; a typical concentrated solution could reach 7 mg/mL of Cyclosporine A, the size was 165 nm and the polydispersity index was 0.34. The effect of salt on the Cyclosporine A yield in ss-infroms was assessed as shown in FIG. 20a. Hypertonic saline enhanced the yield. FIG. 20b shows that free Pluronic can effectively be removed in hypertonic saline by low temperature washing (−10 C). As shown in FIG. 20c, the Cyclosporine A molar ratio in ss-infroms was orders of magnitude higher than existing clinical formulations. When ss-infroms of Cyclosporine A were administered to mice prior to injection with sheep red blood cells, it effectively inhibited the immune system response, as expected for an immunosuppressive drug (FIG. 20d).

EXAMPLE 6

Figure 5:
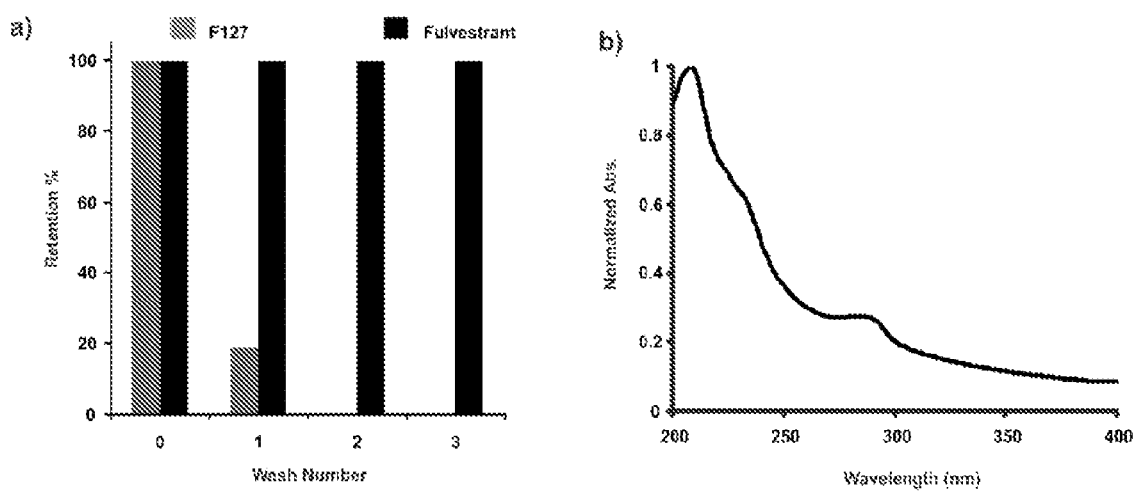
FIG. 5: Generation of fulvestrant ss-infroms. a) Fulvestrant was dissolved in methylene chloride and added to a 10% (w/v) solutions of F127. Following organic solvent evaporation, the solution was subjected to low-temperature centrifugal filtration washes and the amount of drug and Pluronic at each washing step was determined. b) Absorption spectrum of fulvestrant informs.

Numerous other ss-infroms of hydrophobic drugs were generated by dissolving 100 mg drug in 1 ml methylene chloride (DCM) and adding this to a 10 mL 10% (w/v) F127 solution (with or without NaCl) and stirred until organic solvent evaporated. Removal of unincorporated F127 then involved either: 1) The centrifugal filtration F127 stripping method: solutions was subjected to centrifugal filtrations (fisher #UCF9-100-24) at low temperature (0° C., 4° C. or −10° C.), until ~200 µL of the solution was retained (or the volume of retentate was unchanged). Water (or NaCl solution) was added back to the concentrate and the washing procedure was repeated three times. 2) Diafiltration filtration method: For large scale (>15 ml) or high salt (>2 or 3 M) solution, removal process was conducted by membrane filtration (Sartorius vivaflow, 1501008VS) assembled with peristalsis pump (Masterflex L/S) and tubing (masterflex 6434-16 at low temperature (−7° C. for 2 M, −12° C. for 3 M, and −16° C. for 4 M). To reach lower temperature and maximize F127 removal percentage, membranes modules, tubing, and solution to be washed were immersed in mixture of ethylene glycol and ethanol (vol/vol=9:1), and dry ice was used as cooling agent. Fulvestrant was assessed for suitability for forming induced frozen micelles. Fulvestrant is an injectable hormonal chemotherapeutic drug. As shown in FIG. 5a, fulvestrant micelles formed following addition to Pluronic and then the excess Pluronic could be washed away while the fulvestrant was retained in fulvestrant informs. The solution had a characteristic absorption spectra (FIG. 5b).

EXAMPLE 7

Figure 6:
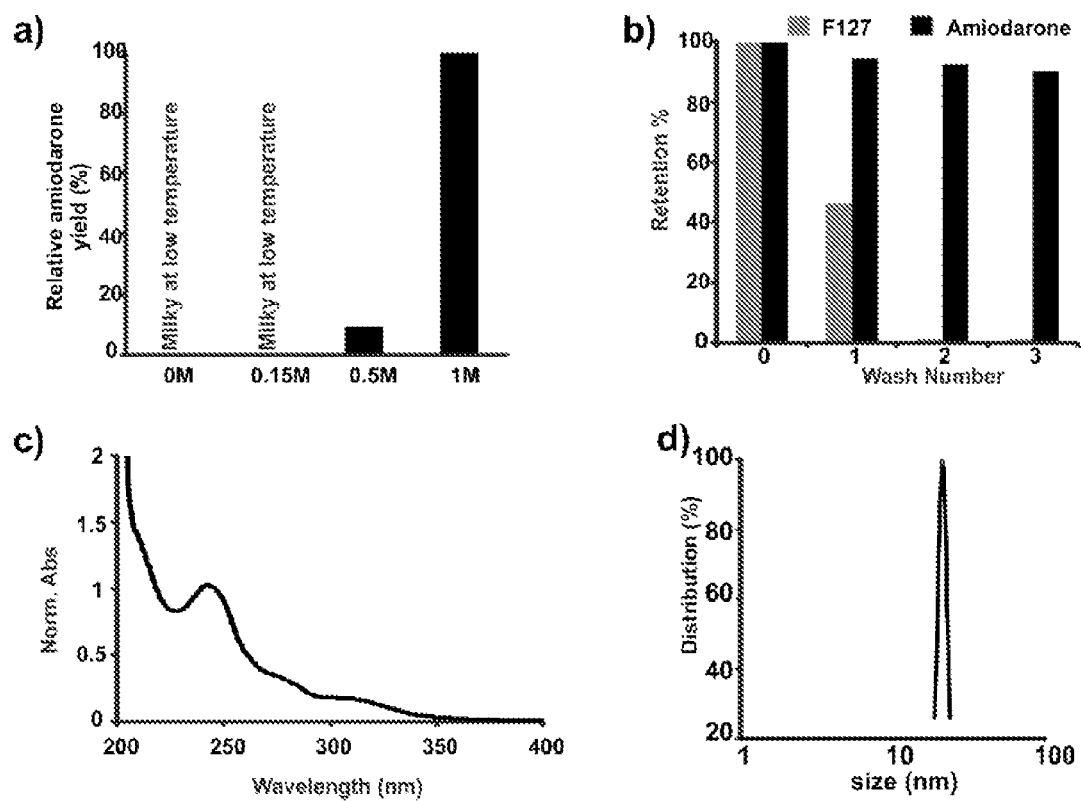
FIG. 6: Generation of amiodarone ss-infroms. a) Amiodarone was dissolved in methylene chloride and added to a 10% (w/v) solutions of F127 containing the indicated amounts of NaCl. Following organic solvent evaporation, the solution was subjected to low-temperature centrifugal filtration washes and the amount of drug yield was determined. b) Retention of amiodarone and Pluronic during wash steps (in 1 M NaCl). c) Absorption spectrum of amiodarone informs. b) Size distribution of amiodaron informs.

Amiodarone was assessed for suitability for forming induced frozen micelles. Amiodarone is an injectable cardiac drug. As shown in FIG. 6a, sodium chloride greatly enhanced amiodarone inform formation. Excess Pluronic could be washed away, whereas the Amiodarone was retained (FIG. 6b). The informs had a characteristic absorption spectra and narrow size distribution close to 30 nm (FIG. 6 c&d).

EXAMPLE 8

Figure 7:
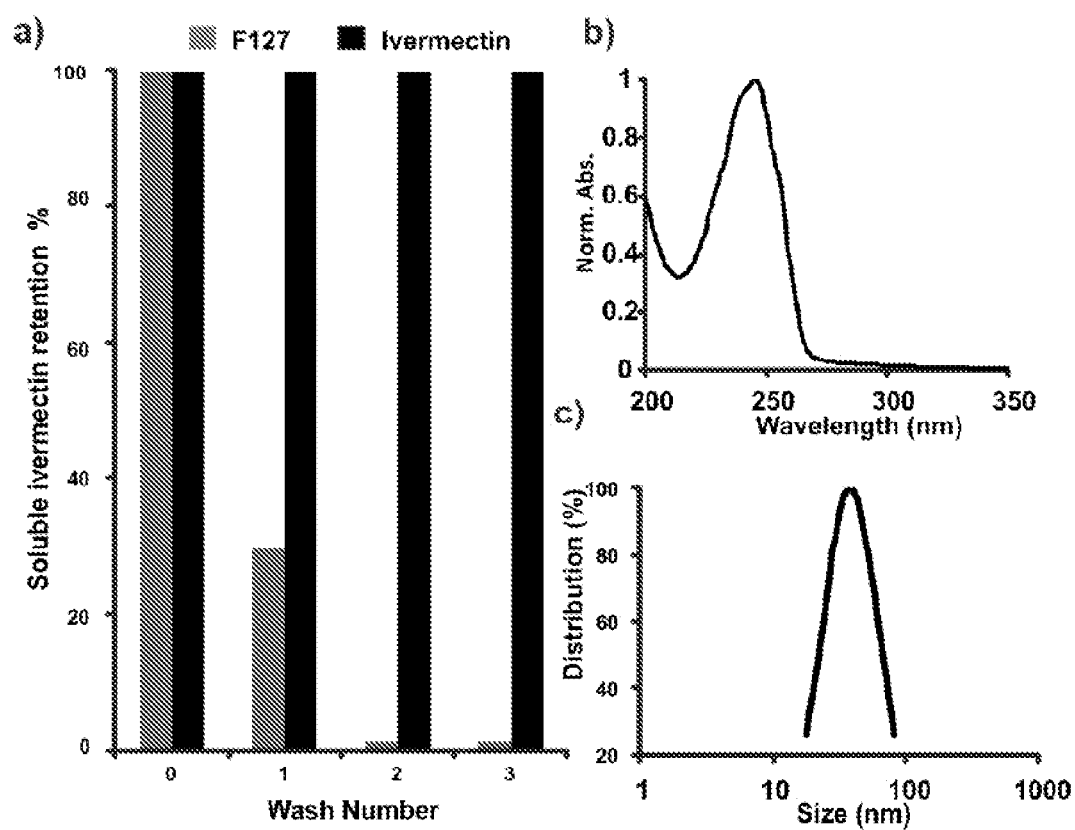
FIG. 7: Generation of ivermectin ss-infroms. a) Ivermectin was dissolved in methylene chloride and added to a 10% (w/v) solution. Following organic solvent evaporation, the solution was subjected to low-temperature centrifugal filtration washes and the amount of drug yield was determined. b) Absorption spectrum of ivermectin informs. b) Size distribution of ivermectin informs.

Ivermectin was assessed for suitability for forming induced frozen micelles. Ivermectin is an antiparasitic drug that has a main application of the injectable form in treating livestock but has been used in humans as well. As shown in FIG. 7a, ivermectin informs could be formed, which allowed the excess Pluronic to be washed away whereas the ivermectin was retained. Ivermectin informs had a characteristic absorption peak at 240 nm and a size close to 40 nm (FIG. 7 b,c). 100 mg Ivermectin was dissolved in 1 ml methylene chloride and added to 10 ml 10% (w/v), followed by stirring until organic solvent evaporated. To remove unincorporated F127, solutions was subjected to centrifugal filtrations (fisher #UCF9-100-24) at 0° C. until ~200 µL of the solution was retained. Water was added back to the concentrate and the washing procedure was repeated three times. As shown in FIG. 42, the molar ratio of drug:F127 was 45:1; a typical concentrated solution could reach 79 mg/mL of Ivermectin, the size was 39 nm and the polydispersity index was 0.03.

EXAMPLE 9

Figure 8:
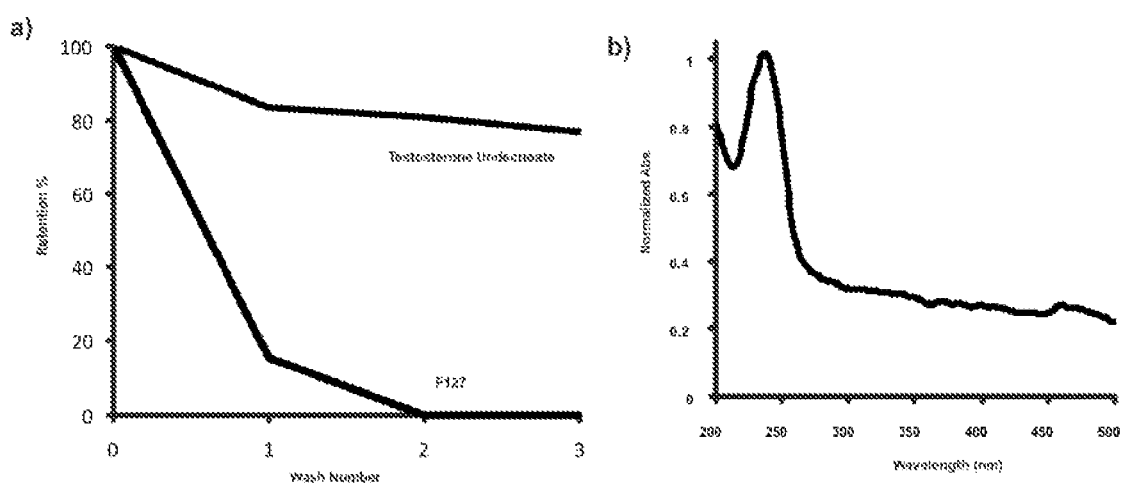
FIG. 8: Generation of testosterone undecanoate ss-infroms. a) Testosterone undecanoate was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of testosterone undecanoate ss-infroms
Figure 21:
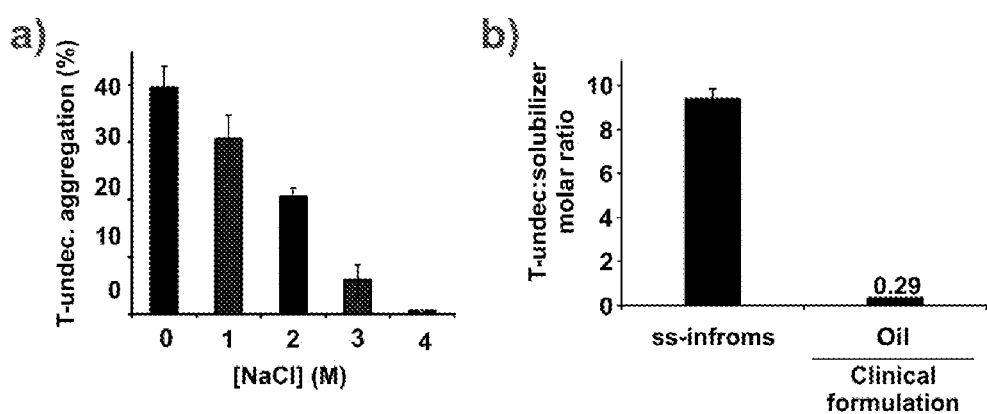
FIG. 21: a) Hypertonic saline improves yield of testosterone undecanoate loaded micelles by salt, b) Testosterone undecanoate ss-infroms exhibited higher molar ratio compared to clinical formulations.

Testosterone undecanoate was assessed for suitability for forming induced frozen micelles. Testosterone undecanoate is an esterified version of testosterone, which is the major androgen and has been used for hormone replacement and explored for male contraception. It is usually administered as an intramuscular injection in vegetable oil. As shown in FIG. 8a, testosterone undecanoate informs could be formed, which allowed the excess Pluronic to be washed away whereas the testosterone undecanote was retained. Testosterone undecanoate informs had a characteristic absorption peak at 235 nm (FIG. 8b). Testosterone undecanoate informs had a drug:pluronic ratio of 40:1. In another example, testosterone undecanoate was stirred at the small scale and 10 mg drug was dissolved in 100 µL DCM and added in 1 ml 10% (w/v) F127 aqueous solution with 0, 1, 2, 3, 4 M NaCl, followed by stirring for 3 h till DCM evaporate completely. Then the solution was subject to spinning at 5,000×g for 10 minutes. The supernatant was discarded and the pellect was dissolved in 1 ml ethanol, and absorbance at 240 nm (for testosterone undecanoate) and 230 nm (for cabazitaxel) was measured to quantify the unincorporated drugs. 100 mg Teststorone Undecanoate was dissolved in 1 ml methylene chloride (DCM) and added to 10 ml 10% 10% (w/v) F127 with 4 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −16° C. and 4 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. As shown in FIG. 42, the molar ratio of drug:F127 was 9:1; a typical concentrated solution could reach 16 mg/mL of testosterone undecanoate, the size was 112 nm and the polydispersity index was 0.19. As shown in FIG. 21a hypertonic saline to 4 M could greatly prevent aggregation of testosterone undecanoate. Compared to existing formulation which are dissolved in oil, ss-infroms had a much higher drug-to-solubilizer molar ratio (FIG. 21b).

EXAMPLE 10

Figure 9:
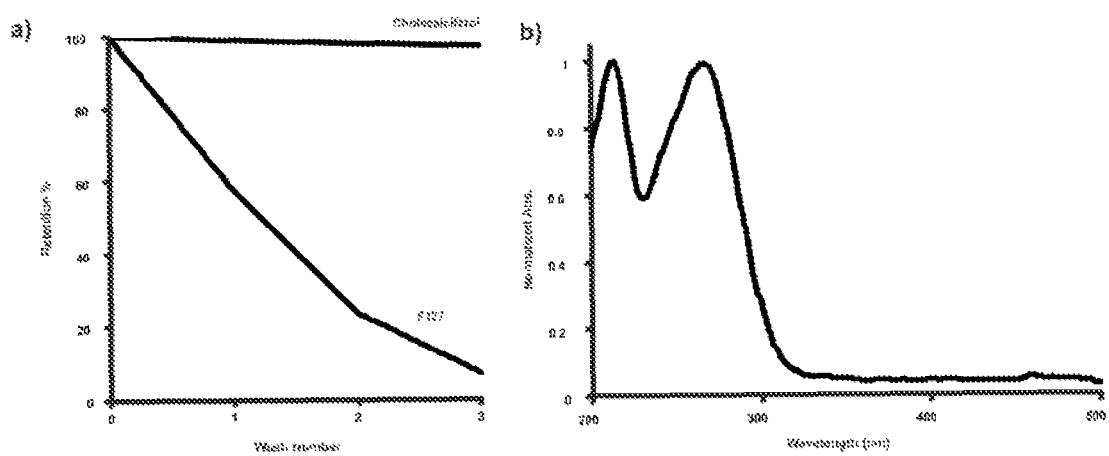
FIG. 9: Generation of cholecalciferol ss-infroms. a) Cholecalciferol was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of cholecalciferol ss-infroms

Cholecalciferol was assessed for suitability for forming induced frozen micelles. Cholecalciferol is a form of vitamin D. As shown in FIG. 9a, cholecalciferol informs could be formed, which allowed the excess Pluronic to be washed away whereas the cholecalciferol was retained. Cholecalciferol informs had a characteristic absorption peak at 270 nm (FIG. 9b). 100 mg Cholecalciferol was dissolved in 1 ml methylene chloride (DCM) and added to 10 ml 10% 10% (w/v) F127 with 2 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −7° C. and 2 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. Using hypertonic saline for formation and washing, as shown in FIG. 42, the molar ratio of drug:F127 was 9:1; a typical concentrated solution could reach 75 mg/mL of Cholecalciferol, the size was 44 nm and the polydispersity index was 0.16.

EXAMPLE 11

Figure 10:
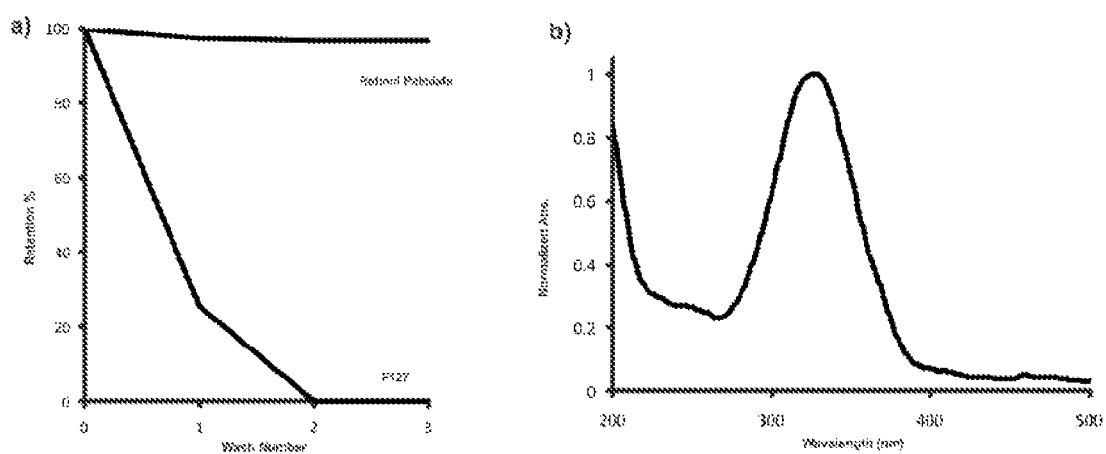
FIG. 10: Generation of retinol palmitate ss-infroms. a) Retinol palmitate was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of retinol palmitate informs. 100 mg retinal palmitate was dissolved in 1 ml methylene chloride (DCM) and added to 10 ml 10% (w/v) F127 with 2 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −7° C. and 2 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent.

Retinol palmitate was assessed for suitability for forming induced frozen micelles. Retinol palmitate is an esterified vitamin A precursor. As shown in FIG. 10a, retinol palmitate informs could be formed, which allowed the excess Pluronic to be washed away whereas the retinol palmitate was retained. Retinol palmitate informs had a characteristic absorption peak at 320 nm (FIG. 10b). 100 mg retinal palmitate was dissolved in 1 ml methylene chloride (DCM) and added to 10 ml 10% (w/v) F127 with 2 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −7° C. and 2 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. Using hypertonic saline for formation and washing, as shown in FIG. 42, the molar ratio of drug:F127 was 54:1; a typical concentrated solution could reach 38 mg/mL of Retinol palmitate, the size was 114 nm and the polydispersity index was 0.1625

EXAMPLE 12

Figure 11:
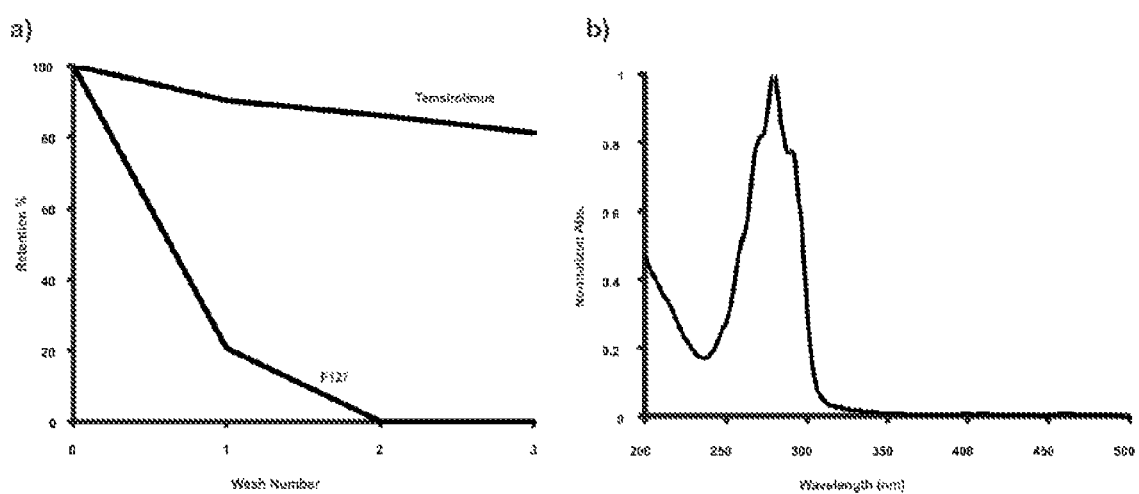
FIG. 11: Generation of temsirolimus ss-infroms. a) Temsirolimus was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of temsirolimus informs

Temsirolimus was assessed for suitability for forming induced frozen micelles. Temsirolimus is an immunosuppressive drug that is given intravenously in some circumstances. As shown in FIG. 11a, temsirolimus informs could be formed, which allowed the excess Pluronic to be washed away whereas the temsirolimus was retained. Temsirolimus informs had a characteristic absorption peak at 275 nm (FIG. 112b).

EXAMPLE 13

Figure 12:
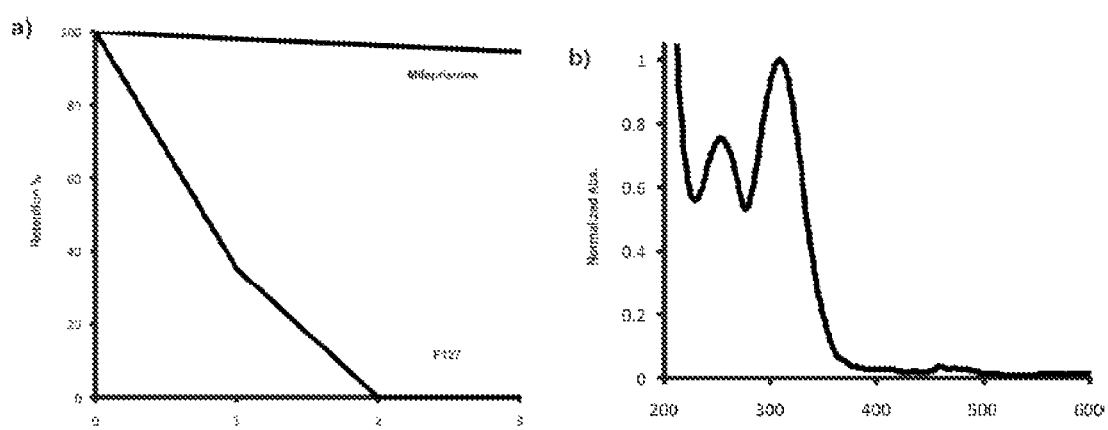
FIG. 12: Generation of mifopristone ss-infroms. a) Testosterone undecanoate was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of testosterone undecanoate ss-informs

Mifopristone was assessed for suitability for forming induced frozen micelles. Mifopristone is a steroid compound that is commonly used as a abortifacient. It is not often given by injection. As shown in FIG. 12a, mifopristone informs could be formed, which allowed the excess Pluronic to be fully washed away whereas the mifepristone was retained. Mifopristone informs had a characteristic absorption peak at 310 nm (FIG. 12b).

EXAMPLE 14

Figure 13:
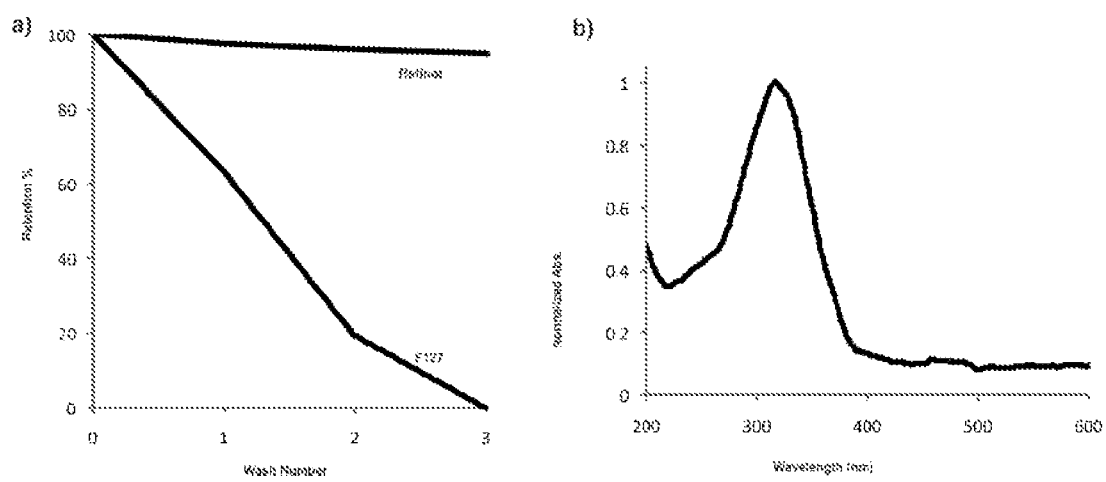
FIG. 13: Generation of retinol ss-infroms. a) Retinol was dissolved in methylene chloride and added to a 10% (w/v)

Retinol was assessed for suitability for forming induced frozen micelles. Retinol is a form of Vitamin A. As shown in FIG. 13a, retinol informs could be formed, which allowed the excess Pluronic to be fully washed away whereas the retinol was retained. Retinol informs had a characteristic absorption peak near 300 nm (FIG. 13b).

EXAMPLE 15

Figure 14:
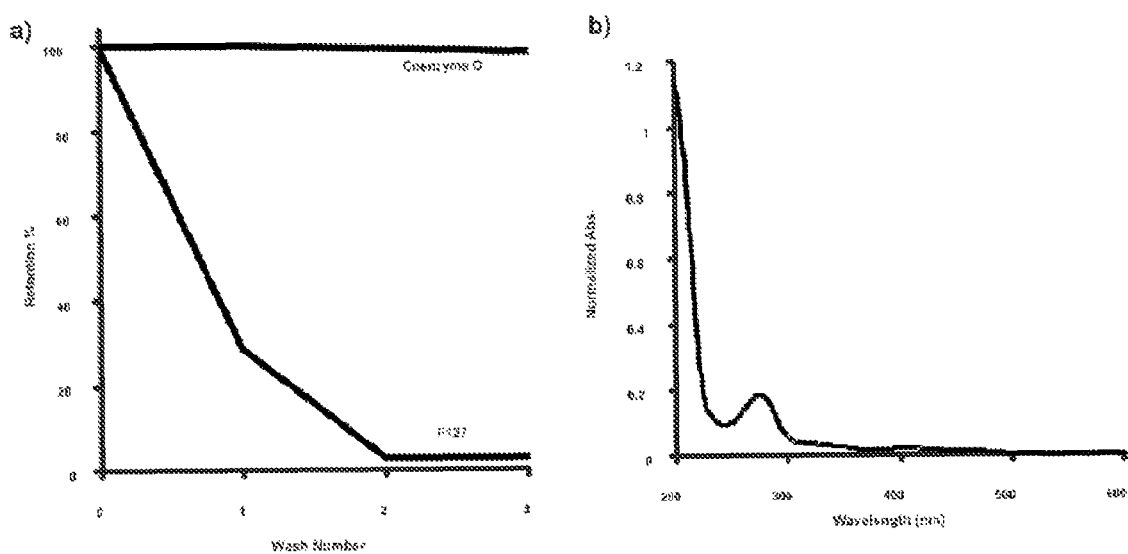
FIG. 14: Generation of coenzyme Q10 ss-infroms. a) Coenzyme Q10 was dissolved in methylene chloride and added to a 10% (w/v) solution of F127. Following organic solvent evaporation, the solution was subjected to low-temperature centrifugal filtration washes and the amount of drug and F127 in the retentate was determined. b) Absorption spectrum of Coenzyme Q10 ss-infroms

Coenzyme Q10 was next assessed for suitability for forming induced frozen micelles. Coenzyme Q10 is an essential vitamin. As shown in FIG. 14a, coenzyme Q10 informs could be formed, which allowed the excess Pluronic to be fully washed away whereas the Coenzyme Q 10 was retained. Coenzyme Q informs had a characteristic absorption peak near 290 nm (FIG. 14b). 100 mg coenzyme Q10 was dissolved in 1 ml methylene chloride (DCM) and added to 10 ml 10% 10% (w/v) F127 with 4 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −16° C. and 4 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. As shown in FIG. 42, the molar ratio of drug:F127 was 30:1; a typical concentrated solution could reach 42 mg/mL of Coenzyme Q, the size was 115 nm and the polydispersity index was 0.28.

EXAMPLE 16

Figure 15:
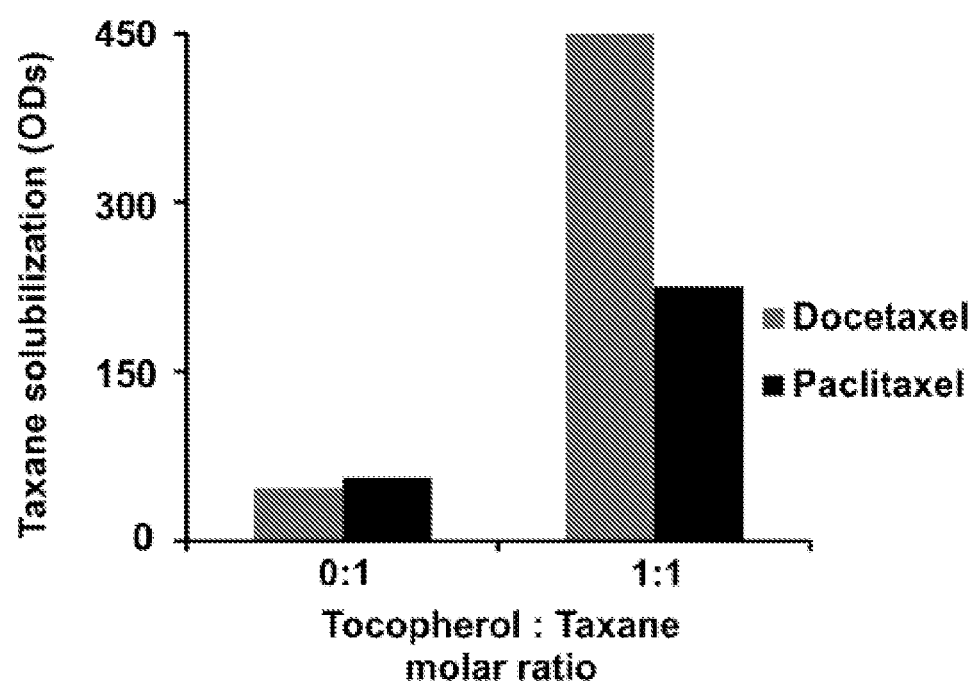
FIG. 15: Enhancement of taxane inform formation with Vitamin E co-loading. Docetaxel or paclitaxel were dissolved in methylene chloride along with the indicated amount of Vitamin E (alpha tocopherol) and added to a 10% (w/v) solution of F127. Following organic solvent evaporation, the solution was subjected to centrifugation to determine the absorbance of solubilized taxane.
Figure 16:
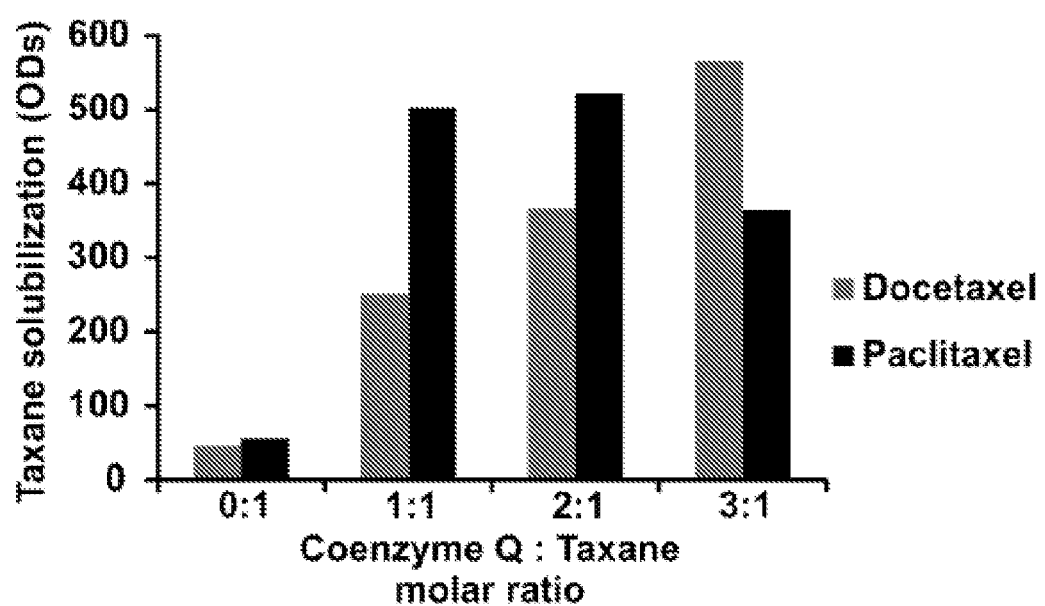
FIG. 16: Enhancement of taxane inform formation with Coenzyme Q co-loading. Docetaxel or paclitaxel were dissolved in methylene chloride along with the indicated amount of Conenzyme Q10 and added to a 10% (w/v) solution of F127. Following organic solvent evaporation, the solution was subjected to centrifugation to determine the absorbance of solubilized taxane

Next, we examined taxane inform formulations. Taxanes are commonly-used chemotherapeutics that act on microtubules in cancer cells. Docetaxel and paclitaxel are the two most common taxanes. Even in 3 M NaCl, inform formation was ineffective (FIG. 15). However the addition of vitamin E, at an equimolar ratio, both docetaxel and paclitaxel inform formation was drastically enhanced. Likewise, addition of coenzyme Q had the same effect of dramatically increasing the efficacy of inform formation of docetaxel and paclitaxel (FIG. 16). The effects of hypertonic saline on improving the solubility of cabazitaxel (CTX) formed into F127 ss-infroms is shown in Fig NEW6a and using 3 or 4 M NaCl substantially prevents aggregation.

EXAMPLE 17

Figure 22:
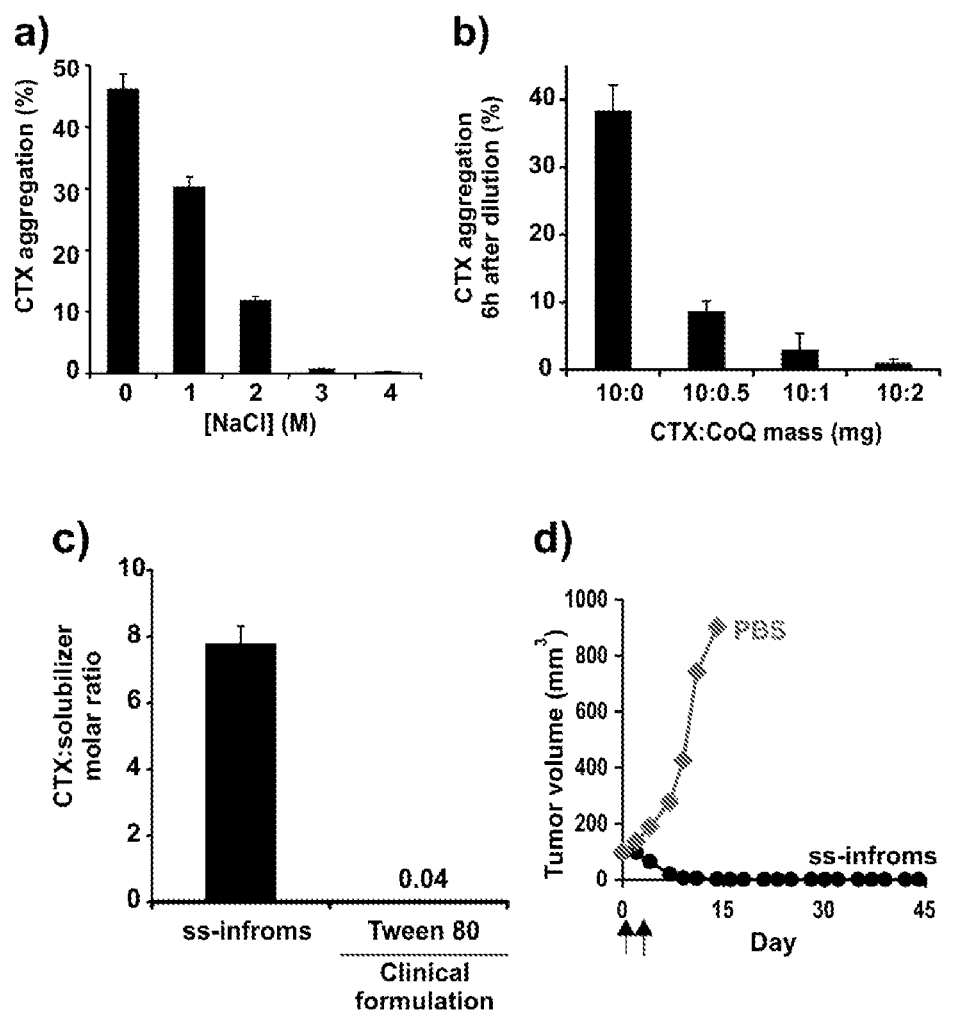

In another example, 10 mg cabazitaxel (CTX) with different mass ratio of coenzyme Q10 (CTX: CoQ=10:0; 10:0.5; 10:1; 10:2) were dissolved in 100 µL DCM and added to 1 ml 10% (w/v) F127 aqueous solution with 3.5 M NaCl followed by stirring for 5 hours (till the solvent evaporated and solutions got clear). Hypertonic saline was found to prevent aggregation during micelle formation (FIG. 22*a*). Afterwards, the solutions was diluted 1 in 15 in water, sitting at room temperature. At different time points (1 h, 2 h, 3 h, 4 h, 5 h, 6 h), solutions were subjected to spinning at 5,000×g for 5 minutes; data in FIG. 22*b*) were gathered at 6 h. The clear and yellow supernatant was discarded and 1 ml water was added back to rinse white pellet and the spin process was repeated. After discarding the supernatant, the CTX pellet was dissolved in 1 ml ethanol and absorbance was measured to quantify the amount of drug. These results are shown in FIG. 22*b*, and adding a mass ratio of 10:1 or 10:2 CTX:CoQ prevents aggregation following dilution into water. As shown in FIG. 22*c*, the CTX ss-infroms have a much higher drug to solubilizer molar ratio relative to the current clinical formulation. As shown in FIG. 42, the molar ratio of drug:F127 was nearly 8:1; a typical concentrated solution could reach 41 mg/mL of CTX, the size was 62 nm and the polydispersity index was 0.1. As shown in FIG. 22*d*, ss-infroms, when administered intravenously at a 30 mg/kg cabazitaxel dose to athymic nude mice bearing subcutaneous Mia PACA-2 tumors of 4-5 mm in diameter at day 0 and day 4, could eradicate tumors.

EXAMPLE 18

100 mg a-Tocopherol was dissolved in 1 ml methylene chloride (DCM) and added to 10 ml 10% 10% (w/v) F127 with 2 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −7° C. and 2 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. As shown in FIG. 42, the molar ratio of drug:F127 was 21:1; a typical concentrated solution could reach 58 mg/mL of a-Tocopherol, the size was 86 nm and the polydispersity index was 0.26.

EXAMPLE 19

100 mg Ergocalciferol was dissolved in 1 ml methylene chloride (DCM) and added to 10 ml 10% 10% (w/v) F127 with 2 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −7° C. and 2 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. As shown in FIG. 42, the molar ratio of drug:F127 was 9:1; a typical concentrated solution could reach 64 mg/mL of Ergocalciferol, the size was 112 nm and the polydispersity index was 0.31.

EXAMPLE 20

100 mg squalene was dissolved in 1 ml methylene chloride (DCM) and added to 10 ml 10% 10% (w/v) F127 with 3 M NaCl and stirring until organic solvent evaporated. Removal F127 of unincorporated process was conducted by membrane filtration (Sartorius vivaflow, 1501008VS) assembled with peristalsis pump (Masterflex L/S) and tubing (masterflex 6434-16). Removal process was performed at −12° C. and 3 M NaCl solution was used to dia-filtration solution. To maximize F127 removal percentage, membranes modules, tubing, and solution to be washed were immersed in mixture of ethylene glycol and ethanol (v/v=9:1), and dry ice was used as cooling agent. As shown in FIG. 42, the molar ratio of drug:F127 was 43:1; a typical concentrated solution could reach 80 mg/mL of squalene, the size was 81 nm and the polydispersity index was 0.28.

EXAMPLE 21

2 mg 2,9,16,23-Tetra-tert-butyl-29H,31H-phthalocyanine was dissolved in 1 ml methylene chloride and added to 10 ml 10% (w/v), followed by stirring until organic solvent evaporated. To remove unincorporated F127, solutions was subjected to centrifugal filtrations (fisher #UCF9-100-24) at 4° C. until ~200 µL of the solution was retained. Water was added back to the concentrate and the washing procedure was repeated three times. As shown in FIG. 42, the molar ratio of drug:F127 was 5:1; a typical concentrated solution could reach 19 mg/mL, the size was 18 nm and the polydispersity index was 0.15.

EXAMPLE 22

2 mg Zinc 2,11,20,29-tetra-tert-butyl-2,3-naphthalocyanine was dissolved in 1 ml methylene chloride and added to 10 ml 10% (w/v), followed by stirring until organic solvent evaporated. To remove unincorporated F127, solutions was subjected to centrifugal filtrations (fisher #UCF9-100-24) at 4° C. until ~200 µL of the solution was retained. Water was added back to the concentrate and the washing procedure was repeated three times. As shown in FIG. 42, the molar ratio of drug:F127 was 4:1; a typical concentrated solution could reach 30 mg/mL, the size was 20 nm and the polydispersity index was 0.16.

EXAMPLE 23

2 mg 5,9,14,18,23,27,32,36-octabutoxy-2,3-naphthalocyanine was dissolved in 1 ml methylene chloride and added to 10 ml 10% (w/v), followed by stirring until organic solvent evaporated. To remove unincorporated F127, solutions was subjected to centrifugal filtrations (fisher #UCF9-100-24) at 4° C. until ~200 µL of the solution was retained. As shown in FIG. 42, the molar ratio of drug:F127 was 3:1; a typical concentrated solution could reach 13 mg/mL, the size was 20 nm and the polydispersity index was 0.16.

EXAMPLE 24

This example, containing a methods and results section, describes the preparation of nanonaps and the use of the nanonaps for GI imaging. Materials were obtained from Sigma unless otherwise indicated.

Methods

Solubilization and retention of dyes with varying hydrophobicity: Log P values were evaluated using the ALOG PS 2.1 program hosted at vcclab.org. 2 mg of methylene blue, quinaldine red, rhodamine 6G, IR780, 2,11,20,29-Tetra-tert-butyl-2,3-naphthalocyanine (BNc), Zinc-2,11,20,29-Tetra-tert-butyl-2,3-naphthalocyanine (ZnBNc), 5,9,14,18,23,27,32,36-Octabutoxy-2,3-naphthalocyanine (ONc), Nickel-5,9,14,18,23,27,32,36-Octabutoxy-2,3-naphthalocyanine (NiONc), Vanadyl 2,11,20,29-tetra-tert-butyl-2,3-naphthalocyanine (VBNc), 2,9,16,23-Tetra-tert-butyl-29H,31H-phthalocyanine (BPc), Vanadyl 3,10,17,24-tetra-tert-butyl-1,8,15,22-tetrakis(dimethylamino)-29H,31H-phthalocyanine (VBPc) were dissolved in 1 mL dichloromethane or methanol for MB then added dropwise to a 10% w/v solution of Pluronic F127 (Sigma #P2443). The solution was stirred in a fume hood at room temperature (or 80° C. for MB) for 4 hours to evaporate the organic solvent. After centrifugation at 4000×g for 5 minutes to remove any large aggregates, 100 µL of supernatant was diluted in 3 mL of 20 mM sodium cholate solution. After recording the absorbance, the solution was placed in dialysis tubing (Fisher, #21-152-16; nominal molecular weight cut-off of 12,000-14,000 Daltons) and dialyzed against 500 mL of 20 mM sodium cholate buffer at room temperature. The buffer was changed after 4 hours. After 24 hours, the absorbance of the solution in dialysis tubing was measured again to determine dye retention percentage.

The micelles were prepared as follows. Briefly, 2 mg Nc or Pc dye was dissolved in 1 mL dichloromethane was added dropwise to an aqueous solution of 10 mL F127 (10%, w/v). Dichloromethane was chosen since the dyes were all found to be soluble (>10 mg/mL), whereas methanol solubility was less than 0.1 mg/mL. The suspension was stirred in a fume hood at room temperature for 4 hours to evaporate the dichloromethane. After centrifugation at 4000×g for 5 minutes to remove aggregates, the supernatant was used for CMC switching purification. To remove unincorporated F127, the supernatant was cooled on ice then centrifuged in an Amicon Ultra-15 centrifugal filtration device with a 100,000 MWCO (Fisher #UFC9-100-24) at 4° C. until 200 µL of solution was retained in the filtration device. The filtrate was stored for determination of F127 and dye concentration. Water was added back to the filtration device and the washing procedure was repeated at least three times.

Figure 30:
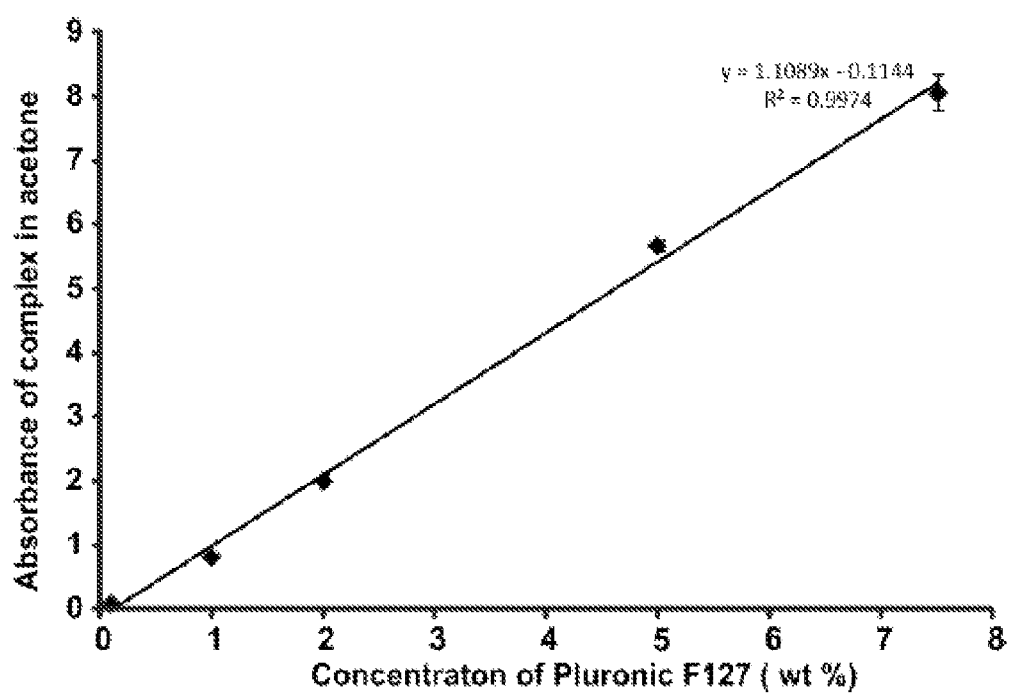
FIG. 30: Calibration curve used to determine free F127 concentration during centrifugal washing. Pluronic F127 and cobalt thiocyanate formed a dark blue complex (absorbance at 623 nm). The presented data accounts for dilution factors. Mean+/−std. dev. for n=3.

To quantify incorporated F127, the collected filtrates were collected and F127 concentration was determined by a previously reported colorimetric assay method with minor modifications. In brief, a cobalt thiocyanate reagent was prepared first by dissolving 0.3 g cobalt nitrate hexahydrate and 1.2 g ammonium thiocyanate in 3 mL water. Then 100 µL cobalt thiocyanate solution, 40 µL F127 solution in the concentration range of 0-7.5 wt % (more concentrated F127 solutions were diluted to fit the range), 200 µL ethyl acetate and 80 µL ethanol were combined. The mixture was vortexed gently and centrifuged at 14000×g for 1 min. The blue supernatant was removed and the blue pellet was washed using ethyl ether several (~5) times until the supernatant became colourless. The pellet was then dissolved in 1 mL acetone to measure the absorbance at 623 nm (FIG. 30 shows the standard curve of the cobalt thiocyanate-F127 complex and the concentration of F127). The F127 retention percentage after each wash was calculated by weighing the mass and determination of the mass percentage by the colorimetric assay. The concentrations of dyes were by determined by measuring absorbance.

For reconstitution studies, nanonaps were prepared by the same procedure using 2 mg ONc dye. DMPC liposome were made by dissolving 2 mg of ONc and 19.9 mg of DMPC (corresponding to 95 molar % DMPC) in a small volume of chloroform. After evaporation of the solvent by nitrogen purging, the film was put under vacuum for 1 hour and then rehydrated with 1.5 mL distilled water and sonicated for 30 min. ONc nanonaps and liposomes were then freeze dried overnight (Labconco Freezone). The powder was then resuspended in a minimal volume of water (50 µL) and the absorbance was recorded. The samples were briefly centrifuged to remove large insoluble aggregates that interfered with absorption baseline.

Characterization of Nanonap Physical and Optical Properties: Size and zeta potential measurement were carried out using dynamic light scattering with a Nano ZS90 Zetasizer (Malvern Instruments). Transmission electron microscopy was performed using a JEM-2010 electron microscope to determine the morphology of an aqueous dispersion of nanonaps negatively stained with 1% uranyl acetate. Absorbance was measured by with a Lambda 35 UV/VIS spectrophotometer (Perkin Elmer) at room temperature using cuvettes with 1 cm path lengths, except for the high-concentrated spectral shifting analysis which used 10 µm path-length cuvettes.

X-ray diffraction powder pattern was carried with freeze dried samples on a Rigaku Ultima IV with operating conditions of 40 KV, 44 mA, and 1.76 kW. The source of the diffractometer used was a Cu K'α radiation at a 1.54 Å wavelength with a monochromator filter and analysed in a θ/2θ mode at room temperature. The 2θ scan data were collected at a 0.030 interval and the scan speed was 0.5 deg/minute. The technique used for measuring intensities was the focusing beam method.

Scattering and fluorescence properties were assessed using a fluorometer (Photon Technology International). To examine the scattering properties of nanonaps (ZnBNc nanonaps with peak absorption at 707 nm) and gold nanorods with 700 nm peak absorption (NanoPartz # A12-10-700) were used and extinction was normalized to 0.05 at 700 nm in water. Resonance scattering was recorded on a fluorometer with slit widths of 2 nm with simultaneous excitation and emission scanning between 600 and 800 nm. Buffer scattering background blanks were recorded and subtracted from the nanoparticle measurements. Normalized fluorescence measurements were made by measuring the emission spectra with 300 nm excitation of absorbance-matched dilute ZnBNc either in nanonap form or directly dissolved in dichloromethane with 4 nm excitation and emission slit widths.

To determine optical parameters, concentrated nanonaps with known absorbance were lyophilized. The mass of nanonap powder was determined and then a portion of the powder was dissolved in dichloromethane to the determine concentration and mass of dye. The mass of F127 was then determined based on the difference in total lyophilized mass. To calculate nanoparticle optical properties, the density of the dyes was assumed to be 1 g/cm$^3$, since the hydrophobic dyes can be floated/suspended in water and the density of F127 was taken as 1.05 g/cm$^3$. The diameter of nanonaps, which are uniformly spherical were measured using dynamic light scattering and were found to be 17 nm, 20 nm, 26 nm, and 20 nm for BPc, ZnBNc, BNc and ONc respectively. The nanonap volume was assumed to exclude water from its interior. Based on the average density and volume of nanonaps, a per particle mass and subsequent number of dyes per particle could be estimated.

To assess the stability of nanonaps in simulated gastric fluid (SGF) and simulated intestine fluid (SIF), nanonaps were dialyzed against 200 mL SGF (Ricca, #7108-32) with added pepsin and pancreatin-containing SIF (Ricca #7109-32). Concentrated nanonaps were diluted with SGF and SIF so that the absorbance was close to 1, then dialyzed at 37° C.

Nanonap clearance study: Animal experiments were performed in accordance with the University at Buffalo Institutional Animal Care and Use Committee. 6-8 weeks female BALB/c mice (Harlan labs) were starved overnight with free access to water. Food was introduced after gavage. After gavage of 100 ODs ONc nanonaps (3.42 mg) or methylene blue, the mice were transferred to metabolic cages and feces and urine were collected separately. Feces and urine were collected at 0, 2, 4, 8, and 24 hours, weighed and kept at 4° C. prior to analysis. For determination of recovery percentages, the absorbance of urine and serum samples was measured directly. Tissues or feces (~50 mg) were dissolved in 2 mL chloroform (methanol for the recovery of methylene blue), and subjected to disruption using a Tissue Tearor homogenizer (Model 985-370) for 30 seconds or until the dyes were dissolved completely. The solutions were centrifuged at 3000×g for 3 minutes to remove debris and the absorbance of the chloroform containing dyes was measured to determine the recovery. To calibrate the absorbance difference of dyes in nanonaps form and in chloroform, nanonaps were freeze dried overnight and dissolved in same volume of chloroform and absorbances were measured.

Nanonap toxicity: For in vitro studies, 2×10$^4$ Caco-2 cells (ATCC) were seeded in a 96 well plate in 20% fetal bovine serum in Dulbecco's Modified Eagle Medium. The next day, cells were treated with ONc nanonaps or methylene blue at the indicated concentrations. 24 hours later, media was removed and XTT was added to determine viability measuring absorbance at 450 nm. For in vivo studies, mice (Harlan Labs, 6 week BALB/c mice) were administered 1000 OD$_{860}$ per 20 g of ONc nanonaps by gavage (given in 3 administrations within a 24 hour period) or kept as controls (n=5 per each group of male gavage, female gavage, male control and female control group). Behaviour was monitored every other day and mass was measured weekly. After 2 weeks, mice were sacrificed and organs were harvested. PBS was used to rinse blood and debris. The organs were immersed in 10% neutral buffered formalin (VWR #16004-114) and fixed over 24 hours. The fixed organs were processed through increasing grades of alcohol, cleared in xylene and infiltrated with paraffin (TBS). They were subsequently embedded, cut and stained with haematoxylin and eosin. Finally, the slides were scanned with single slide scanner (Aperio).

Photoacoustic experiments. A custom-built volumetric reflection-mode PAT system using a single element ultrasound transducer was used. In briefly, tunable laser pulses were synthesized from an OPO laser (Surelite OPO PLUS; Continuum; wavelength tuning range, 680 to 2500 nm; pulse width, 5 ns; and pulse repetition rate, 10 Hz) excited by a pump laser (SLII-10; Continuum; Q-switched Nd:YAG; 532 nm). An optical wavelength of either 710 or 860 nm, which matched the respective absorption peak of ZnBNc or ONc nanonaps, was used for PA imaging experiments. Generated light passed through a home-made spherical conical lens and optical condenser with a pulse energy of ~5 mJ/cm$^2$, much less than the safety limit. During the raster scanning for volumetric imaging, the acoustic coupling was improved with a custom-made water tray. The mouse (6-8 weeks female BALB/c mouse) was located below the water tray. The induced PA signals were captured by the focused ultrasound transducer (V308; Olympus NDT; 5-MHz center frequency). A Vevo LAZR US/PA imaging system was used for real-time imaging with 21 MHz transducer frequency. The movement of nanonaps in the digestive system was photoacoustically monitored after gavage of 100 ODs of nanonaps in female BALB/c mice. This corresponds to 3.4 mg of ONc nanonaps and 13.2 mg of ZnBNc nanonaps. Region of interest analysis was performed with the system software. Rate of peristaltic calculations per minute was determined by taking the 1$^{st}$ derivative of the region of interest intensity (with 0.2 second resolution) and quantifying number zero crossings (corresponding to contractions) in an averaged 10 second window. Photoacoustic spectral response was recorded using a Vevo LAZR (VisualSonics) and placing samples in PE20 tubing submerged in water in the case of nanonaps and concentration-matched gold nanorods with peak absorption at 860 nm. Nanorod concentration was based on gold alone and was provided by the manufacturer (Nanorods LLC). Depth-response in chicken tissue was determined using the home-built photoacoustic system by layering pieces of chicken tissue on top of tubes containing ZnBNc and ONc nanonaps absorption-matched to 400. 2 and 1.5 mJ/cm$^2$ pulse energies were recorded at the 710 nm and 860 nm wavelengths used to excite the ZnBNc and ONc nanonaps, respectively. For intestinal obstruction studies, 12-14 g female CD-1 mice (Harlan) were fasted overnight with access to water. The abdomen was then opened with a 1 cm transverse incision near the stomach and the duodenum was ligated with nylon sutures (VWR #89219-096). Sham-treated mice had no duodenum ligation performed, but otherwise it was an identical procedure. The abdomen skin was sutured closed again and within a few hours, mice were then administered a 100 OD$_{860}$ dose of ONc nanonaps by gavage. 1 hour later, the mice were anesthetized and imaged with the Vevo LAZR system.

Nanonap radiolabelling experiments. $^{64}$Cu was produced via a 64Ni(p,n)$^{64}$Cu reaction using a CTI RDS 112 cyclotron at the University of Wisconsin-Madison. Pilot studies using increasing amount of nanonaps revealed that good radiolabelling yield (>65%, FIG. 44) could be achieved with as little as 1 µg of nanonaps per 37 MBq of $^{64}$Cu. Even though PET is more sensitive than PAT for in vivo detection, similar amount of nanonaps was used per mouse to ensure comparable biodistribution patterns between the two studies.

For labelling, 37 MBq of $^{64}CuCl_2$ was diluted in 300 µL of 0.1 M sodium acetate buffer (pH 5.5) and added into 400 OD nanonaps. The reaction mixture was incubated for 30 minutes at 37° C. with constant shaking. The $^{64}$Cu-nanonaps were purified by Amicon Ultra-4 centrifugal filter unit (Millipore) with phosphate buffered saline (PBS) as the mobile phase. The final purified $^{64}$Cu-nanonaps were re-suspended in 500 µL of PBS and used for in vitro stability, oral gavage, PET imaging, and biodistribution studies.

For in vitro chelation stability studies, 37 MBq of $^{64}CuCl_2$ was incubated with 1 OD of nanonaps for 30 minutes and unconjugated $^{64}$Cu was separated using 100 kDa cutoff Amicon filters (Millipore, Billerica, Mass.). After that, one OD of $^{64}$Cu-nanonaps were re-suspended in 1 mL of SGF or SIF and incubated at 37° C. with stirring. Portions of the mixture (50 µL) were sampled at different time points (0.5, 1, 2, 4, 8, and 24 hours post-incubation) and filtered through 100 kDa cutoff filters. The filtrates were collected and the radioactivity was measured by a Wizard2 automatic gamma counter (Perkin-Elmer, Waltham, Mass.). The percentages of retained $^{64}$Cu on the nanonaps were calculated using the following equation: (total radioactivity−radioactivity in filtrate)/total radioactivity. All the experiments were carried out in triplicates.

PET scans were performed using an Inveon microPET/microCT rodent model scanner (Siemens Medical Solutions USA, Inc.). After fasting overnight, each BALB/c mouse was administered with ~7.4 MBq of $^{64}$Cu-nanonaps (100 ODs in 125 µL PBS) via oral gavage. Five to ten minute static PET scans were performed at various time points post-injection. The images were reconstructed using a maximum a posteriori (MAP) algorithm, with no scatter correction. Region-of-interest analysis of each PET scan was performed using vendor software (Inveon Research Workplace) on decay-corrected whole-body images to calculate the percentage injected dose per gram of tissue (% ID/g) values for intestines.

After the last PET scans at 24 hours post injection, all the mice were euthanized and biodistribution studies were carried out to confirm that the quantitative tracer uptake values based on PET imaging truly represented the radioactivity distribution in mice. Blood and major organs/tissues were collected and wet weighed. The radioactivity in the tissue was measured using a gamma-counter (Perkin Elmer) and presented as % ID/g.

Figure 29:
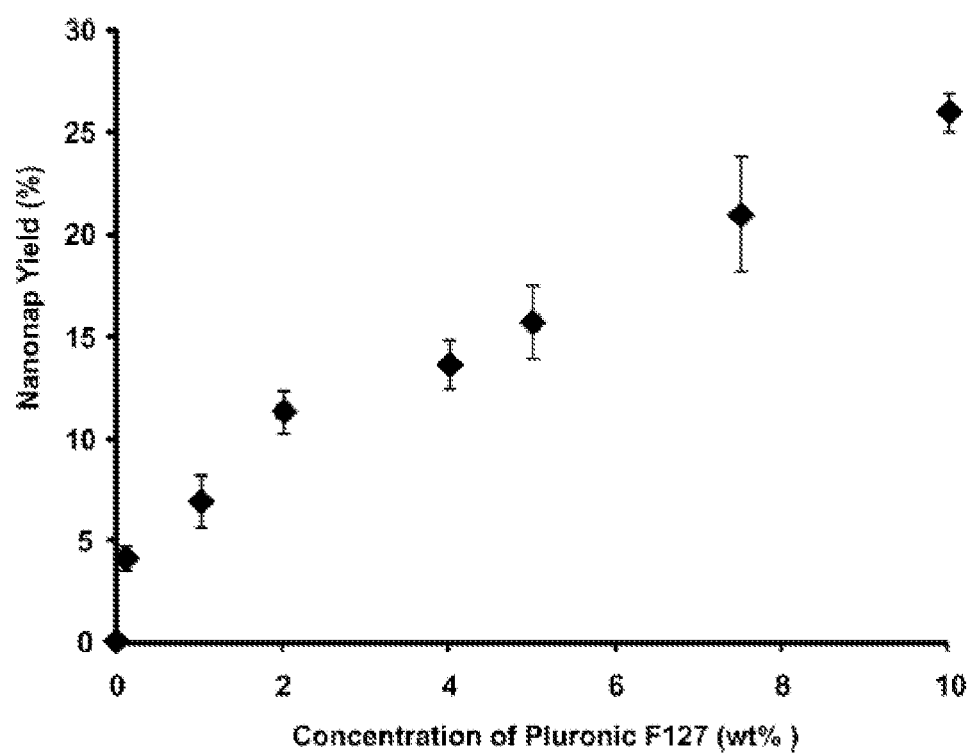
FIG. 29: Yield of nanonaps as a function of initial F127 concentration. Nanonap yield following nanonap formation in solutions of varying Pluronic F127 concentrations. A 10% (w/v) Pluronic F127 was selected for nanonap formulation since solution viscosity increased beyond this concentration. Mean+/−std. dev. for n=3.

Results:

Formation of Frozen Naphthalocyanine Micelles Chromophores of varying hydrophobicity were examined to determine whether they spontaneously assembled into stable nanoparticles following dilution into a biocompatible surfactant. Pluronic (poly(oxyethylene)-poly(oxypropylene)-poly(oxyethylene); PEO-PPO-PEO) F127 was selected because it is approved by the United States Food and Drug Administration (FDA) for oral consumption. To examine chromophore-F127 complex stability, the solutions were then dialyzed against the bile surfactant sodium cholate, which can pass through dialysis tubing due to its small micelle size. As shown in FIG. 23a, dyes that were very hydrophobic based on the octanol-water partition coefficient (Log P values, predicted with the ALOG PS algorithm (Tetko, I. V. & Tanchuk, V. Y., J. Chem. Inf. Comput. Sci. 42, 1136-1145 (2002)), exhibited high retention after dialysis so did not readily exchange with the large excess of cholate micelles. Of the dyes evaluated, phthalocyanine (Pc) and naphthalocyanine (Nc) derivatives (FIG. 23b), which are characterized by their tetrapyrrole structure and extreme hydrophobicity, were nearly fully retained. The presence of a strongly colorful supernatant after centrifugation to remove any aggregates implied the formation of soluble nanoformulated naphthalocyanines (nanonaps). The yield of nanonaps increased with increasing F127 concentrations (FIG. 29). No sharp increase in nanonap yield was observed above the critical micelle concentration (CMC) of F127 (~1% at room temperature), implying a nanonap formation mechanism unrelated to unimer-micelle equilibrium.

Figure 24:
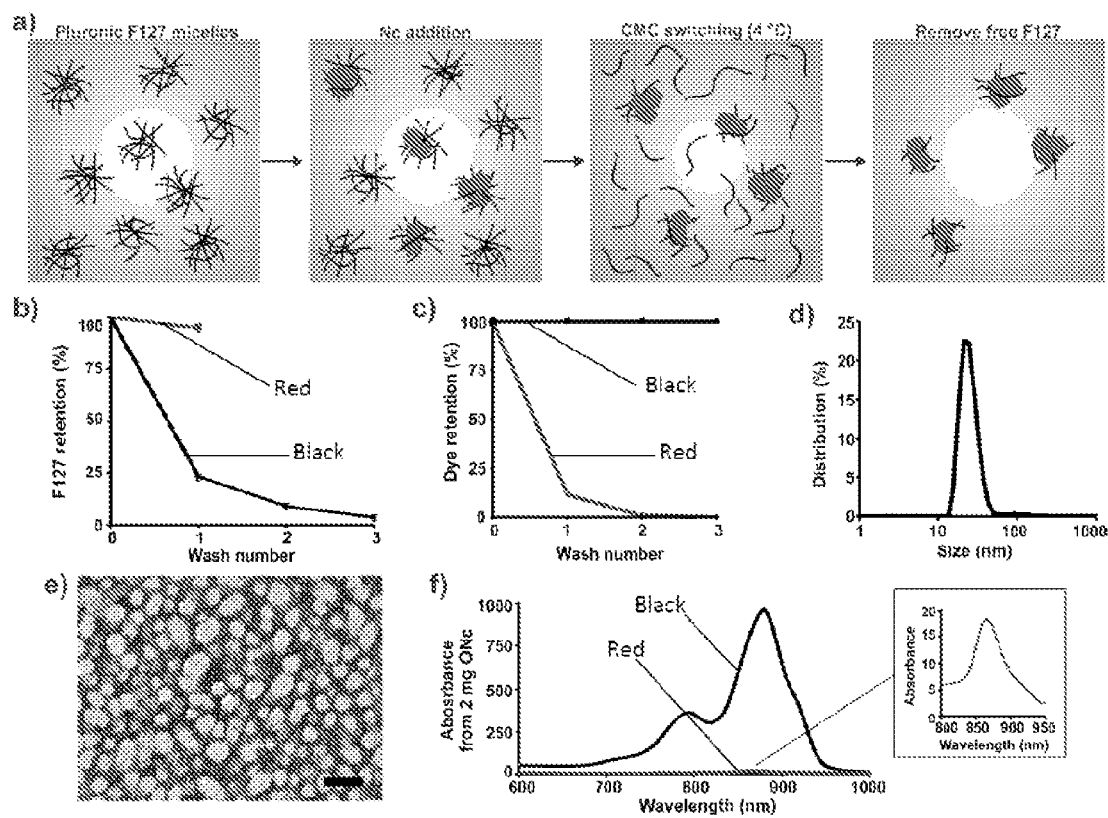
FIG. 24: Temperature-mediated CMC switching to generate surfactant-free nanonaps. a) Generation of purified nanonaps. F127 PEO blocks and PPO blocks are shown as strands and Nc dyes as the filled closed structure. b) F127 retention as a function of centrifugal filtration washes at 4° C. (black) and 25° C. (red). Mean+/−std. dev. for n=3. c) F127-solubilized dye retention as a function of centrifugal filtration washes at 4° C. for Nc (black) and methylene blue (red). Mean+/−std. dev. for n=3. d) Nanonap size distribution by dynamic light scattering in water. e) Negative-stained transmission electron micrograph of dried nanonaps. Scale bar, 50 nm. f) Equivalent absorbance from concentrated, reconstituted nanonaps (black) or liposomes (red, 1:19 molar ratio Nc:lipid) following freeze drying of nanoparticles formed with 2 mg of ONc. Inset shows magnified liposomal absorbance.
Figure 31:
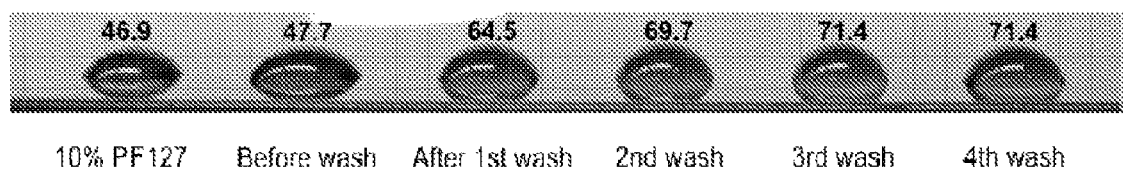
FIG. 31: Contact angle analysis of washing cycles. Determination of wash numbers required to remove free F127 based on contact angle analysis (angle indicated in figure). Nanonaps were formed in a 10% (w/v) solution of F127 ("Before wash") sample and free F127 was removed following CMC switching using centrifugal wash steps.
Figure 32:
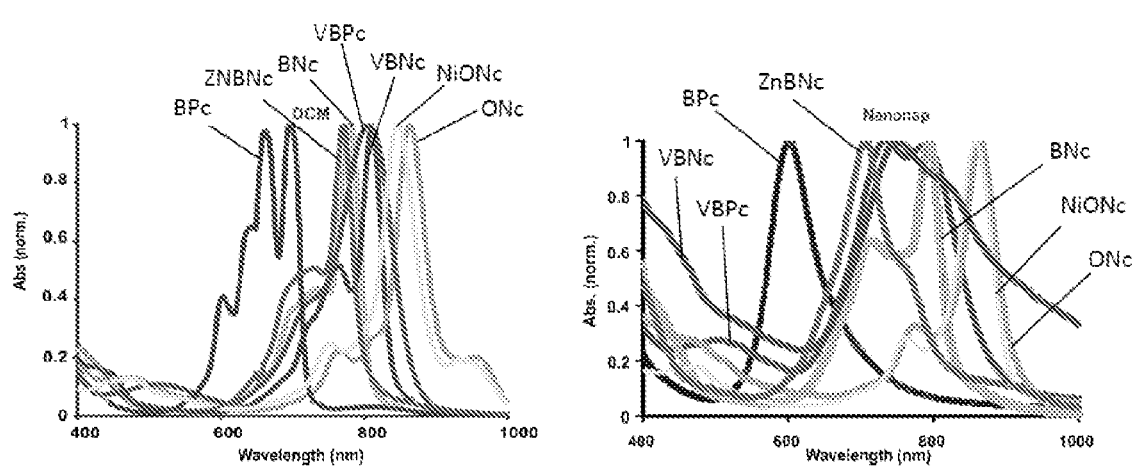
FIG. 32: Normalized absorbance spectrum of Nc dyes in dichloromethane and in aqueous nanonap forms. BPc, ZnBNc, BNc, VBPc, VBNc, ONc, NiONc are shown in blue, dark green, yellow green, purple, pink, amber and yellow, respectively. Shifted absorbance spectra of successfully formed nanonaps compared to the dichloromethane spectra indicated the dense arrangement of Nc dyes in nanonaps modified some electronic properties.

Because F127 has a temperature-sensitive CMC, we examined the effects of lowering the solution temperature to convert micelles to F127 unimers. Reducing the temperature to 4° C. did not result in any Nc aggregation, which can be explained by the formation of the frozen micelles. This enabled a novel strategy for the removal of all excess F127 (FIG. 24a). As shown in FIG. 24b, centrifugal filtration removed all free F127 at 4° C., but the process was ineffective at 25° C., as detected using a previously reported colorimetric assay (FIG. 30). CMC switching did not affect the self-assembly of nanonaps, which were quantitatively retained during the 4° C. washing process (FIG. 24c). All free surfactant was removed from the nanonaps with 3 low temperature wash cycles and no further change in contact angle was observed with additional washing (FIG. 31). Unlike nanonaps, methylene blue (MB), a dye employed for PA applications, was completely removed from the retentate following 3 centrifugal filtration washes.

The nanoparticles formed 20 nm spheres (FIG. 24d, 24e). Because the CMC switching process removed all excess F127, the well-dispersed nanonaps could be concentrated to high dye to F127 molar ratios (>3:1 dye:F127, see FIG. 43). We prepared 2 mg of Nc dye either in a nanonap or a liposomal formulation, using dimyristoylphosphatidylcholine (DMPC) in a 19:1 lipid:dye molar ratio. Following initial solubilization, the solutions were freeze-dried and reconstituted in a minimal volume of water (50 µL). As shown in FIG. 24f, concentrated nanonaps dissolved in water, as evidenced by the extreme Nc NIR absorption of approximately 1000. However, after the freeze-dried liposomes were reconstituted, some Nc re-solubilization was observed but it was orders of magnitude lower than the nanonap formulation. Since CMC switching dramatically reduces the total amount of F127 surfactant present, nanonaps could be reconstituted at a much higher concentration. The phospholipid amounts required for Nc solubilization could not analogously be decreased via CMC switching, and following freeze-drying and further concentration during reconstitution, the phospholipid concentration was above the solubility limit. Difficulty in encapsulation could be further impacted by amorphous precipitation of the Nc during solvent removal.

Figure 33:
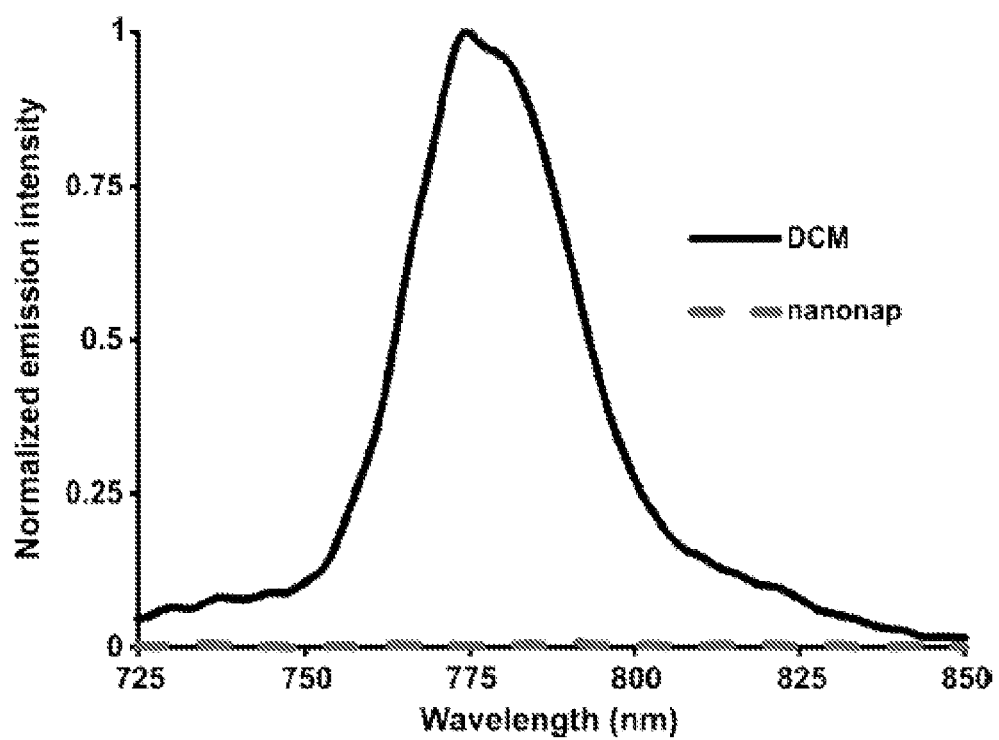
FIG. 33: Self-quenched fluorescence emission of ZnBNc nanonaps. Fluorescence of absorption-matched ZnBNc nanonaps in water and free ZnBNc in dichloromethane (DCM).
Figure 34:
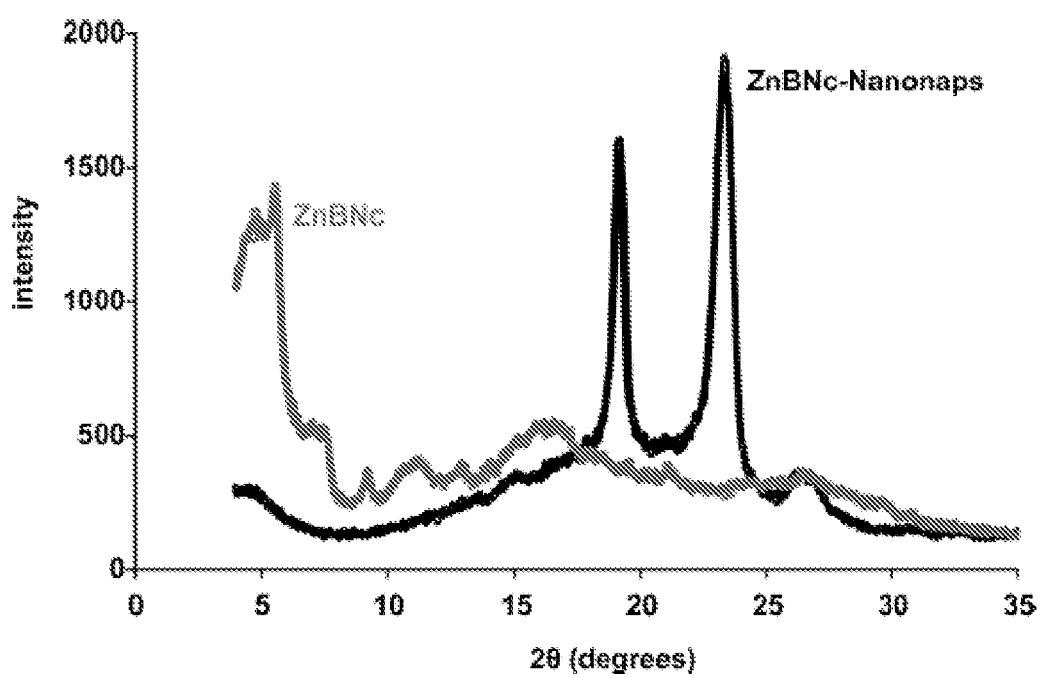
FIG. 34: X-ray diffraction spectrum of freeze-dried ZnBNc nanonaps and pure ZnBNc. Although ZnBNc (grey line) exhibits weak crystallization properties compared to Pluronic F127, small peaks indicate some crystallization orientation (at 7°). However, these disappeared after nanonap formation (black line). The two large peaks observed in nanonaps are due to characteristic Pluronic F127 crystal patterns based on PEO crystallinity.

Since nanonaps could be generated from a range of hydrophobic Pc and Nc chromophores (FIG. 23a), we set out to identify a subset with spectral properties spanning the NIR window. Different commercially available Pc and Nc dyes were screened using the CMC switching method to generate pure nanonaps (Supplementary FIG. 4). Dye extinction coefficients ranged from $1.0$-$2.2 \times 10^5$ $M^{-1}$ $cm^{-1}$ in organic solvents, whereas in nanonap form these decreased to $0.4$-$1.5 \times 10^5$ $M^{-1}$ $cm^{-1}$ (FIG. 43). This suggests the dense arrangement of Ncs in nanonaps led to altered electronic properties and intermolecular interaction, which was further supported by full fluorescence self-quenching of aqueous nanonaps (FIG. 33). Powder diffraction analysis of freeze dried samples did not reveal any presence of crystalline Nc within the nanonaps, showing the dyes were probably embedded with F127 without organized stacking (FIG. 34). It is assumed that the nanonap interior is an amorphous blend of the dyes and hydrophobic F127 PPO blocks. However, since structural studies have shown the gyration radius of F127 PPO blocks is only 1.6 nm, and given the contiguous nature of PEO-PPO-PEO blocks, the interior of the nanonaps may also contain a small portion of hydrophilic PEO, which would segregate from the more hydrophobic Nc and PPO. The aqueous-facing shell of nanonaps is presumed to be composed exclusively of PEO.

Figure 25:
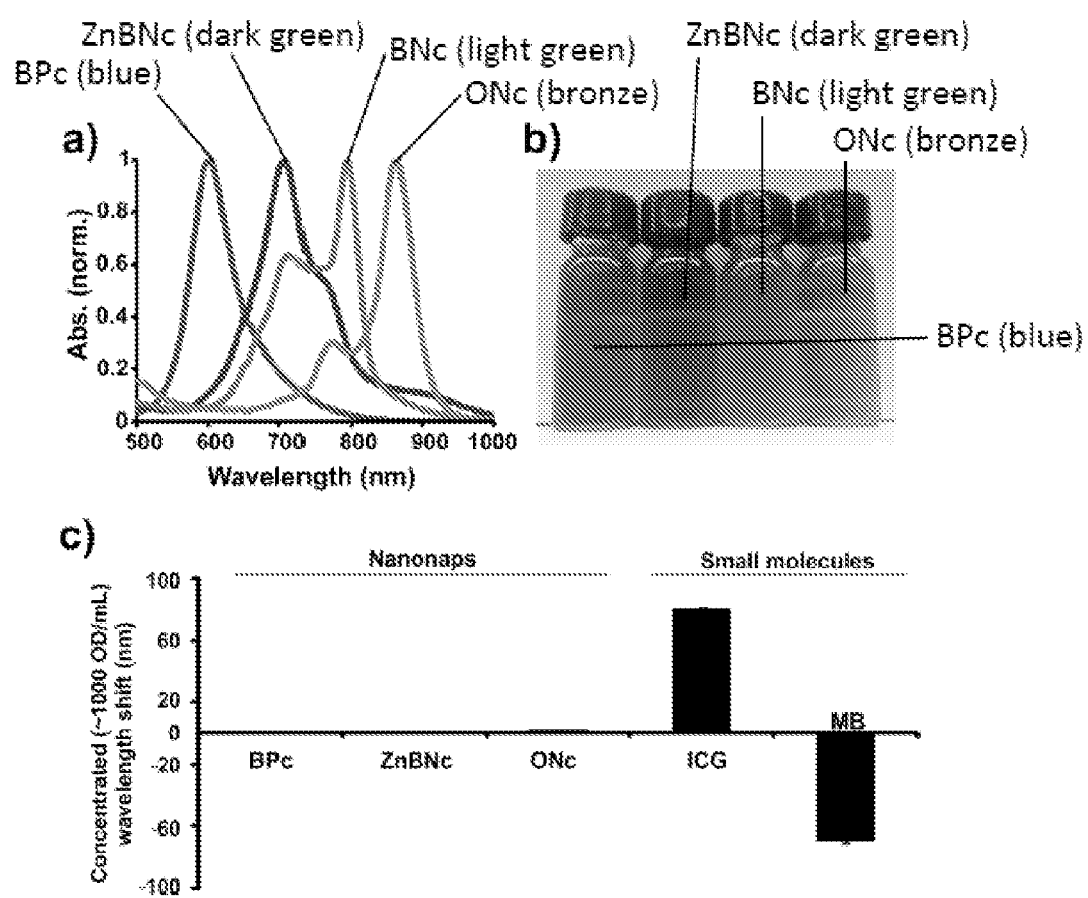
FIG. 25: Multispectral nanonaps without peak wavelength shifting at ultrahigh optical densities. a) Normalized absorbance of nanonaps formed from BPc (blue), ZnBNc (dark green), BNc (light green) or ONc (bronze). b) Photograph of nanonaps in water. From left to right: BPc, ZnBNC, BNc and ONc. c) Absorption peak wavelength shift at high optical densities. Concentrated solutions were measured in a 10 μm path length cuvette and compared to a 1000 fold dilution in water. Indicated nanonaps are compared to indocyanine green (ICG) and methylene blue (MB). Mean+/−std. dev. for n=3.
Figure 35:
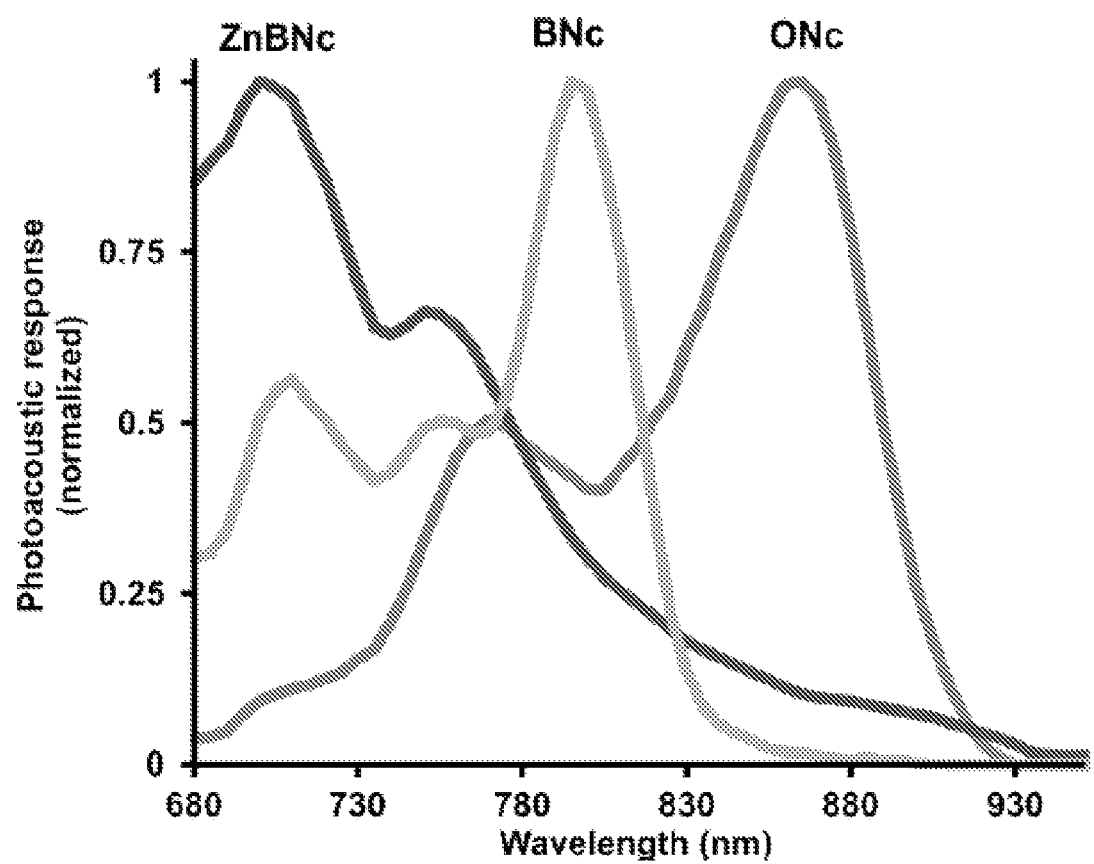
FIG. 35: Photoacoustic spectra of ZnBNc, BNc and ONc nanonaps. The maximal absorbance of the indicated nanonaps was adjusted to 10 and PA spectral scans were conducted in PE20 tubing on a Vevo LAZR.
Figure 36:
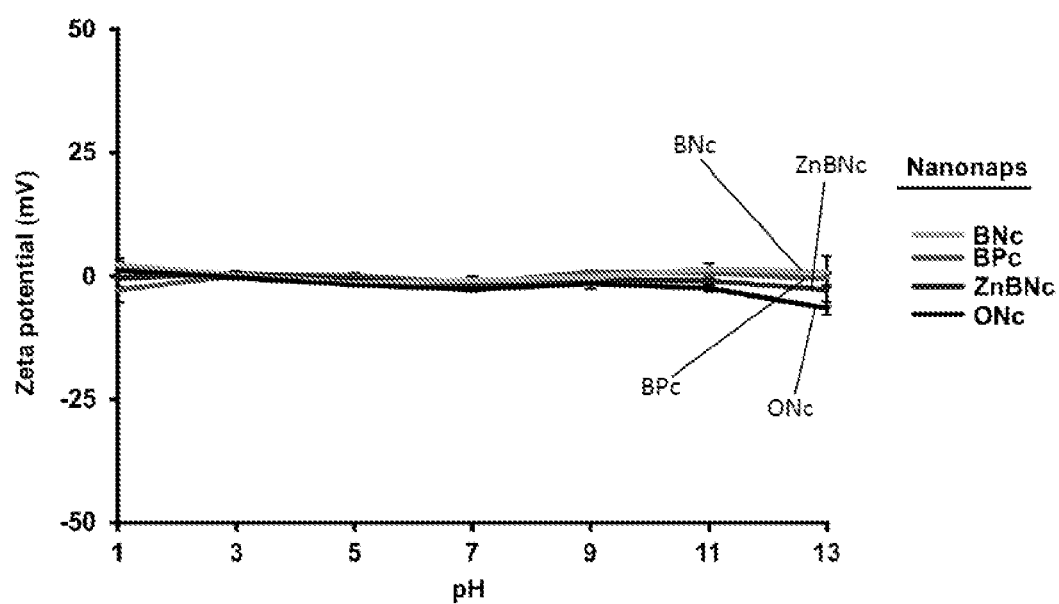
FIG. 36: Nanonaps maintain near neutral zeta potential over broad pH range. Nanonaps were diluted into pH-adjusted phosphate buffer and zeta potential was recorded. Mean+/−std. dev. for n=3

1 Pc and 3 Nc dyes were identified that gave rise to nanonaps with peaks at 600, 707, 793 and 863 nm (FIG. 25a, b). The nanonaps generated absorption spanning the NIR spectrum while maintaining reasonably narrow full-width half-maxima (50-100 nm). Since PA imaging can resolve multiple absorption wavelengths, multi-wavelength classes of nanoparticles are desirable. The PA spectral response of nanonaps aligned with their absorption spectra (FIG. 35). The nanoparticles could be concentrated into fully soluble solutions with absorptions of greater than 1000. One advantage of nanonaps compared to free dyes was that upon concentration, absorption peak positions displayed negligible shifting (FIG. 25c). This was assessed by measuring absorption of a concentrated solution (1000 optical densities (OD)/mL) in a 10 µm path length, and then measuring a 1000 fold dilution of the same solution in a 1 cm path length. The commonly used PA dyes MB and indocyanine green exhibited large absorption shifts in concentrated solutions, as a result of modulated electronic properties induced by self-interaction encountered at high concentration. On the other hand, Ncs co-assembled with F127 in the nanonap matrix exhibited no modified peak absorption shifts, demonstrating that nanonaps prevented concentration-dependent dye interaction that would otherwise affect absorption at higher concentrations. Although concentration-dependent absorption shifts can be useful in PA imaging, concentration-independent optical parameters lead to simplified analysis of contrast movement, as would be the case for GI-photoacoustic tomography (PAT). Based on zeta potential measurements, nanonaps maintained a nearly neutral surface charge over a broad range of pH values (FIG. 36).

Absorbance, as measured on a spectrophotometer, includes effects of both absorption and scattering. However, only absorption contributes to the photoacoustic effect. Resonance light scattering was used to estimate scattering. Compared to extinction-matched gold nanorods, nanonaps exhibited negligible scattering. Nanonaps are considered to have no scattering component. Based on the molar ratio of Nc to F127 in the purified nanonaps and geometric calculations, we estimated that each 5,9,14,18,23,27,32,36-Octabutoxy-2,3-naphthalocyanine (ONc) nanonap contains 501 molecules of Nc and 155 molecules of F127, with an optical cross section of $2.9 \times 10^{-17}$ m$^2$. Additional optical parameters are reported in FIG. 43. Although this cross section is two orders of magnitude lower than that of nanorods, the unique dispersibility of nanonaps enables them to be concentrated to orders-of-magnitude higher particle density while maintaining solubility. As a result, stable nanoparticle solutions are achievable with overall absorptions greater than 1000.

Photoacoustic Gut Imaging

Figure 26:
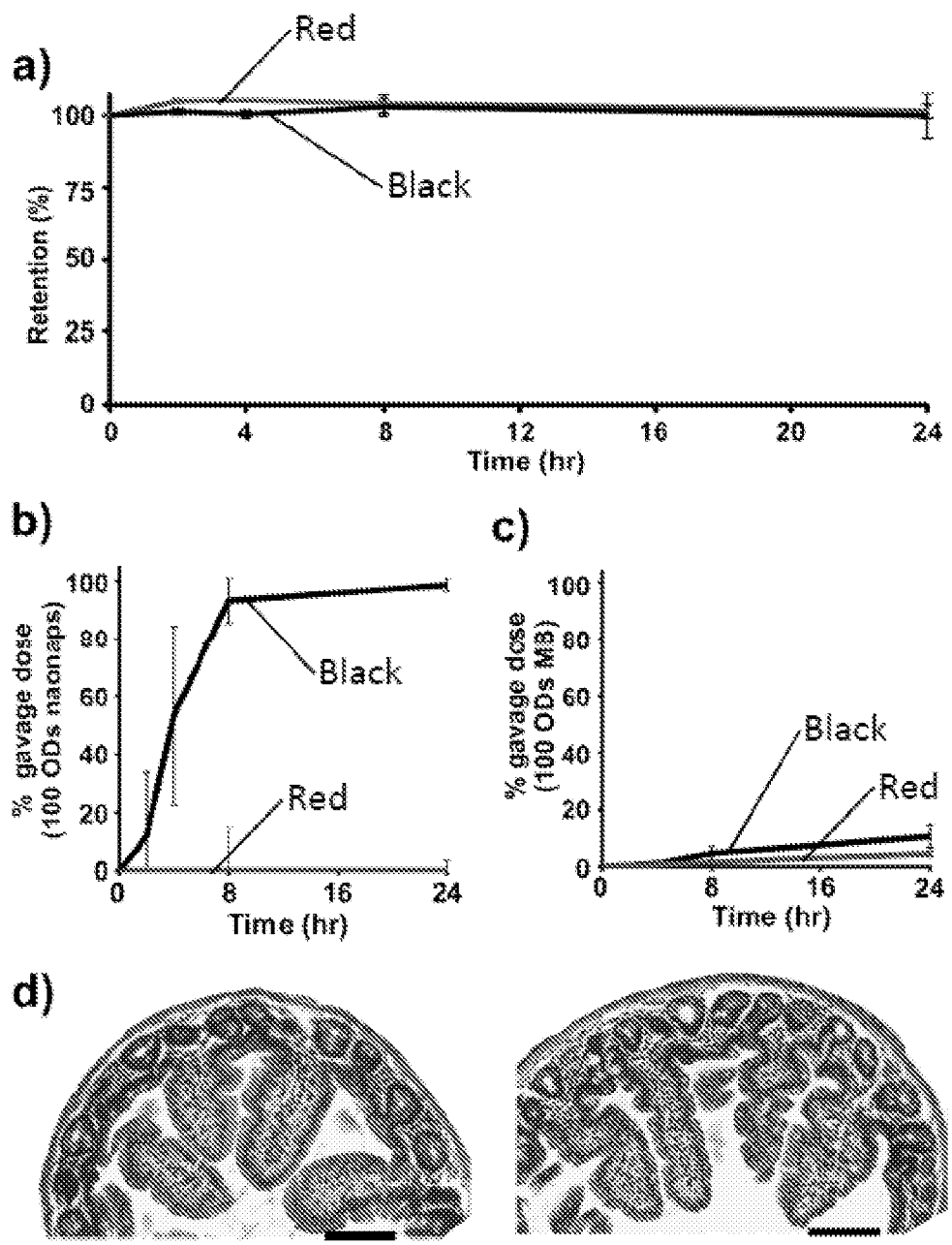
FIG. 26: Nanonaps pass safely through the intestine following oral administration. a) Retention of ONc nanonaps dialyzed in simulated gastric fluid (red) or simulated intestinal fluid (black) at 37° C. Mean+/−std. dev. for n=3. b) Excretion of 100 optical densities ("ODs"—one OD is defined as the amount of nanoparticles required to produce absorbance of 1 in a 1 mL solution measured with a standard 1 cm pathlength) of ONc nanonaps in feces (black) and urine (red). Mean+/−std. dev. for n=3 mice. c) Excretion of 100 ODs of methylene blue (MB) in feces (black) and urine (red). Mean+/−std. dev. for n=3 mice. d) Haematoxylin and eosin-stained intestine section of a control mouse (left) or a mouse 24 hours after gavage of 100 ODs of ONc nanonaps (right). Villi and crypts were intact without influx of inflammatory cells. Scale bar, 100 μm.
Figure 37:
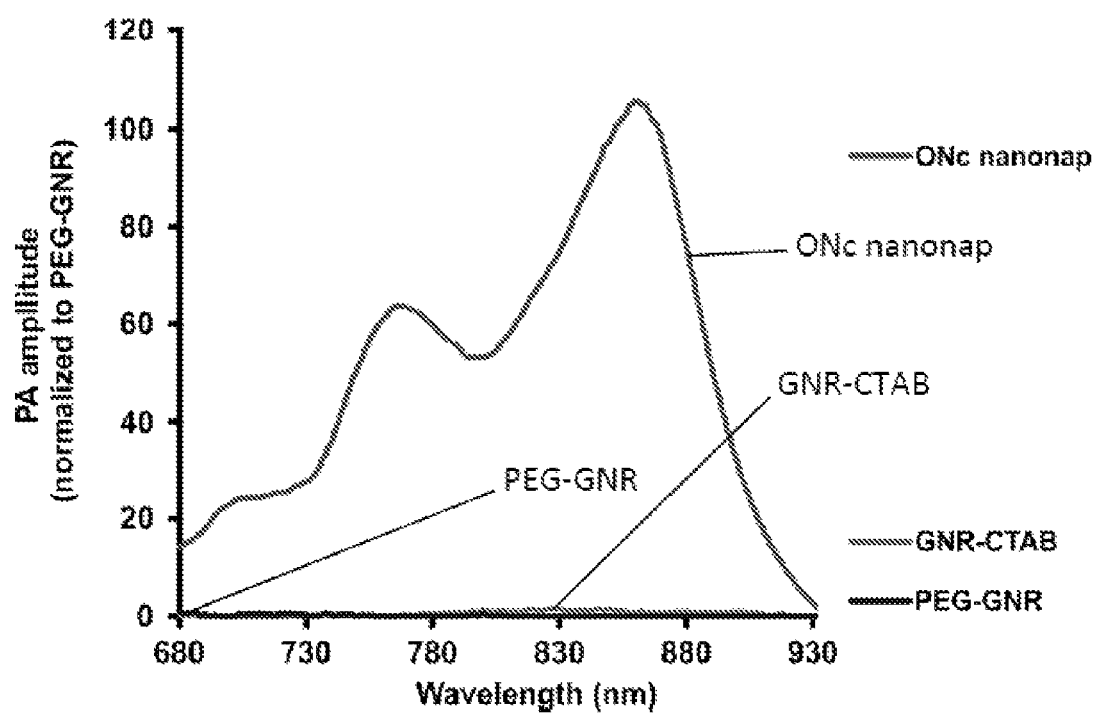
FIG. 37: Photoacoustic spectra of concentration-matched nanonaps and gold nanorods. ONc nanonaps and gold were normalized to 1.2 mg/mL concentration and photoacoustic spectra was recorded on a Vevo LAZR. Nanorod mass is based on gold alone. Representative of three separate trials.

To assess the suitability of nanonaps for use as an orally administered PA agent, we determined if nanonaps could withstand the harsh conditions of the stomach and intestine, which often pose hurdles for nanoparticles. When nanonaps were dialyzed in simulated gastric fluid (SGF) or simulated intestinal fluid (SIF) at 37° C., no appreciable loss of absorption was observed, demonstrating stability in harsh dialysis conditions (FIG. 26a). In water, 1.2 mg/mL ONc nanonaps generated over one hundred time greater photoacoustic signal than concentration-matched and wavelength-matched gold nanorods (FIG. 37).

Figure 38:
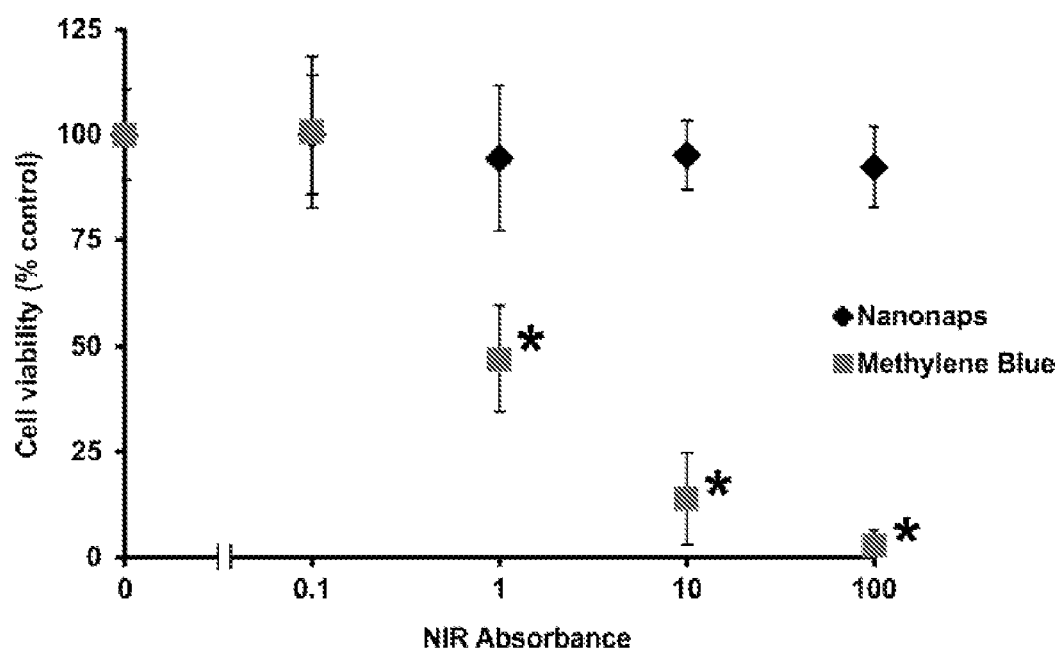
FIG. 38: Caco-2 cell viability following incubation with nanonaps or methylene blue. Concentrated ONc nanonaps and methylene blue solutions were diluted into Caco-2 cell medium, with final NIR absorbances as indication. Cells were incubated with dyes for 24 hours in DMEM media with 20% serum at 37° C., then viability was assessed using the XTT assay. Mean+/−std. dev. for n=6. No statistically significant difference was found between control and any of the nanonap-treated groups, based on one-way ANOVA. For methylene blue, the asterisks mark statistically significant groups from the untreated control based following one-way ANOVA and Tukey's posthoc analysis (p<0.001).

The cellular toxicity of ONc nanonaps was assessed using Caco-2 cells. Whereas MB induced toxicity when incubated in cell media with absorbance greater than 1, nanonaps did not exhibit any toxicity up to absorbance of 100, the highest value tested (FIG. 38). Encouraged by these results, we administered 100 ODs of ONc nanonaps via gavage to mice. Nanonaps were completely excreted in the feces (FIG. 26b). The lack of intestinal absorption likely stemmed from both the 20 nm size of the nanonaps which prevents passive diffusion through membranes, and the PEO character of F127, which prevents bioadsorption. For comparison, 100 ODs of MB was administered in the same manner MB was systemically absorbed and was detectable in urine, with most of the MB remaining in the body or getting metabolized (FIG. 26c).

Figure 39:
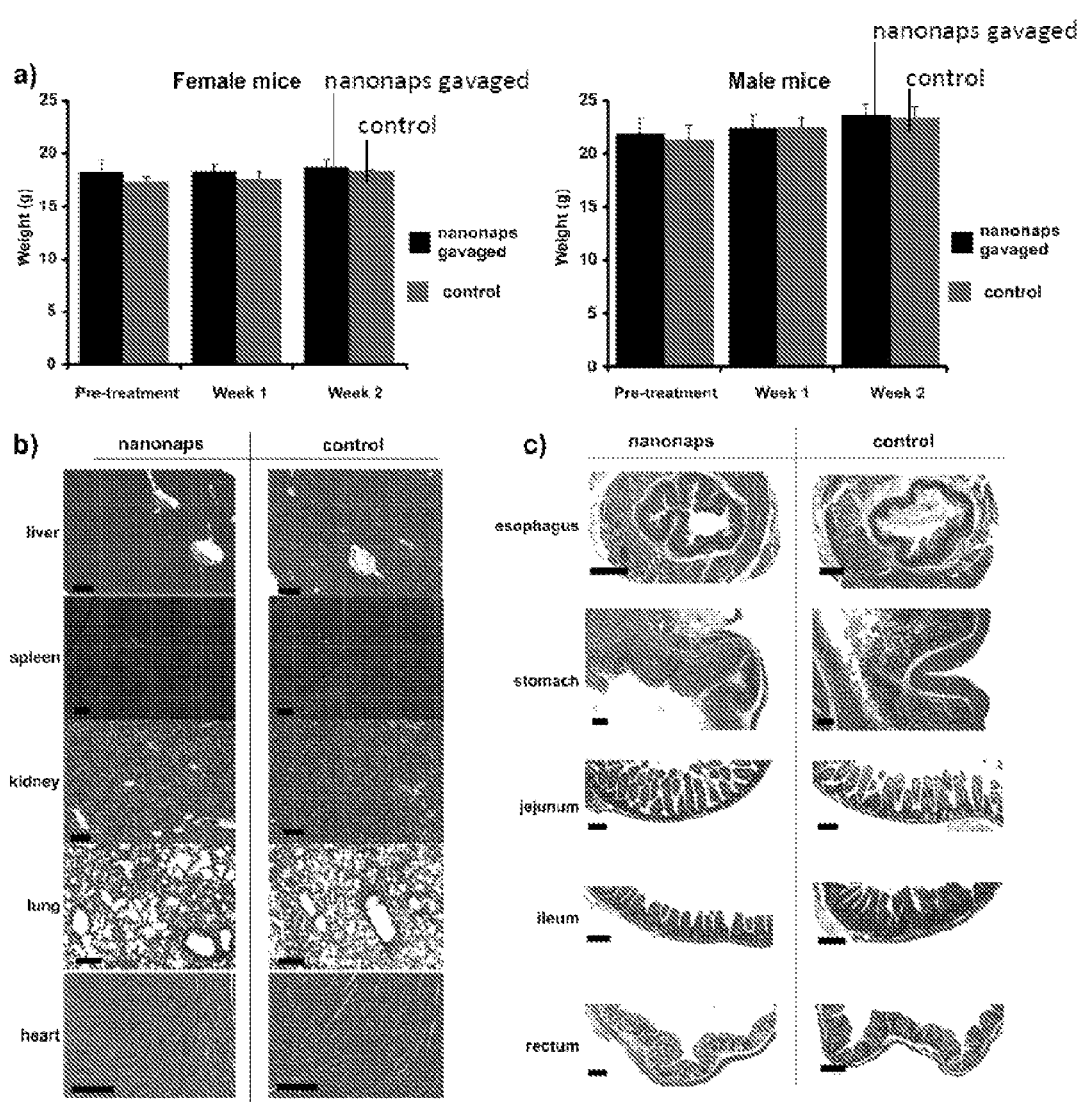
FIG. 39: 50,000 $OD_{860}$/kg nanonaps is a safe orally-administered nanonap dose. a) Mouse mass following gavage of 1000 OD doses. Within the 2-week period, mice displayed no signs of distress or abnormal behaviour. Mean+/−std. dev for n=5 mice for each male (+/−nanonap) and female (+/−nanonap) group. No statistically significant differences were observed between the mass of treated and control mice following study completion (based on 2-tailed students t-test, P>0.05) b) Histology of H&E stained liver, spleen, kidneys, lungs and heart from treated or control mice. No signs of systemic toxicity were observed. c) Histology of organs of the GI tract including the esophagus, stomach, small intestine and large intestine revealed no obvious damage based on H&E staining. All scale bars represent 200 μm.

The effect of nanonaps on intestinal tissues was examined using histology (FIG. 26d). No noticeable inflammatory response or damaging effects were induced and intestinal villi and crypts appeared healthy. Given the safety of nanonaps predicted by their quantitative excretion and lack of systemic absorption, we next assessed the acute toxicity of nanonaps using an oral dose of 50,000 OD$_{860}$/kg. This represents a 10 fold excess of the functional nanonap dose used for imaging applications. There were no adverse behavioural or weight changes in male or female mice over the two week study (FIG. 39a). Histology revealed no systemic (FIG. 39b) or gastrointestinal (FIG. 39c) toxicity.

Figure 27:
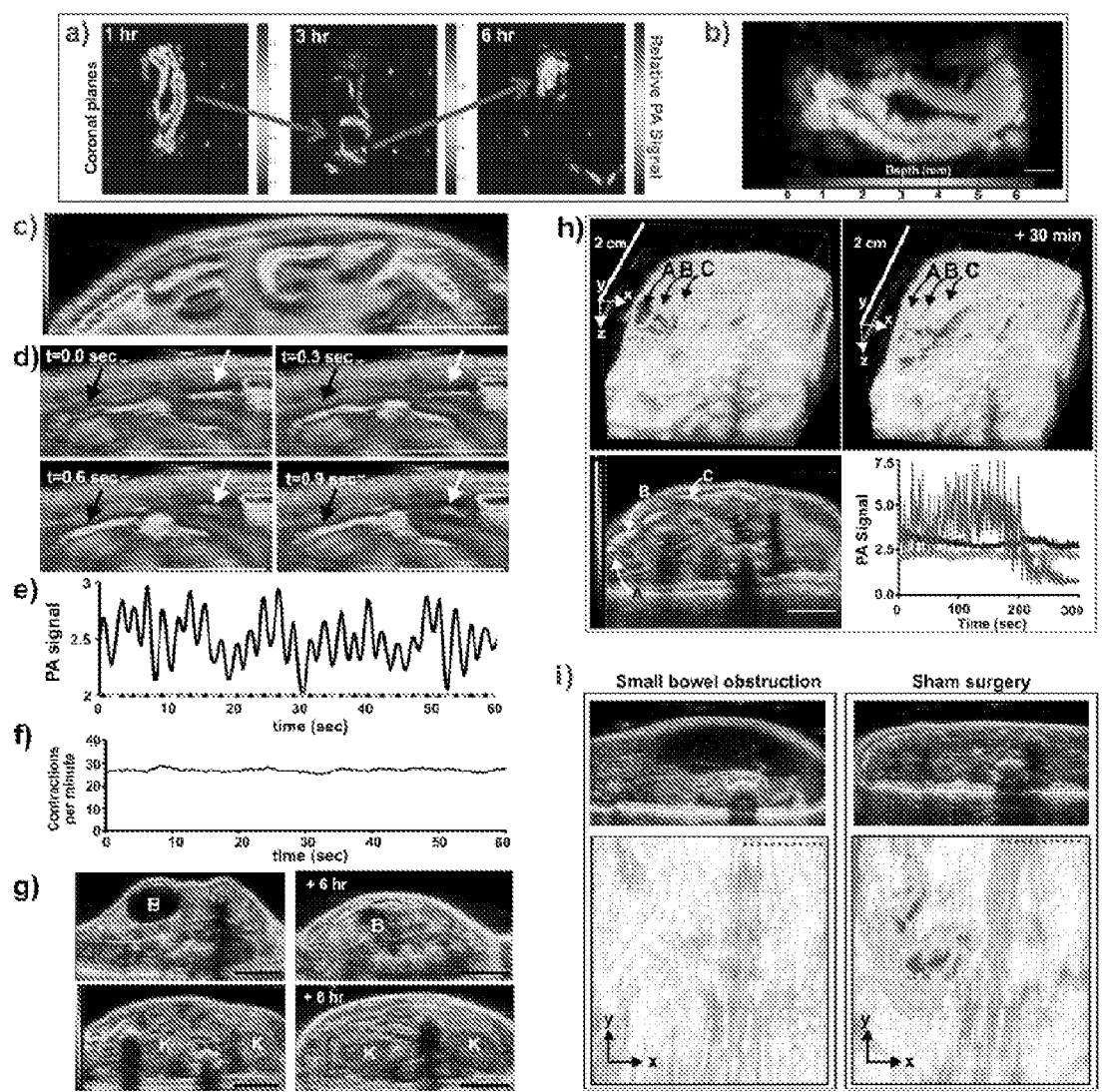
FIG. 27: Non-invasive anatomical and functional PA imaging of the intestine using nanonaps. a) PA maximum intensity projection (MIP) of nanonaps following gavage of 100 ODs of ZnBNc nanonaps using a single transducer PA system. Red arrows show nanonap transit. b) Depth-encoded PA MIP of the intestine visualizing ZnBNc nanonaps. c) Real-time multimodal mouse intestinal transverse plane with PA signal (colour) and simultaneous US (grey) acquisition following gavage of 100 ODs of ONc nanonaps. d) Nanonap movement in the intestine. Black arrow shows inflow and white arrow shows outflow. e) Intestinal region of interest analysis. First derivative zero-crossings provide the time of maximal nanonap inflow (black triangles) and outflow points (grey triangles). f) Rate of contractile motion from the region, plotted over time. g) Co-registered US for anatomical mapping of nanonaps. The bladder (B) and kidneys (K) are located with US (grey), while nanonap PA signal is shown in colour. h) US (grey)/PA (colour) MIPs of transverse slices show ONc nanonap intestinal transit over time. The MIP was used to orient the PA signal within a single slice of interest (lower left). Outflow quantification over time of nanonaps in area "A" (red) is shown in reference to two others that maintained steady nanonap content in "B" (blue) and "C" (grey). The fluctuations in "A" are due to contractile inflow and outflow of nanonaps. i) US/PA detection of intestinal obstruction. Mice were subjected to duodenal ligations or sham surgery. 3.4 mg (corresponding to 100 $OD_{860}$) ONc nanonaps were administered and mice were imaged 1 hour later. The top shows a transverse slice 2.4 cm above the bladder, showing the swollen stomach in the obstructed mice. The bottom shows US/PA MIPs. Unobstructed flow of nanonaps is clear in the sham group. The dashed line indicates approximate surgical incision site and the image width corresponds to 2.4 cm. Representative images for n=3 per group. Solid scale bars, 5 mm where indicated.

We next examined the utility of nanonaps for non-invasive PAT of the intestine in vivo. As shown in FIG. 27a, PA imaging using a custom-built single-element scanning system revealed the biodistribution of nanonaps in the GI tract with 100 nm axial resolution. Progression of Zinc-2,11,20, 29-Tetra-tert-butyl-2,3-naphthalocyanine (ZnBNc) nanonaps through the intestine was clearly observed. Negligible background was detected, enabling clear resolution of intestinal features and individual small bowel diverticula were distinguishable. Depth encoding analysis revealed further spatial details of intestinal distribution with depth mapping to 5 mm (FIG. 27b).

For dynamic imaging, a Vevo LAZR transducer array system was used. 100 ODs of ONc nanonaps were administered via gavage. As shown in the transverse slice in FIG. 27c, PA (colour) overlaid perfectly with US (grey) to reveal nanonap distribution in intestine below the stomach surface with minimal background. The 5 frames per second scanning speed enabled detailed tracking of nanonap movement in the intestine. Rapid changes in nanonap flow were readily apparent (FIG. 27d) and detailed peristaltic movements were clear. By selecting a region of interest that displayed undulating nanonap content, segmentation or peristaltic flow was quantified. Flow of nanonaps into a representative region of interest occurred periodically with distinct inflow and outflow movements (FIG. 27e). Calculation of the rate of peristaltic intestinal flow shown in FIG. 27f demonstrated contractions close to 30 per minute.

By examining US co-registration, intestinal nanonap distribution was mapped to anatomical features. As shown in FIG. 27g, bladder and kidneys were identified with US and the relative position of adjacent intestinal nanonaps changed over time. Two US/PA maximum intensity projection (MIPs) were generated from a stack of scans that trace the movement of nanonaps through the intestine over a 30 minute period (FIG. 27h). The MIP is useful to provide intestinal orientation in any given individual transverse slice. The indicated regions of interest showed, in real time, the out-of-plane passing of nanonaps through a transverse slice of the intestine. Compared to control regions "B" and "C", containing relatively constant nanonap volumes, nanonaps quantitatively exited from region "A" over one minute and exhibited peristaltic contractions in the process.

Small bowel obstructions cause 300,000 operations annually in the United States. To determine whether US/PA imaging could be useful for detecting intestinal obstructions, we used a surgically-induced duodenal ligation mouse model. Following duodenal ligation or sham treatment (opening the abdomen but omitting the ligation), the abdomen was sutured closed. The mice were then administered a 100 $OD_{860}$ dose of ONc nanonaps and imaged one hour post-gavage. The stomachs of the mice with obstructions visibly swelled to a large volume. US transverse slices showed a prominent void stomach volume in the ligated mice, but not the sham-treated ones (FIG. 27i, top). Although US could distinguish the bloated stomach of the obstructed mice, the PA signal was barely detectable. The enlarged stomachs of the obstructed mice contained large pockets of air that may have caused PA attenuation and further investigation into this phenomenon is required. In the obstructed mice, barely any PA signal was detected over the entire intestinal area (FIG. 27i, bottom) However, sham-treated mice displayed a strong PA signal, demonstrating that nanonaps progressed uninhibited through the intestine. Thus, nanonaps may be useful as a diagnostic tool for detection of small bowel obstructions.

Figure 40:
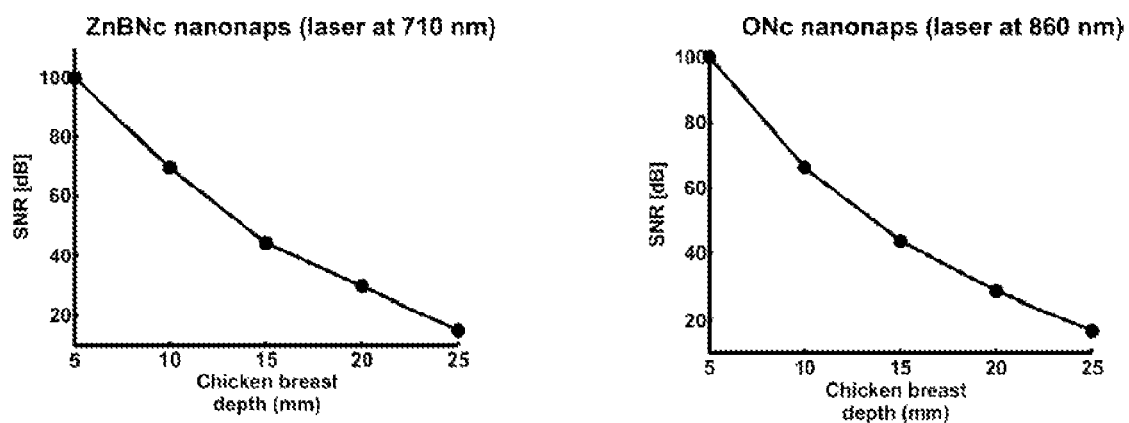
FIG. 40: Signal to noise ratio of ZnBNc and ONc nanonaps in a chicken breast phantom. Absorbance matched (absorbance of ~400) ZnBNc and ONc nanonaps were placed in a chicken phantom and photoacoustic signal was monitored with progressive addition of chicken breast tissue. Energy pulse densities were 2 and 1.5 mJ/cm$^2$ at 710 nm and 860 nm respectively.

Based on their high absorption, both ZnBNc (707 nm) and ONc nanonaps (860 nm) were suitable for low-background GI PA imaging. The selection of optimal nanonap wavelength is case-dependent. For example, many tunable lasers currently used in photoacoustic instrumentation generate higher laser output at 707 nm, whereas 860 nm may have less intrinsic biological background and scattering. In chicken breast tissue, absorbance-matched ONc and ZnBNc nanonaps could both easily be detected up to 2.5 cm in depth, with similar photoacoustic signal-to-noise ratios (FIG. 40). The pulse energies used were only 2 and 1.5 $mJ/cm^2$, corresponding to only ~1/10 and ~1/30 of the laser safety limits for ZnBNc and ONc nanonaps wavelengths respectively.

Positron Emission Tomography

Although PA technology is rapidly improving, deep tissue (>5 cm) PA imaging is yet to be reported in humans. Since positron emission tomography (PET) is clinically used for non-invasive whole body imaging, we examined nanonap-based PET imaging as a complementary technique. The 4 pyrrole nitrogens within the Nc macrocycle can coordinate with copper to serve as a chelator and it has been shown that the positron emitter $^{64}Cu$ can be used to conveniently label intact tetrapyrrole-based nanoparticles. Because nanonaps are formed from Ncs themselves, no additional steps of chelator conjugation are required.

Figure 28:
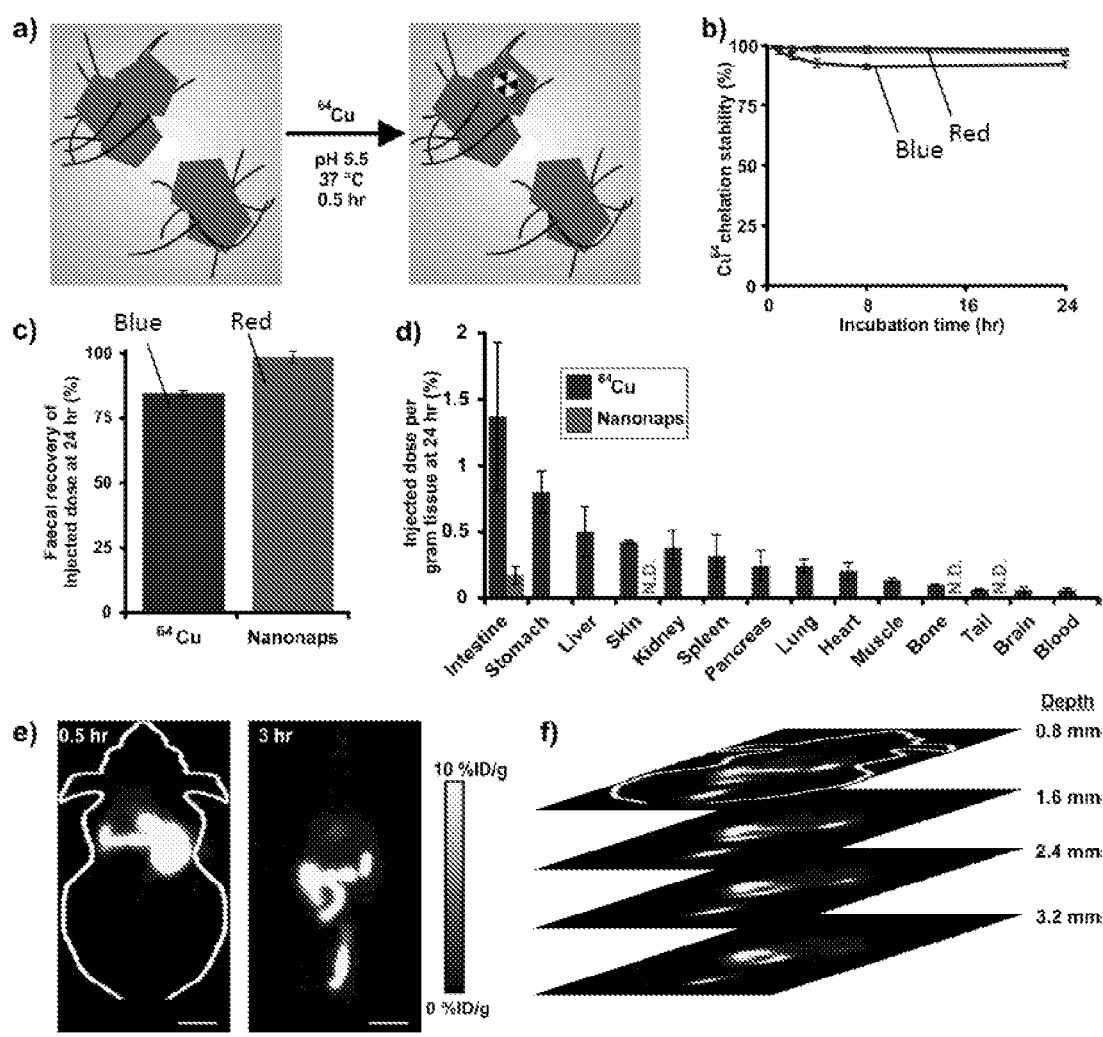
FIG. 28: Seamless nanonap labelling with 64Cu for whole body PET imaging of the GI tract. a) Nanonap labelling using 64Cu. F127 PEO blocks are shown in blue, PPO blocks in black, Nc dyes in red and 64Cu is shown as the radioactive yellow circle. b) Retention stability of 64Cu chelation in radiolabelled nanonaps in simulated gastric fluid (red), simulated intestinal fluid (blue) and water (black) incubated at 37° C. Mean+/−std. dev. for n=3. c) Fecal clearance of ONc nanonaps and chelated 64Cu in mice 24 hours after gavage of 100 ODs of ONc nanonaps. 64Cu was assessed using gamma counting and nanonaps using absorption. Mean+/−std. dev. for n=3-4 mice d) Biodistribution of 64Cu and nanonaps 24 hours after gavage. No data ("N.D.") was obtained for some organs since they were not measured. Mean+/−std. dev. for n=3-4 mice. e) Representative PET imaging of nanonaps. 100 ODs of 64Cu-labelled ONc nanonaps were gavaged and mice were imaged at the indicated time points. Scale bar, 1 cm. f) Representative 0.8 mm thick coronal slices through the mouse, 3 hours after gavage.
Figure 41:
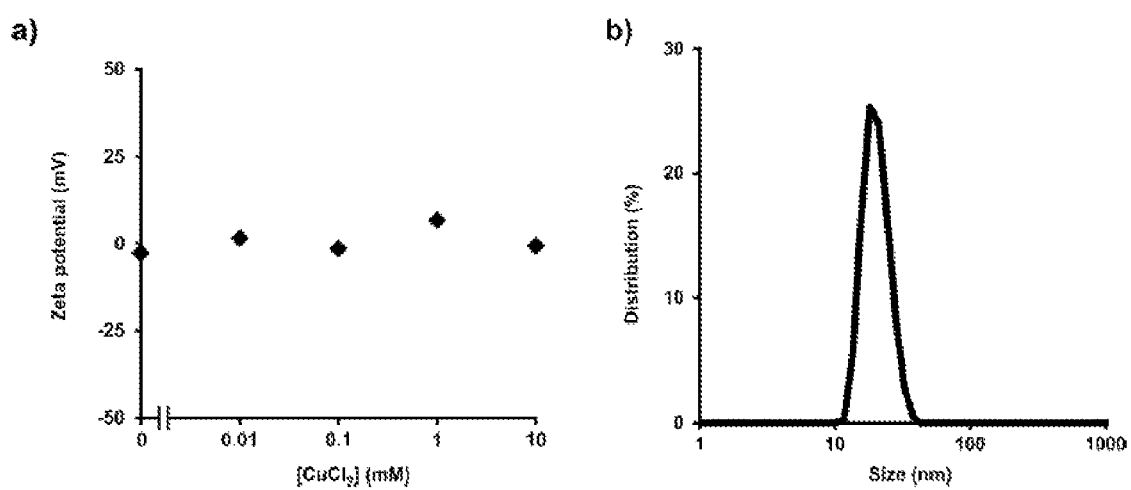
FIG. 41: Copper labelling does not affect nanonap zeta potential or size. ONc nanonaps (100 ODs) were incubated in 0, 0, 01, 0.1, 1, 10 mM cold $CuCl_2$ at 37° C. for 30 minutes with constant shaking. Labelled nanonaps were washed 4 times with centrifugal filtration to remove excess copper and zeta potential was measured. Mean+/−std. dev. for n=3. Size is shown for 10 mM labelling conditions.

When nanonaps were incubated with $^{64}Cu$ in aqueous solution, labelling was achieved in just 30 minutes with over 65% radiolabelling yield (FIG. 28a and FIG. 44). Size and zeta potential were unaffected (FIG. 41). Following the removal of free copper, when $^{64}Cu$-nanonaps were incubated in SIF and SGF at 37° C., the chelation was stable in vitro (FIG. 28b). A 100 $OD_{860}$ dose of radiolabelled ONc nanonaps was then gavaged (7.4 MBq per mouse). 99% of nanonaps were excreted in feces, compared to 85% of the $^{64}Cu$ radiolabel (FIG. 28c). This discrepancy was likely due to the displacement of some of the copper from the Nc chelate in the harsh GI environment. Minimal radioactivity remained in any part of the mouse, with all organs retaining less than 1.5% ID/g of $^{64}Cu$ (FIG. 28d). Since they were cleared in feces, nanonaps themselves were not detected in any organs, except for a small trace amount remaining in the intestine.

PET was used to follow the movement of nanonaps through the GI tract. Radioactivity was present in the stomach and upper intestine after oral gavage, as can be seen from the PET images at 0.5 hours (FIG. 28e). A clear distribution pattern of $^{64}Cu$-nanonaps in the intestine was observed 3 hours after administration. Since PET is tomographic with no tissue penetration limits, serial whole-body consecutive coronal slices of the mouse could be obtained (FIG. 28f). Tomographic analysis revealed background-free intestinal visualization in three dimensions.

Owing to high Nc hydrophobicity, kinetically-frozen nanonaps could be formed that are stable in the gut, avoid systemic absorption, and give rise to extreme and tunable optical absorption in the NIR. They are organic, assembled from an FDA-approved surfactant, and are completely excreted in feces without observed toxicity. Real-time US/PA gut imaging using nanonaps provided for high resolution, low-background, real-time proof-of-principle mapping of intestinal anatomy, pathology and function. Additionally, direct use of nanonaps for PET enables quantitative, sensitive, clinically-established imaging approaches with full tissue penetration for whole body imaging. The spatial resolution limitations of PET (a few mm) can be compensated with localized PAT techniques using a single agent. Beyond GI imaging, based on their multimodal nature, stability and small size above the renal clearance threshold, nanonaps also hold potential for use as an intravenously administered contrast agent. Future directions of research may include modifying nanonap surface properties for targeted detection and examining multi-color PA imaging for diagnosis of gut diseases.

While the present disclosure is described through specific embodiments, routine modifications will be apparent to those skilled in the art and such modifications are intended to be within the scope of the disclosure.

The invention claimed is:

1. An aqueous composition comprising micelles, said micelles comprising poloxamer and encapsulating one or more hydrophobic agents thereby forming hydrophobic agent-loaded poloxamer micelles, wherein the hydrophobic agent:poloxamer molar ratio in the composition is at least 3:1 and at least 95% of the poloxamer in the composition forms the hydrophobic agent-loaded micelles.

2. The composition of claim 1, wherein at least 96, 97, 98 or 99% of the poloxamer molecules in the formulation are present in hydrophobic agent-loaded micelles.

3. The composition of claim 1, wherein the hydrophobic agent is a drug and the drug:poloxamer molar ratio is from 7:1 to 60:1.

4. The composition of claim 1, wherein the hydrophobic agent is an optical contrast dye and the of dye:poloxamer molar ratio is from 3:1 to 10:1.

5. The composition of claim 1, wherein the poloxamer is F127, F68, F108 or a mixture thereof.

6. The composition of claim 1, wherein the hydrophobic agent has an octanol-water partition coefficient of at least 3.

7. The composition of claim 1, wherein the hydrophobic agent is a drug selected from the group consisting of Alpha-Tocopherol, Abafungin, Amiodarone, Azithromycin Dihydrate, Bepridil, Beta-carotene, Budesonide, Cabazitaxel, Carbamazepine, Calciferol, Carvedilol, Chloroquine, Chlorpromazine, Cholecalciferol, Clotrimazole, Coenzyme Q10, Cotinine, Cyclizine, Cyclosporine A, Diazepam, Docetaxel, Econazole, Ergocalciferol, Etoposide, Fentanyl, Fenofibrate, Finasteride, Fulvestrant, Haloperidol, Haloperidol decanoate, Itraconazole, Ivermectin, Labetalol, Latanoprost, Meloxicam, Miconazole, Mifepristone, Mycophenolate mofetil, Nimodipine, Paclitaxel, Phenytoin, Piroxicam, Pregnenolone, Pregnenolone Acetate, Progesterone, Propofol, Reserpine, Retinol, Retinol Palmitate, Sertaconazole, Sibutramine, Simvastin, Sirolimus, Squalene, Tacrolimus, Tamoxifen , Temsirolimus, Testosterone, Testosterone cypionate, Testosterone priopionate, Testosterone undecanoate, Tipranavir, Travoprost, Triamcinolone, Vitamin K1, and combinations thereof.

8. The composition of , claim 1, wherein the hydrophobic agent is an optical contrast dye selected from the categories of phthalocyanine (Pc), naphthalocyanine (Nc), chlorin, porphyrin, and bacteriochlorin.

9. A method for making a composition comprising micelles suitable for transport of hydrophobic agents comprising:
    a) contacting a hydrophobic agent dissolved in organic solvent with an aqueous solution of poloxamer thereby forming hydrophobic agent-loaded poloxamer micelles;
    b. causing poloxamer molecules which are not forming hydrophobic agent-loaded micelles to become unitary poloxamer units by exposure to a temperature from −20° C. to 10° C.; and
    c. removing the unitary poloxamer units to result in hydrophobic agent-loaded micelle, wherein at least 85% of the poloxamer molecules are removed, wherein the hydrophobic agent:poloxamer molar ratio is from 3:1 to 60:1, and wherein 95% or more poloxamer in the composition is present in hydrophobic agent-loaded micelles.

10. The method of claim 9, wherein the organic solvent in a) is at a concentration of 10-200 mg/mL and the aqueous solution of poloxamer is at a concentration of 5-15% (w/v).

11. The method of claim 9, wherein the hydrophobic agent is a drug and the hydrophobic agent:poloxamer molar ratio in c) is 10:1 to 60:1.

12. The method of claim 9, wherein the hydrophobic agent is a imaging contrast dye and the hydrophobic agent:poloxamer molar ratio in c) is 3:1 to 10:1.

13. The method of claim 9, further comprising freeze-drying the composition from c).

14. A hydrophobic agent-loaded micelle composition made by the method of claim 9.

15. A method of drug delivery comprising:
    a) obtaining a hydrophobic drug-loaded micelle composition of claim 3;
    b) administering to an individual the micelle composition.

16. A method for imaging at least a portion of the gastrointestinal (GI) tract in an individual comprising:
    a) obtaining a hydrophobic dye-loaded micelle composition of claim 4, wherein the dye is suitable for imaging;
    b) administering to an individual via oral route the dye loaded micelle composition; and c) after a suitable period of time after administration, obtaining one or more images of the GI tract using photoacoustic or positron emission tomography imaging.

17. The method of claim 16, wherein the dye is 2,11,20,29-tetra-tert-butyl-2,3-naphthalocyanine (BNc), Zinc-2,11,20,29-tetra-tert-butyl-2,3-naphthalocyanine (ZnBNc), 5,9,14,18,23,27,32,36-Octabutoxy-2,3-naphthalocyanine (ONc),Nickel-5,9,14,18,23,27,32,36-Octabutoxy-2,3-naphthalocyanine (NiONc), Vanadyl 2,11,20,29-tetra-tert-butyl-2,3-naphthalocyanine (VBNc), 2,9,16,23-tetra-tert-butyl-29H,31H-phthalocyanine (BPc), Vanadyl 3,10,17,24-tetratert-butyl-1,8,15,22-tetrakis(dimethylamino)-29H,31H-phthalocyanine (VBPc), or a combination thereof.

\* \* \* \* \*

UNITED STATES PATENT AND TRADEMARK OFFICE
CERTIFICATE OF CORRECTION

PATENT NO. : 9,757,334 B2
APPLICATION NO. : 15/322593
DATED : September 12, 2017
INVENTOR(S) : Jonathan Lovell et al.

It is certified that error appears in the above-identified patent and that said Letters Patent is hereby corrected as shown below:

In the Claims

Column 36, at Line 58, in Claim 4, "an optical contrast dye and the of dye:poloxamer" should read:
--an optical contrast dye and the dye:poloxamer--;

Column 37, at Line 27, in Claim 9, "b." should read:
--b)--;

Column 37, at Line 31, in Claim 9, "c." should read:
--c)--;

Column 38, Line 31, in Claim 17, "(ONc),Nickel-5" should read:
--(ONc), Nickel-5--;

And

Column 38, at Lines 34-36, in Claim 17, "Vanadyl 3,10,17,24-tetratert-butyl-1,8,15,22-tetrakis(dimethylamino)-29H,31H-phthalocyanine (VBPc)" should read:
--Vanadyl 3,10,17,24-tetra-tert-butyl-1,8,15,22-tetrakis(dimethylamino)-29H,31H-phthalocyanine (VBPc)--.

Signed and Sealed this
Thirteenth Day of December, 2022

Katherine Kelly Vidal
*Director of the United States Patent and Trademark Office*